US006984502B2

(12) United States Patent
Kapeller-Libermann et al.

(10) Patent No.: US 6,984,502 B2
(45) Date of Patent: Jan. 10, 2006

(54) METHODS AND COMPOSITIONS OF HUMAN 69087 NUCLEIC ACIDS AND USES THEREOF

(75) Inventors: Rosana Kapeller-Libermann, Chestnut Hill, MA (US); Rajesekhar Bandaru, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 424 days.

(21) Appl. No.: 10/044,205

(22) Filed: Oct. 22, 2001

(65) Prior Publication Data

US 2002/0123464 A1 Sep. 5, 2002

Related U.S. Application Data

(60) Provisional application No. 60/242,428, filed on Oct. 23, 2000.

(51) Int. Cl.
*C12N 15/00* (2006.01)

(52) U.S. Cl. ..................... 435/69.1; 536/23.1; 530/350; 435/320.5

(58) Field of Classification Search ................ 536/23.1; 435/69.1, 320.5; 530/350
See application file for complete search history.

(56) References Cited

U.S. PATENT DOCUMENTS

| | | | |
|---|---|---|---|
| 5,998,188 | A | 12/1999 | Stork et al. |
| 6,165,767 | A | 12/2000 | Lai et al. |
| 6,331,423 | B1 | 12/2001 | Guegler et al. |
| 6,444,456 | B1 | 9/2002 | Walke et al. |
| 6,579,709 | B2 | 6/2003 | Guegler et al. |

FOREIGN PATENT DOCUMENTS

| | | |
|---|---|---|
| WO | WO 99/41539 A2 | 9/1998 |
| WO | WO 99/57144 A2 | 11/1999 |
| WO | WO 00/55173 A1 | 9/2000 |
| WO | WO 00/63393 A1 | 10/2000 |
| WO | WO 01/29221 A2 | 4/2001 |
| WO | WO 01/38503 A2 | 5/2001 |
| WO | WO 01/57188 A2 | 8/2001 |
| WO | WO 01/57190 A2 | 8/2001 |
| WO | WO 01/96547 A2 | 12/2001 |

OTHER PUBLICATIONS

Scott et al (Nature Genetics, 1999, 21:440–443).*
Skolnick et al. (2000, Trends in Biotech. 18:34–39).*
Bork (2000, Genome Research 10:398–400).*
Doerks et al. (1998, Trends in Genetics 14:248–250).*
Smith et al. (1997, Nature Biotechnology 15:1222–1223).*
Brenner (1999, Trends in Genetics 15:132–133).*
Bork et al. (1996, Trends in Genetics 12:425–427).*
Bowie et al. (1990, Science 247:1306–1310).*
Weiss, Ellen R. et al., "Species–Specific Differences in Expresssion of G–Protein–Coupled Receptor Kinase (GRK) 7 and GRK 1 in Mammalian Cone Photoreceptor Cells: Implications for Cone Cell Phototransduction", The Journal of Neuroscience 21(23):9175–9184 (2001).
Chen, Ching–Kang et al., "Characterization of Human GRK7 as a Potential Cone Opsin Kinase", Molecular Vision 7 :305–313 (2001).
Cidyciyan, Artur V. et al., "Cone Deactivation Kinetics and GRK1/GRK7 Expression in Enhanced S Cone Syndrome Caused by Mutants in NR2E3", Investigative Ophthalmology and Visual Science 44(3) :1268–1274 (2003).
GENBANK® Database, Accession No. AAC95001.
GENBANK® Database, Accession No. AAD33910.
GENBANK® Database, Accession No. AF063016.
GENBANK® Database, Accession No. BAA25670.
GENBANK® Database, Accession No. BAB32498.
GENBANK® Database, Accession No. CAC10195.
GENBANK® Database, Accession No. CAC10539.
GENBANK® Database, Accession No. P28563.
Hisatomi et al., "A novel subtype of G–protein–coupled receptor kinase, GRK7, in teleost cone photoreceptors," FEBS Lett. 424(3):159–164 (1998).
Nagase et al., "Prediction of the coding sequences of unidentified human genes. XX. The complete sequences of 100 new cDNA clones from brain which code for large proteins in vitro," DNA Research 8:85–95 (2001).
Perez et al., "Recruitment and the role of nuclear localization in polyglutamine–mediated aggregation," J. Cell Biol. 143(6):1457–1470 (1998).
Weiss et al., "The cloning of GRK7, a candidate cone opsin kinase, from cone–and rod–dominant mammalian retinas," Mol. Vis. 4:27 (1998).
Zhao et al., "Molecular forms of human rhodopsin kinase (GRK1)," J. Biolog. Chem. 273(9):5124–5131 (1998).

* cited by examiner

*Primary Examiner*—Jeffrey Siew
*Assistant Examiner*—Misook Yu
(74) *Attorney, Agent, or Firm*—Millennium Pharmaceuticals Inc.

(57) ABSTRACT

The invention provides isolated nucleic acids molecules, including 69087 nucleic acid molecules, which encode a novel G protein coupled receptor kinase. The invention also provides recombinant expression vectors containing 69087, nucleic acid molecules, and host cells into which the expression vectors have been introduced.

7 Claims, 23 Drawing Sheets

```
GACCCTAAGATGAAGGGACCTCACTATAGGGCTCGAGCGGCCGCCCGGGCAGGTGCTTTCGCCTTGGCAGGTGGGAGCA
TGACCTATCGTGTGCAGTTCCTGGCGGGCTATACATAGCCAGTCAAAGCTTCTTACAAAAGAAACCTCTTTCACACCCT
CCACGGGTCCCACCCACAGGCCACAGGACTCACTGTAAATCCCTTGGACGTTGTCTCACCCGGGAAGGGAAAGCAGCCA

                                                M   V   D   M   G   A       6
GCAGCCCTCCAGCCCTCTTGTGCTTTCCCTGGGAGTGCGCCCCGTGCTCAGCC ATG GTG GAC ATG GGG GCC      18

 L   D   N   L   I   A   N   T   A   Y   L   Q   A   R   K   P   S   D   C   D     26
CTG GAC AAC CTG ATC GCC AAC ACC GCC TAC CTG CAG GCC CGG AAG CCC TCG GAC TGC GAC    78

 S   K   E   L   Q   R   R   R   R   S   L   A   L   P   G   L   Q   G   C   A     46
AGC AAA GAG CTG CAG CGG CGG CGG CGT AGC CTG GCC CTG CCC GGG CTG CAG GGC TGC GCG   138

 E   L   R   Q   K   L   S   L   N   F   H   S   L   C   E   Q   Q   P   I   G     66
GAG CTC CGC CAG AAG CTG TCC CTG AAC TTC CAC AGC CTG TGT GAG CAG CAG CCC ATC GGT   198

 R   R   L   F   R   D   F   L   A   T   V   P   T   F   R   K   A   A   T   F     86
CGC CGC CTC TTC CGT GAC TTC CTA GCC ACA GTG CCC ACG TTC CGC AAG GCG GCA ACC TTC   258

 L   E   D   V   Q   N   W   E   L   A   E   E   G   P   T   K   D   S   A   L    106
CTA GAG GAC GTG CAG AAC TGG GAG CTG GCC GAG GAG GGA CCC ACC AAA GAC AGC GCG CTG   318

 Q   G   L   V   A   T   C   A   S   A   P   A   P   G   N   P   Q   P   F   L    126
CAG GGG CTG GTG GCC ACT TGT GCG AGT GCC CCT GCC CCG GGG AAC CCG CAA CCC TTC CTC   378
```

Fig. 1A

```
S   Q   A   V   A   T   K   C   Q   A   A   T   T   E   E   E   R   V   A   A    146
AGC CAG GCC GTG GCC ACC AAG TGC CAA GCA GCC ACC ACT GAG GAA GAG CGA GTG GCT GCA  438

V   T   L   R   K   A   E   A   M   A   F   L   Q   E   Q   P   F   K   D   F    166
GTG ACG CTG CGC AAG GCT GAG GCC ATG GCT TTC TTG CAA GAG CAG CCC TTT AAG GAT TTC  498

V   T   S   A   F   Y   D   K   F   L   Q   W   K   L   F   E   M   Q   P   V    186
GTG ACC AGC GCC TTC TAC GAC AAG TTT CTG CAG TGG AAA CTC TTC GAG ATG CAA CCA GTG  558

S   D   K   Y   F   T   E   F   R   V   L   G   K   G   G   F   G   E   V   C    206
TCA GAC AAG TAC TTC ACT GAG TTC AGA GTG CTG GGG AAA GGT GGT TTT GGG GAG GTA TGT  618

A   V   Q   V   K   N   T   G   K   M   Y   A   C   K   K   L   D   K   K   R    226
GCC GTC CAG GTG AAA AAC ACT GGG AAG ATG TAT GCC TGT AAG AAA CTG GAC AAG AAG CGG  678

L   K   K   K   G   G   E   K   M   A   L   L   E   K   E   I   L   E   K   V    246
CTG AAG AAG AAA GGT GGC GAG AAG ATG GCT CTC TTG GAA AAG GAA ATC TTG GAG AAG GTC  738

S   S   P   F   I   V   S   L   A   Y   A   F   E   S   K   T   H   L   C   L    266
AGC AGC CCT TTC ATT GTC TCT CTG GCC TAT GCC TTT GAG AGC AAG ACC CAT CTC TGC CTT  798

V   M   S   L   M   N   G   G   D   L   K   F   H   I   Y   N   V   G   T   R    286
GTC ATG AGC CTG ATG AAT GGG GGA GAC CTC AAG TTC CAC ATC TAC AAC GTG GGC ACG CGT  858
```

Fig. 1B

```
 G   L   D   M   S   R   V   I   F   Y   S   A   Q   I   A   C   G   M   L   H    306
GGC CTG GAC ATG AGC CGG GTG ATC TTT TAC TCG GCC CAG ATA GCC TGT GGG ATG CTG CAC   918

 L   H   E   L   G   I   V   Y   R   D   M   K   P   E   N   V   L   L   D   D    326
CTC CAT GAA CTC GGC ATC GTC TAT CGG GAC ATG AAG CCT GAG AAT GTG CTT CTG GAT GAC   978

 L   G   N   C   R   L   S   D   L   G   L   A   V   E   M   K   G   G   K   P    346
CTC GGC AAC TGC AGG TTA TCT GAC CTG GGG CTG GCC GTG GAG ATG AAG GGT GGC AAG CCC  1038

 I   T   Q   R   A   G   T   N   G   Y   M   A   P   E   I   L   M   E   K   V    366
ATC ACC CAG AGG GCT GGA ACC AAT GGT TAC ATG GCT CCT GAG ATC CTA ATG GAA AAG GTA  1098

 S   Y   S   Y   P   V   D   W   F   A   M   G   C   S   I   Y   E   M   V   A    386
AGT TAT TCC TAT CCT GTG GAC TGG TTT GCC ATG GGA TGC AGC ATT TAT GAA ATG GTT GCT  1158

 G   R   T   P   F   K   D   Y   K   E   K   V   S   K   E   D   L   K   Q   R    406
GGA CGA ACA CCA TTC AAA GAT TAC AAG GAA AAG GTC AGT AAA GAG GAT CTG AAG CAA AGA  1218

 T   L   Q   D   E   V   K   F   Q   H   D   N   F   T   E   E   A   K   D   I    426
ACT CTG CAA GAC GAG GTC AAA TTC CAG CAT GAT AAC TTC ACA GAG GAA GCA AAA GAT ATT  1278

 C   R   L   F   L   A   K   K   P   E   Q   R   L   G   S   R   E   K   S   D    446
TGC AGG CTC TTC TTG GCT AAG AAA CCA GAG CAA CGC TTA GGA AGC AGA GAA AAG TCT GAT  1338
```

Fig. 1C

```
 D   P   R   K   H   H   F   F   K   T   I   N   F   P   R   L   E   A   G   L   466
GAT CCC AGG AAA CAT CAT TTC TTT AAA ACG ATC AAC TTT CCT CGC CTG GAA GCT GGC CTA 1398

 I   E   P   P   F   V   P   D   P   S   V   V   Y   A   K   D   I   A   E   I   486
ATT GAA CCC CCA TTT GTG CCA GAC CCT TCA GTG GTT TAT GCC AAA GAC ATC GCT GAA ATT 1458

 D   D   F   S   E   V   R   G   V   E   F   D   D   K   D   K   Q   F   F   K   506
GAT GAT TTC TCT GAG GTT CGG GGG GTG GAA TTT GAT GAC AAA GAT AAG CAG TTC TTC AAA 1518

 N   F   A   T   G   A   V   P   I   A   W   Q   E   E   I   I   E   T   G   L   526
AAC TTT GCG ACA GGT GCT GTT CCT ATA GCA TGG CAG GAA GAA ATT ATA GAA ACG GGA CTG 1578

 F   E   E   L   N   D   P   N   R   P   T   G   C   E   E   G   N   S   S   K   546
TTT GAG GAA CTG AAT GAC CCC AAC AGA CCT ACG GGT TGT GAG GAG GGT AAT TCA TCC AAG 1638

 S   G   V   C   L   L   L   *                                                  553
TCT GGC GTG TGT TTG TTA TTG TAA                                                1662

ATTGCTCTCTTTACCAGACAGGCAGCAGGAGTCTCGGCTGACATAATCCTCGAATGTTCCACACGTGGAAATCTGTGGA
ATGAGGGCTAATCAGTTAGGAGGGACATCACAACCACAAAACAATTCAAAAGACAGGCAAGCTCACTACTAGAACACAT
TTTATTTTCTTTTTCTTTCTTCATAAAGATGAGTAAAGTCTCAGTTTTCACTGAGGGCAGGGAAAAGGAACACTCAGGT
TTATTTTGA
```

Fig. 1D

```
69087   MVDMGALDNLIANTA YLQARKPSDCDSKEL QRRRRSLALPGLQGC AELRQKLSLNFHSLC
SGK064  MVDMGALDNLIANTA YLQARKPSDCDSKEL QRRRRSLALPGLQGC AELRQKLSLNFHSLC
ST GRK7 M-DMGGLDNLIANTA YLQAR-KTDSDSREL QRRRRSLALPGPQGC AELRQSLSPHFHSLC
OL GRK7 MCDMGGLDNLVANTA YLKAQ---GGDDKEM KKRRRSLSLPKPEQC AALRSTLDKDFESLC
CC GRK7 MCDMGGLDNLVANTA YLKAQ---GGDDKEM KKRRRSLSLPKPEQC VALRESIEKDFTLLC

69087   EQQPIGRRLFRDFLA T-VPTFRKAATFLED VQNWELAEEGPTKDS ALQGLVATCASAPAP
SGK064  EQQPIGRRLFRDFLA T-VPTFRKAATFLED VQNWELAEEGPTKDS ALQGLVATCASAPAP
ST GRK7 EQQPIGRRLFRDFLA T-VPKYSQAVAFLED VQNWELAEEGPAKTS TLQQLAATCARDPGP
OL GRK7 EKQPIGKRFFRQYLD QGGPECNAAAEFLDD LNDWELSEAAAKDKA RTNIINKFCKDGSKS
CC GRK7 ERQPIGKRLFRDFLA N-TPEFKLAAEFLDE LYDWDLAEGAAKDKA RQNIINKYCKPDSKT

69087   GNPQPFLSQAVATKC QAATTEEERVAAVTL RKAEAMAFLQEQPFK DFVTSAFYDKFLQWK
SGK064  GNPQPFLSQAVATKC QAATTEEERVAAVTL AKAEAMAFLQEQPFK DFVTSAFYDKFLQWK
ST GRK7 ---QSFLSQDLATKC RAASTDEERKTLVEQ AKAETMSFLQEQPFQ DFLASPFYDRFLQWK
OL GRK7 S--LTFLTGDVATKC KAVTDKDFEEVMG-Q VKEATKEFLKGKPFT DYQTSEFFEKFLQWK
CC GRK7 F--LTFLSGEPAEKC KSVTDATFEEVMKNK VQDGVREFLKGKPFT EYQGSQYFDKFLQWK

69087   LFEMQPVSDKYFTEF RVLGKGGFGEVCAVQ VKNTGKMYACKKLDK KRLKKKGGEKMALLE
SGK064  LFEMQPVSDKYFTEF RVLGKGGFGEVCAVQ VKNTGKMYACKKLDK KRLKKKGGEKMALLE
ST GkK7 LFEMQPVSDKYFTEF RVLGKGGFGEVCAVQ VRNTGKMYACKKLDK KRLKKKGGEKMALLE
OL GRK7 EYEKQPITEKYFYEF RTLGKGGFGEVCAVQ VKNTGQMYACKKLCK KRLKKKHGEKMALLE
CC GRK7 EYEKQPISDKYFYEF RTLGKGGFGEVCAVQ VKNTGQMYACKKLCK KRLKKKGGEKMALLE
```

Fig. 3A

```
69087   KEILEKVSSPFIVSL AYAFESKTHLCLVMS LMNGGDLKFHIYNVG T------RGLDMSRV
SGK064  KEILEKVSSPFIVSL AYAFESKTHLCLVMS LMNGGDLKFHIYNVG T------RGLDMSRV
ST GRK7 KEILEKVNSPFIVSL AYAFESKTHLCLVMS LMNGGDLKFHIYNVG T------RGLAMSRV
OL GRK7 KKILEKVNSLFIVSL AYAYDTKTHLCLVMS LMNGGDLKYHIYNIG ------EKGIEMERI
CC GRK7 KQILEKVNSLFLVNL AYAYDTKTHLCLVMT LMNGGDLKYHIYNIG YDGKGVDKGIEMKRI

69087   IFYSAQIACGMLHLH ELGIVYRDMKPENVL LDDLGNCRLSDLGLA VEMKGGKPITQRAGT
SGK064  IFYSAQIACGMLHLH ELGIVYRDMKPENGL LDDLGNCRLSDLGLA VEMKGGKPITQRAGT
ST GRK7 IFYTAQMTCGVLHLH GLGIVYRDLKPENVL LDDLGNCRLSDLGLA VEVQDDKPITQRAGT
OL GRK7 IYYTAQITTGMLQLH NMDIVYRDMKPENVL LDSQGQCRLSDLGLA VEIPVGKTTTQKAGT
CC GRK7 IHYTAQITTGILHLH DMDIIYRDMKPENVL LDSQGQCRLSDLGLA IEIAPGKTVTQMAGT

69087   NGYMAPEILMEKVSY SYPVDWFAMGCSIYE MVAGRTPFKD---YK EKVSKEDLKQRTLQD
SGK064  NGYMAPEILMEKVSY SYPVDWFAMGCSIYE MVAGRTPFKD---YK EKVSKEDLKQRTLQD
ST GRK7 NGYMAPEILMDKASY SYPVDWFAMGCSIYE MVAGRTPFKD---FK EKVSKEDLKERTMKD
OL GRK7 GAYMAPEILTETP-Y RTSVDWWALGCSIYE MVAGYTPFKGPEAKK EKVEKEEVQRRIINE
CC GRK7 GAYMAPEILSKTP-Y RTSVDWWALGCSIYE MVAGYTPFKGPESKK EKVEKEEVQRRILNE

69087   EVKFQHDNFTEEAKD ICRLFLAKKPEQRLG SREKSDDPRKHHFFK TINFPRLEAGLIEPP
SGK064  EVKFQHDNFTEEAKD ICRLFLAKKPEQRLR SREKSDDPRKHHFFK TINFPRLEAGLIEPP
ST GRK7 EVAFHHENFTEETKD ICRLFLAKKPEQRLG SREKADDPRKHPFFQ TVNFPRLEAGLVEPP
OL GRK7 EPKFEHKNFNAPTID IIKQFLKKKIDERLG CKG--DDPRKHEWFK SINFARLEAGLIDPP
CC GRK7 EPKWEHKCFDAPTKD VIQQFLKKKIDERLG MRNNMEDPRKHEWFK SINFPRLEAGLVDPP
```

Fig. 3B

```
69087    FVPDPSVVYAKDIAE IDDFSEVRGVEFDDK DKQFFKNFATGAVPI AWQEEIIETGLFEEL
SGK064   FVPDPSVVYAKDIAE IDDFSEVRGVEFDDK DKQFFKNFATGAVPI AWQEEIIETGLFEEL
ST GRK7  FVPDPSVVYAKDVDE IDDFSEVRGVEFDDK DKQFFQRFSTGAVPV AWQEEIIETGLFEEL
OL GRK7  WVPKPNVVYAKDTGD IAEFSEIKGIEFDAK DEKFFKEFSTGAVSI AWQKEMIDTGLFDEL
CC GRK7  WVPKPNVVYAKDTGD IAEFSEIKGIEFDAK DDKFFKEFSTGAVPI QWQQEMIETGLFDEL

69087    NDPNRPTGCEEGNSS K-SGVCLLL
SGK064   NDPNRPTGCEEGNSS K-SGVCLLL
ST GRK7  NDPNRPSGDGKGDSS K-SGVCLLL
OL GRK7  NDPNRKESSGGLDDD KKSGTCTLL
CC GRK7  NDPNRKEGAGGGDDE KKSGTCALL
```

Fig. 3C

```
GGGGCGAAGAGAGGGCTGAACCCGTCCGCTGCCCGGGCGGTGGAGCCCCCACGGCGAGGCGCTGCGCCGGCGGTGGAGA
CTCGCGTTCCCTCCAGCCCCTGGGGCAGAACTTTCTCGCCCCCCCTCCTCCCTCCCCCGCAGTCGGACTCCCTCCCCAG
CCGGCCAGTCCTCCCGGAGGAGAAGGCGCCGCGGAGACAGCCCGGGCGGGGGCCTACCTTCCCCAGGGCAGGCATC

 M   S   A   A   Q   V   S   S   S   R   R   Q   S   C   Y   L   C   D   L   P    20
ATG TCG GCG GCG CAG GTG TCC TCG TCC CGG AGA CAA TCT TGC TAC CTG TGC GAC CTG CCC   60

 R   M   P   W   A   M   I   W   D   F   S   E   P   V   C   R   G   C   V   N    40
CGC ATG CCC TGG GCC ATG ATC TGG GAC TTC TCG GAA CCC GTA TGC CGC GGT TGC GTC AAC  120

 Y   E   G   A   D   R   I   E   F   V   I   E   T   A   R   Q   L   K   R   A    60
TAC GAG GGC GCT GAT CGC ATC GAA TTC GTG ATC GAG ACA GCG CGC CAG CTG AAG CGG GCG  180

 H   G   C   F   P   E   G   R   S   P   P   G   A   A   A   S   A   A   A   K    80
CAC GGC TGC TTC CCG GAG GGT CGC TCC CCA CCC GGC GCC GCG GCC TCG GCC GCC GCC AAG  240

 P   P   P   L   S   A   K   D   I   L   L   Q   Q   Q   Q   Q   L   G   H   G   100
CCG CCG CCG CTC TCC GCC AAG GAC ATC CTT TTG CAG CAG CAG CAG CAG CTT GGC CAC GGC  300

 G   P   E   A   A   P   R   A   P   Q   A   L   E   R   Y   P   L   A   A   A   120
GGC CCC GAG GCG GCC CCG CGC GCG CCG CAG GCC TTG GAG CGC TAC CCG TTG GCG GCC GCG  360

 A   E   R   P   P   R   L   G   S   D   F   G   S   S   R   P   A   A   S   L   140
GCC GAG AGG CCC CCG CGC CTC GGC TCT GAC TTC GGC AGC AGC CGC CCG GCA GCG AGC CTG  420
```

Fig. 4A

```
 A   Q   P   P   T   P   Q   P   P   P   V   N   G   I   L   V   P   N   G   F    160
GCC CAG CCG CCG ACG CCG CAG CCG CCG CCC GTG AAC GGC ATC CTG GTG CCC AAC GGC TTC   480

 S   K   L   E   E   P   P   E   L   N   R   Q   S   P   N   P   R   R   G   H    180
TCC AAG CTA GAG GAG CCG CCC GAG CTG AAT CGC CAG AGC CCG AAC CCG CGG CGC GGC CAC   540

 A   V   P   P   T   L   V   P   L   M   N   G   S   A   T   P   A   A   A   S    200
GCG GTG CCG CCC ACC CTG GTG CCG CTC ATG AAC GGC TCG GCC ACG CCG GCG GCC GCC AGC   600

 L   G   S   A   Q   P   T   D   L   G   A   H   K   R   P   A   S   V   S   S    220
CTG GGC TCC GCG CAG CCC ACC GAT CTG GGC GCC CAC AAG CGG CCG GCA TCC GTG TCG AGC   660

 S   A   A   V   E   H   E   Q   R   E   A   A   A   K   E   K   Q   P   P   P    240
AGC GCT GCC GTG GAG CAC GAG CAG CGT GAG GCG GCA GCC AAG GAG AAA CAA CCG CCG CCG   720

 P   A   H   R   G   P   A   D   S   L   S   T   A   A   G   A   A   E   L   S    260
CCT GCG CAC CGG GGC CCG GCC GAC AGC CTG TCC ACC GCG GCC GGG GCC GCC GAG CTG AGC   780

 A   E   G   A   G   K   S   R   G   S   G   E   Q   D   W   V   N   R   P   K    280
GCG GAA GGT GCG GGC AAG AGC CGC GGG TCT GGA GAG CAG GAC TGG GTC AAC AGG CCC AAG   840

 T   V   R   D   T   L   L   A   L   H   Q   H   G   H   S   G   P   F   E   S    300
ACC GTG CGC GAC ACG CTG CTG GCG CTG CAC CAG CAC GGC CAC TCG GGG CCC TTC GAG AGC   900
```

Fig. 4B

```
K   F   K   K   E   P   A   L   T   A   G   R   L   L   G   F   E   A   N   G    320
AAG TTT AAG AAG GAG CCG GCC CTG ACT GCA GGC AGG TTG TTG GGT TTC GAG GCC AAC GGG  960

A   N   G   S   K   A   V   A   R   T   A   R   K   R   K   P   S   P   E   P    340
GCC AAC GGG TCT AAA GCA GTT GCA AGA ACA GCA AGG AAA AGG AAG CCC TCT CCA GAA CCA 1020

E   G   E   V   G   P   P   K   I   N   G   E   A   Q   P   W   L   S   T   S    360
GAA GGT GAA GTC GGG CCC CCT AAG ATC AAC GGA GAG GCC CAG CCG TGG CTG TCC ACA TCC 1080

T   E   G   L   K   I   P   M   T   P   T   S   S   F   V   S   P   P   P   P    380
ACA GAG GGG CTC AAG ATC CCC ATG ACT CCT ACA TCC TCT TTT GTG TCT CCG CCA CCA CCC 1140

T   A   S   P   H   S   N   R   T   T   P   P   E   A   A   Q   N   G   Q   S    400
ACT GCC TCA CCT CAT TCC AAC CGG ACC ACA CCG CCT GAA GCG GCC CAG AAT GGC CAG TCC 1200

P   M   A   A   L   I   L   V   A   D   N   A   G   G   S   H   A   S   K   D    420
CCC ATG GCA GCC CTG ATC TTA GTA GCA GAC AAT GCA GGG GGC AGT CAT GCC TCA AAA GAT 1260

A   N   Q   V   H   S   T   T   R   R   N   S   N   S   P   P   S   P   S   S    440
GCC AAC CAG GTT CAC TCC ACT ACC AGG AGG AAT AGC AAC AGT CCG CCC TCT CCG TCC TCT 1320

M   N   Q   R   R   L   G   P   R   E   V   G   G   Q   G   A   G   N   T   G    460
ATG AAC CAA AGA AGG CTG GGC CCC AGA GAG GTG GGG GGC CAG GGA GCA GGC AAC ACA GGA 1380
```

Fig. 4C

```
 G   L   E   P   V   H   P   A   S   L   P   D   S   S   L   A   T   S   A   P   480
GGA CTG GAG CCA GTG CAC CCT GCC AGC CTC CCG GAC TCC TCT CTG GCA ACC AGT GCC CCG 1440

 L   C   C   T   L   C   H   E   R   L   E   D   T   H   F   V   Q   C   P   S   500
CTG TGC TGC ACC CTC TGC CAC GAG CGG CTG GAG GAC ACC CAT TTT GTG CAG TGC CCG TCC 1500

 V   P   S   H   K   F   C   F   P   C   S   R   Q   S   I   K   Q   Q   G   A   520
GTC CCT TCG CAC AAG TTC TGC TTC CCT TGC TCC AGA CAA AGC ATC AAA CAG CAG GGA GCT 1560

 S   G   E   V   Y   C   P   S   G   E   K   C   P   L   V   G   S   N   V   P   540
AGT GGA GAG GTC TAT TGT CCC AGT GGG GAA AAA TGC CCT CTT GTG GGC TCC AAT GTC CCC 1620

 W   A   F   M   Q   G   E   I   A   T   I   L   A   G   D   V   K   V   K   K   560
TGG GCC TTT ATG CAA GGG GAA ATT GCA ACC ATC CTT GCT GGA GAT GTG AAA GTG AAA AAA 1680

 E   R   D   S   *                                                               564
GAG AGA GAC TCG TGA                                                             1695

CTTTTCCGGTTTCAGAAAAACCCAATGATTACCCTTAATTAAAACTGCTTGAATTGTATATATATCTCCATATATATAT
ATATCCAAGACAAGGGAAATGTAGACTTCATAAACATGGCTGTATAATTTTGATTTTTTTTGAATACATTGTGTTTCTA
TATTTTTTTTGACGACAAAAGGTATGTACTTATAAAGACATTTTTTTCTTTTGTTAACGTTATTAGCATATCTTTGTGC
TTTATTATCCTGGTGACAGTTACCGTTCTATGTAGGCTGTGACTTGCGCTGCTTTTTTAGAGCACTTGGCAAATCAGAA
ATGCTTCTAGCTGTATTTGTATGCACTTATTTTAAAAAGAAAAAAAAAAGCCAAATACATTTTCTGAACTTTTGTAAGAT
TGCCTTACTGTCTGTCATTCCTTATTGCTGGCCCCTTTCTCAGGCCGGAGGCCAAGTGGTGGAGAAGGAAAGGAAATGA
```

Fig. 4D

TCGAACGGGCATGTTGTCAAGTGGGCATGCCACTGGGAAATACCACCAGTTTACCCTGAAACATTGTCCTCAGAGGAGT
AGGAAAGTGGATTTTGAATCTCTATTTTGCTCAAAAGTTCAGTTCCTGAGATACTGATGACTGAGAGTGCTGCTGGGAA
ATTTTCAGGATTGTGTGGTCTTTTGGGGTTTTTTGTTTTTTTTTTTTTAAGACAAAGTTGACCGCTGTTCACTGTCCAC
GTGATCAGTTGTAAGATTACAATGCTGCATGCTAGTTGGTTACATAAGATACAATTCCAGTGATGGAAGGCGGTTATAA
TGGATGGTGGTGTGTACAAGATGGCACTGCCATCTTTGAGCAGAGCCCAGCTCTGCAGCGCCACTTCATCTTTTTAAAC
ACCCTAGAGGTCTGTTTGTTGTTGCTGTTGTCCTTTATTTTGAAAGAGTTGCAAGAGAAGTTACAGTCCAGGTGAACTT
GGAGATTGTGGGATTGGTTTTGTTTCTGTTTTGTTTTGTTTATCATTTACCTGTAGTGCTATTGCTGTTGATACTATCA
CCTATACCCTGTTTCTAGTGAGTGCTGAATACAGTATGGTACAATGA

Fig. 4E

```
15821      MSAAQVSSSRRQSCY  LCDLPRMPWAMIWDF  SEPVCRGCVNYEGAD  RIEFVIETARQLKRA
C14orf4    MSAAQVSSSRRQSCY  LCDLPRMPWAMIWDF  SEPVCRGCVNYEGAD  RIEFVIETARQLKRA
KIAA1865   ---------------  ---------------  ---------------  ---------------

15821      HG-------------  CFPEGRSPPGAAASA  AAKPPPLSAKDILLQ  QQQQLGHGGPEAAPR
C14orf4    HGCFQDGRSPGPPPP  VGVKTVALSAKEAAA  AAAAAAAAAAAAQQQ  QQQQQQQQQQQQQQQ
KIAA1865   -------------SH  RIRDRDSAPAEAGAR  LLPGRPLPRAAAAAQ  QQQQQQQQQQQQQQQ

15821      APQALERYPLAAAAE  RPPRLGSDFGSSRP-  ------------AAS  LAQPPTPQPPP----
C14orf4    QQQQQQQLNHVDGSS  KPAVLAAPSGLERYG  LSAAAAAAAAAAAAV  EQRSRFEYPPPPVSL
KIAA1865   QQQQQQQLNHVDGSS  KPAVLAAPSGLERYG  LSAAAAAAAAAAAAV  EQRSRFEYPPPPVSL

15821      ---------VNGILV  PNGFSK---LEEPPE  LNRQSPNP-------  ---------------
C14orf4    GSSSHTARLPNGLGG  PNGFPKPTPEEGPPE  LNRQSPNSSSAAASV  ASRRGTHGGLVTGLP
KIAA1865   GSSSHTARLPNGLGG  PNGFPKPTPEEGPPE  LNRQSPNSSSAAASV  ASRRGTHGGLVTGLP

15821      ---RRG---HAVPPT  LVPLMNGSATPAAAS  LGSAQPTDLG-----  ------AHKRP--AS
C14orf4    NPGGGGGPQLTVPPN  LLPQTLLNGPASAAV  LPPPPPHALGSRGPP  TPAPPGAPGGPACLG
KIAA1865   NPGGGGGPQLTVPPN  LLPQTLLNGPASAAV  LPPPPPHALGSRGPP  TPAPPGAPGGPACLG
```

FIG 6A

```
15821      -----------VSSS  AAVEHEQREAAAKEK  QPPPPAHRGPADSLS  TAAGAAELSAEGAGK
C14orf4    GTPGVSATSSSASSS  TSSSVAEVGVGAGGK  RPGSVSSTDQERELK  EKQRNAEALAELSES
KIAA1865   GTPGVSATSSSASSS  TSSSVAEVGVGAGGK  RPGSVSSTDQERELK  EKQRNAEALAELSES

15821      SRGSGEQDWVNRPKT  VRDTLLALH------  ---------------  ---------------
C14orf4    LRN-RAEEWASKPKM  VRDTLLTLAGCTPYE  VRFKKDHSLLGRVFA  FDAVSKPGMDYELKL
KIAA1865   LRN-RAEEWASKPKM  VRDTLLTLAGCTPYE  VRFKKDHSLLGRVFA  FDAVSKPGMDYELKL

15821      ---------------  ---------------  ---------------  --------QHGHSGP
C14orf4    FIEYPTGSGNVYSSA  SGVAKQMYQDCMKDF  GRGLSSGFKYLEYEK  KHGSGDWRLLGDLLP
KIAA1865   FIEYPTGSGNVYSSA  SGVAKQMYQDCMKDF  GRGLSSGFKYLEYEK  KHGSGDWRLLGDLLP

15821      FESKFKKE-------  ----------P----  -------ALTAGRLL  GFEANGANGSKAVAR
C14orf4    EAVRFFKEGVPGADM  LPQPYLDASCPMLPT  ALVSLSRAPSAPPGT  GALPPAAPSGRGAAA
KIAA1865   EAVRFFKEGVPGADM  LPQPYLDASCPMLPT  ALVSLSRAPSAPPGT  GALPPAAPSGRGAAA

15821      TARKRKPSPEPEGEV  GPPKINGEAQP---W  LSTSTEGLKIPMTPT  SSFVS--------PP
C14orf4    SLRKRKASPEPPDSA  EGALKLGEEQQRQQW  MANQSEALKLTMSAG  GFAAPGHAAGGPPPP
KIAA1865   SLRKRKASPEPPDSA  EGALKLGEEQQRQQW  MANQSEALKLTMSAG  GFAAPGHAAGGPPPP
```

FIG. 6B

```
15821      PPTASPHSNRTTPPE   AAQ-NGQSPMAALIL   VADNAGGSHASKDAN   QVHSTTR--R-NSNS
C14orf4    PPPLGPHSNRTTPPE   SAPQNGPSPMAALMS   VADTLGTAHSPKDGS   SVHSTTASARRNSSS
KIAA1865   PPPLGPHSNRTTPPE   SAPQNGPSPMAALMS   VADTLGTAHSPKDGS   SVHSTTASARRNSSS

15821      PPSPSSMN-QRRLGP   R------EVGGQGAG   NTGGLEPVHPASLPD   SSLATSAPLCCTLCH
C14orf4    PVSPASVPGQRRLAS   RNGDLNLQVAPPPPS   AHPGMDQVHPQNIPD   SPMANSGPLCCTICH
KIAA1865   PVSPASVPGQRRLAS   RNGDLNLQVAPPPPS   AHPGMDQVHPQNIPD   SPMANSGPLCCTICH

15821      ERLEDTHFVQCPSVP   SHKFCFPCSRQSIKQ   QGASGEVYCPSGEKC   PLVGSNVPWAFMQGE
C14orf4    ERLEDTHFVQCPSVP   SHKFCFPCSRESIKA   QGATGEVYCPSGEKC   PLVGSNVPWAFMQGE
KIAA1865   ERLEDTHFVQCPSVP   SHKFCFPCSRESIKA   QGATGEVYCPSGEKC   PLVGSNVPWAFMQGE

15821      IATILAGDVKVKKER   DS
C14orf4    IATILAGDVKVKKER   DP
KIAA1865   IATILAGDVKVKKER   DP
```

FIG. 6C

```
15821      GFEANGANGSKAVAR  TARKRKPSPEPEGEV  GPPKINGEAQP---W  LSTSTEGLKIPMTPT
C14orf4    GALPPAAPSGRGAAA  SLRKRKASPEPPDSA  EGALKLGEEQQRQQW  MANQSEALKLTMSAG
KIAA1865   GALPPAAPSGRGAAA  SLRKRKASPEPPDSA  EGALKLGEEQQRQQW  MANQSEALKLTMSAG
736        ------------VAR  TARKRKPSPEPEGEV  GPPKINGEAQP---W  XSTSTEGXKIPMTPT
HTRM       ---------------  ---------------  ---------------  -----------MTPT
dn740_3    ---------------  ---------------  ---------------  -----------MTPT
Unnamed    ---------------  ---------------  ---------------  -----------MSAG

15821      SSFVS--------PP  PPTASPHSNRTTPPE  AAQ-NGQSPMAALIL  VADNAGGSHASKDAN
C14orf4    GFAAPGHAAGGPPPP  PPPLGPHSNRTTPPE  SAPQNGPSPMAALMS  VADTLGTAHSPKDGS
KIAA1865   GFAAPGHAAGGPPPP  PPPLGPHSNRTTPPE  SAPQNGPSPMAALMS  VADTLGTAHSPKDGS
736        SSFVS--------PP  PPTASPHSNRTTPPE  AAQ-NGQSPMAALIL  VADNAGGSHASKDAN
HTRM       SSFVS--------PP  PPTASPHSNRTTPPE  AAQ-NGQSPMAALIL  VADNAGGSHASKDAN
dn740_3    SSFVS--------PP  PPTASPHSNRTTPPE  AAQ-NGQSPMAALIL  VADNAGGSHASKDAN
Unnamed    GFAAPGHAAGGPPPP  PPPLGPHSNRTTPPE  SAPQNGPSPMAALMS  VADTLGTAHSPKDGS

15821      QVHSTTR--R-NSNS  PPSPSSMN-QRRLGP  R------EVGGQGAG  NTGGLEPVHPASLPD
C14orf4    SVHSTTASARRNSSS  PVSPASVPGQRRLAS  RNGDLNLQVAPPPPS  AHPGMDQVHPQNIPD
KIAA1865   SVHSTTASARRNSSS  PVSPASVPGQRRLAS  RNGDLNLQVAPPPPS  AHPGMDQVHPQNIPD
736        QVHSTTRR---NSNS  PPSPSSMN-QRRLGP  R------EVGGQGAG  NTGGLEPVHPASLPD
HTRM       QVHSTTRR---NSNS  PPSPSSMN-QRRLGP  R------EVGGQGAG  NTGGLEPVHPASLPD
dn740_3    QVHSTTRR---NSNS  PPSPSSMN-QRRLGP  R------EVGGQGAG  NTGGLEPVHPASLPD
Unnamed    SVHSTTASARRNSSS  PVSPASVPGQRRLAS  RNGDLNLQVAPPPPS  AHPGMDQVHPQNIPD
```

FIG. 7A

```
15821      SSLATSAPLCCTLCH  ERLEDTHFVQCPSVP  SHKFCFPCSRQSIKQ  QGASGEVYCPSGEKC
C14orf4    SPMANSGPLCCTICH  ERLEDTHFVQCPSVP  SHKFCFPCSRESIKA  QGATGEVYCPSGEKC
KIAA1865   SPMANSGPLCCTICH  ERLEDTHFVQCPSVP  SHKFCFPCSRESIKA  QGATGEVYCPSGEKC
736        FSLATSAPLCCTLCH  ERLEDNHFVQC----  ---------------  ---------------
HTRM       SSLATSAPLCCTLCH  ERLEDTHFVQCPSVP  SHKFCFPCSRQSIKQ  QGASGEVYCPSGEKC
dn740_3    SSLATSAPLCCTLCH  ERLEDTHFVQCPSVP  SHKFCFPCSRQSIKQ  QGASGEVYCPSGEKC
Unnamed    SPMANSGPLCCTICH  ERLEDTHFVQCPSVP  SHKFCFPCSRESIKA  QGATGEVYCPSGEKC

15821      PLVGSNVPWAFMQGE  IATILAGDVKVKKER  DS
C14orf4    PLVGSNVPWAFMQGE  IATILAGDVKVKKER  DP
KIAA1865   PLVGSNVPWAFMQGE  IATILAGDVKVKKER  DP
736        ---------------  ---------------  --
HTRM       PLVGSNVPWAFMQGE  IATILAGDVKVKKER  DS
dn740_3    PLVGSNVPWAFMQGE  IATILAGDVKVKKER  DS
Unnamed    PLVGSNVPWAFMQGE  IATILAGDVKVKKER  DP
```

FIG. 7B

```
GTCGACCACGCGTCCGGGAGACAGAAAGAGGGTGGTGGCCGATAGCTGGTCCTCTTTCTCCAACACCTAGCCTGAGACT
TGGCGGCGCGGCTGCTATCCTGAACTAGCTTGGTAAGTGTTGTGTCCCGAACCAGCGTAGAGAGACCTCGGACCAGCCG

        M   T   A   S   A   S   S   F   S   S   S   Q   G   V   Q   Q   P   S        18
CCTTG ATG ACA GCA TCC GCG TCC TCC TTT TCA TCA TCT CAG GGT GTC CAG CAG CCC TCC       54

 I   Y   S   F   S   Q   I   T   R   S   L   F   L   S   N   G   V   A   A   N      38
ATC TAC AGC TTC TCC CAA ATA ACC AGA AGC TTG TTT CTC AGC AAT GGT GTG GCC GCC AAC    114

 D   K   L   L   L   S   S   N   R   I   T   A   I   V   N   A   S   V   E   V      58
GAC AAA CTC CTT CTG TCC AGC AAT CGC ATC ACC GCC ATT GTC AAT GCC TCG GTG GAA GTG    174

 V   N   V   F   F   E   G   I   Q   Y   I   K   V   P   V   T   D   A   R   D      78
GTC AAC GTA TTC TTC GAG GGC ATT CAG TAC ATA AAG GTG CCT GTT ACC GAT GCT CGT GAC    234

 S   R   L   Y   D   F   F   D   P   I   A   D   L   I   H   T   I   D   M   R      98
TCG CGT CTC TAC GAC TTT TTT GAC CCC ATT GCT GAT CTT ATC CAC ACC ATC GAT ATG AGG    294

 Q   G   R   T   L   L   H   C   M   A   G   V   S   R   S   A   S   L   C   L     118
CAG GGC CGT ACG CTG CTG CAC TGC ATG GCT GGA GTG AGC CGT TCC GCC TCA CTG TGC CTT    354

 A   Y   L   M   K   Y   H   S   M   S   L   L   D   A   H   T   W   T   K   S     138
GCG TAC CTC ATG AAA TAC CAC TCC ATG TCG CTG CTG GAC GCC CAT ACA TGG ACC AAG TCG    414
```

Fig. 8A

```
 R   R   P   I   I   R   P   N   N   G   F   W   E   Q   L   I   N   Y   E   F   158
CGC CGC CCC ATC ATC CGG CCC AAC AAC GGC TTT TGG GAA CAG CTC ATC AAT TAC GAA TTC  474

 K   L   F   N   N   N   T   V   R   M   I   N   S   P   V   G   N   I   P   D   178
AAG CTG TTT AAT AAC AAC ACC GTG CGC ATG ATC AAC TCG CCG GTA GGT AAC ATC CCT GAC  534

 I   Y   E   K   D   L   R   T   M   I   S   M   *                               190
ATC TAT GAG AAG GAC CTA CGT ACG ATG ATA TCA ATG TAA                              573

GCCATCCCGGCCAGCCCCTGACATCTGCCATCGATCTTGCACCAAGACTGAACTTGAACACTGACATTTTGTTAGTAAA
GAAAACCGGATGGTGCCTTGTTAAAGGGCAAGAAAAAAGGGAGGGGGTTGGAGTTTTGAACGTAGTAAGCCTTACCTTA
ATAGAATTAAATTCATGAAACATAAAACA
```

Fig. 8B

```
15814    1 MTASASSFSSSQGVQQPSIYSFSQITRSLFLSNGVAANDKLLLSSNRITAIVNASVEVVN 60
           ||||||||||||||||||||||||||||||||||||||||||||||||||||||||||||
DSP-8    1 MTASASSFSSSQGVQQPSIYSFSQITRSLFLSNGVAANDKLLLSSNRITAIVNASVEVVN 60

15814   61 VFFEGIQYIKVPVTDARDSRLYDFFDPIADLIHTIDMRQGRTLLHCMAGVSRSASLCLAY 120
           ||||||||||||||||||||||||||||||||||||||||||||||||||||||||||||
DSP-8   61 VFFEGIQYIKVPVTDARDSRLYDFFDPIADLIHTIDMRQGRTLLHCMAGVSRSASLCLAY 120

15814  121 LMKYHSMSLLDAHTWTKSRRPIIRPNNGFWEQLINYEFKLFNNNTVRMINSPVGNIPDIY 180
           ||||||||||||||||||||||||||||||||||||||||||||||||||||||||||||
DSP-8  121 LMKYHSMSLLDAHTWTKSRRPIIRPNNGFWEQLINYEFKLFNNNTVRMINSPVGNIPDIY 180

15814  181 EKDLRTMISM 190
           ||||| ||||
DSP-8  181 EKDLRMMISM 190
```

Fig. 10

METHODS AND COMPOSITIONS OF HUMAN 69087 NUCLEIC ACIDS AND USES THEREOF

CROSS-REFERENCE TO RELATED APPLICATIONS

This application is entitled to priority pursuant to 35 U.S.C. §119(e) to U.S. provisional patent application 60/242,428 which was filed on Oct. 23, 2000.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

G Protein Coupled Receptors

G proteins are heterotrimeric proteins which are capable of conveying information from cell surface receptors to internal components of a cell. Those internal components include components regulating gene transcription, protein structure and activity, cell conformation and movement, cell metabolism, nerve impulse transmission, cardiac function, olfaction, vision, and many other cellular processes that are responsive to external stimuli. The cell surface receptors that sense extracellular compounds or conditions and convey this signal to G protein include a class of integral membrane proteins commonly designated G protein coupled receptors (GPCRs). Crudely summarized, GPCRs exist in one of two states—active and inactive (see, e.g., Gether et al., 1998, J. Biol. Chem. 273:17979–17982).

In its active state, a GPCR is able to interact with a G protein and activate that G protein (by promoting exchange of GTP in place of GDP on the alpha subunit of the G protein and subsequent dissociation of the alpha subunit from the beta and gamma subunits of the G protein). In many instances, time-dependent decrease of the cellular response to an external signal normally detected by a GPCR/G protein pair occurs, despite the continued presence of the signaling ligand or condition. This attenuation of GPCR-/G protein-mediated signaling is commonly designated desensitization, and has well recognized importance in physiological and pharmacological settings.

One mechanism by which GPCR desensitization can occur is commonly referred to as homologous desensitization (i.e., desensitization of only an activated GPCR, rather than others) and involves phosphorylation of the GPCR by an enzyme of the class generally known as GPCR kinases (GPCRKs). GPCRK-catalyzed phosphorylation of an activated GPCR can inhibit signaling mediated by the GPCR, and also promotes association of the phosphorylated GPCR with an arrestin protein. Arrestin binding prevents association of a GPCR with its corresponding G protein, halting signaling. Arrestin binding also promotes internalization and sequestration of the GPCR, leading to long-term desensitization of the GPCR.

Numerous GPCRKs have been described, and many more are believed to exist. In view of the widespread and critical nature of GPCRK activities in normal and pathological physiological processes, a need exists for identification of further members of this protein family. The present invention satisfies this need by providing a novel human GPCRK, designated 69087.

Nuclear Signaling Proteins

Regulation of gene transcription in eukaryotic cells in response to cellular stimuli (e.g., cell cycle or nutritional state indicators) or environmental stimuli (e.g., heat, presence of an attractant, or presence of a surface such as that of a neighboring cell) requires transduction of a signal across the nuclear membrane and interaction of a protein with the gene.

A significant mechanism by which nuclear transmembrane signaling can occur is by alteration of the structure of a nuclear transmembrane protein. Such alteration can be effected by binding of a ligand (e.g., a protein, a hormone, or a steroid) with the nuclear transmembrane protein on the cytoplasmic face of the nuclear membrane. Following binding of the ligand with the protein, the conformation of the protein is altered on the nuclear face of the nuclear membrane, thereby altering the properties exerted by the nuclear transmembrane protein on the contents of the nucleus. By way of example, ligand-bound nuclear membrane protein can be able to bind with a nuclear protein that is not able to bind with the non-ligand-bound form of the nuclear membrane protein (or the reverse).

Intranuclear signaling can occur by interaction of a protein with another protein (e.g., a DNA-associated protein, a component of the transcriptional apparatus, or a nuclear transmembrane signaling protein), with a nucleic acid, or with both. A variety of intranuclear signaling proteins are known in humans, including, for example, transcription factors, enhancers and repressors of transcription, recombination-modulating proteins, and modulators of these proteins.

Nuclear transmembrane signaling and intranuclear signaling (individually and collectively designated "nuclear signaling" in this disclosure) are involved in a variety of physiological and pathophysiological processes. For example, nuclear signaling can enhance or inhibit expression of a gene in response to the occurrence or presence of an environmental stimulus. Nuclear signaling can also mediate interconnections between cytoskeletal components and the nuclear membrane or a component of the nuclear contents (e.g., with a centromere or with a particular region of a chromosome). Interaction of a nuclear signaling protein with a cytoplasmic or nuclear component can also modulate the properties of the nuclear membrane (e.g., the porosity of the membrane or the ability of a particular compound to traverse the membrane).

Numerous nuclear signaling proteins have been described, and many more are believed to exist. In view of the widespread and critical nature of nuclear signaling protein activities in normal and pathological physiological processes, a need exists for identification of further nuclear signaling proteins. The present invention satisfies this need by providing a novel human nuclear signaling protein, designated 15821.

Mitogen-Activated Protein Kinase Phosphatases

Protein phosphorylation, for example at serine, threonine, and tyrosine residues, is a key regulatory mechanism for a variety of cellular processes. For example, protein phosphorylation is involved in regulation of cell growth and differentiation, entry of cells into the cell cycle and their progression through the cell cycle, mitogenesis, cell motility, cell-to-cell interactions, cell metabolism, gene transcription, expression of normal and aberrant immune responses. The extent of protein phosphorylation influences cell signaling processes, including those signaling processes mediated by G proteins and their corresponding receptors.

Protein phosphorylation is influenced primarily by enzymes of two types, namely protein kinases (PKs) and protein phosphatases (PPs). PKs catalyze addition of a phosphate moiety to a protein amino acid residue (generally a serine, threonine, or tyrosine residue), and PPs catalyze removal of such moieties. The catalytic activities of PKs and PPs are, in turn, influenced by the state of the cell and the environment in which it finds itself.

Phosphorylation of amino acid residues by a PK generally manifests itself in the form of faster cell growth, metabolism, or division, as greater cell motility, or in the form of higher gene transcription, although certain physiological processes are inhibited by protein phosphorylation. De-phosphorylation of amino acid residues by a PP, by contrast, generally manifests itself as slower (or halted) cell growth, division, or metabolism, as lower cell motility, or in the form of lower gene transcription. PK/PP-modulated protein phosphorylation is also involved in carcinogenesis.

Among the PKs that have been described are a class of PKs alternatively designated mitogen-activated protein kinases, MAP kinases, MAPKs, extracellular signal-regulated protein kinases, and ERKs. MAP kinases are the terminal enzyme in a three-kinase cascade. MAPKs are activated by phosphorylation catalyzed by MAPK kinase enzymes (MAPKKs), which in turn are activated by phosphorylation catalyzed by MAPKK kinase enzymes (MAPKKKs). Ability of a cell to activate a variety of MAPKs permits the cell to respond to a variety of extracellular signals with a physiological response that is appropriate for the state of the cell. A single MAPK enzyme can phosphorylate multiple other proteins within the cell, including, for example, other PKs, transcription factors, cytoskeletal proteins, and other enzymes. De-phosphorylation of MAPKs is a significant aspect of cell signaling, and is catalyzed by proteins designated MAPK phosphatases (MAPKPs). The phosphorylation state of MAPKs can be regulated in a cell by the opposing actions of MAPKKs and MAPKPs.

In view of the widespread and critical nature of MAPK-mediated signaling, and the corresponding significance of MAPKP activities in normal and pathological physiological processes, a need exists for identification of further members of the MAPKP protein family. The present invention satisfies this need by providing a novel human MAPKP designated 15418.

BRIEF SUMMARY OF THE INVENTION

The present invention is based, in part, on the discovery three genes and functions and uses of those genes.

The first gene is a novel gene encoding a GPCRK, the gene being referred to herein as "69087." The nucleotide sequence of a cDNA encoding 69087 is shown in SEQ ID NO: 1, the nucleotide sequence of the coding region being SEQ ID NO: 3, and the amino acid sequence of a 69087 polypeptide is shown in SEQ ID NO: 2.

The second gene is a novel gene encoding a nuclear signaling protein, the gene being referred to herein as "15821." The nucleotide sequence of a cDNA encoding 15821 is shown in SEQ ID NO: 21, the nucleotide sequence of the coding region being SEQ ID NO: 23, and the amino acid sequence of a 15821 polypeptide is shown in SEQ ID NO: 22.

The third gene encodes a MAPKP, and the gene is referred to herein as "15418." The nucleotide sequence of a cDNA encoding 15418 is shown in SEQ ID NO: 41, the nucleotide sequence of the coding region being SEQ ID NO: 43, and the amino acid sequence of a 15418 polypeptide is shown in SEQ ID NO: 42.

Accordingly, in one aspect, the invention features a nucleic acid molecule that encodes a 69087, 15821, or 15418 protein or polypeptide, e.g., a biologically active portion of the 69087, 15821, or 15418 protein. In a preferred embodiment the isolated nucleic acid molecule encodes a polypeptide having the amino acid sequence of one of SEQ ID NOs: 2, 22, and 42. In other embodiments, the invention provides isolated 69087, 15821, or 15418 nucleic acid molecules having the nucleotide sequence of one of SEQ ID NOs: 1, 3, 21, 23, 41, and 43.

In still other embodiments, the invention provides nucleic acid molecules that have sequences that are substantially identical (e.g., naturally occurring allelic variants) to the nucleotide sequence of one of SEQ ID NOs: 1, 3, 21, 23, 41, and 43 and which preferably exhibit an activity characteristic of the corresponding protein. In other embodiments, the invention provides a nucleic acid molecule which hybridizes under stringent hybridization conditions with a nucleic acid molecule having a sequence comprising the nucleotide sequence of one of SEQ ID NOs: 1, 3, 21, 23, 41, and 43, wherein the nucleic acid encodes a full length 69087, 15821, or 15418 protein or an active fragment of one of these.

In a related aspect, the invention further provides nucleic acid constructs that include a 69087, 15821, or 15418 nucleic acid molecule described herein. In certain embodiments, the nucleic acid molecules of the invention are operatively linked to native or heterologous regulatory sequences. Also included are vectors and host cells containing the 69087, 15821, or 15418 nucleic acid molecules of the invention, e.g., vectors and host cells suitable for producing 69087, 15821, or 15418 nucleic acid molecules and polypeptides.

In another related aspect, the invention provides nucleic acid fragments suitable as primers or hybridization probes for detection of 69087-encoding, 15821-encoding, or 15418-encoding nucleic acids.

In still another related aspect, isolated nucleic acid molecules that are antisense to a 69087-encoding, 15821-encoding, or 15418-encoding nucleic acid molecule are provided.

In another aspect, the invention includes 69087, 15821, or 15418 polypeptides, and biologically active or antigenic fragments thereof that are useful, e.g., as reagents or targets in assays applicable to treatment and diagnosis of 69087-mediated or related disorders (e.g., GPCRK-mediated disorders such as those described herein), 15821-mediated or related disorders (e.g., disorders related to aberrant nuclear or cell signaling protein function, such as those described herein), and 15418-mediated or related disorders (e.g., MAPKP-mediated disorders such as those described herein).

In another embodiment, the invention provides 69087 polypeptides having G protein coupled receptor kinase activity. Preferred polypeptides are 69087 proteins including at least one pkinase domain, and preferably having a 69087 activity, e.g., a 69087 activity as described herein. Preferred polypeptides are 69087 proteins including at least one RGS domain and at least one pkinase domain.

In another embodiment, the invention provides 15821 polypeptides which are localized in the nucleus or in the nuclear membrane when expressed. In yet another embodiment, the invention provides 15821 polypeptides which exhibit the ability to modulate expression of one or more genes, either constitutively or in response to an environmental or cellular stimulus. Preferred polypeptides are 15821 proteins including at least one C3HC4 type zinc finger (RING finger) domain, and preferably having a 15821 activity, e.g., a 15821 activity as described herein. Preferred polypeptides are 15821 proteins including at least one transmembrane domain and at least one RING finger domain.

In still another embodiment, the invention provides 15418 polypeptides having protein phosphatase activity (e.g., MAPKP activity). Preferred polypeptides are 15418 proteins including at least one DSPc domain or at least one tyrosine specific protein phosphatase active site, and preferably having a 15418 activity, e.g., a 15418 activity as described herein. Preferred polypeptides are 15418 proteins including at least one DSPc domain and at least one tyrosine specific protein phosphatase active site.

In other embodiments, the invention provides 69087, 15821, and 15418 polypeptides, e.g., a 69087, 15821, or 15418 polypeptide having the amino acid sequence shown in one of SEQ ID NOs: 2, 22, and 42, an amino acid sequence that is substantially identical to the amino acid sequence shown in one of SEQ ID NOs: 2, 22, and 42; or an amino acid sequence encoded by a nucleic acid molecule having a nucleotide sequence which hybridizes under stringent hybridization conditions to a nucleic acid molecule comprising the nucleotide sequence of any of SEQ ID NOs: 1, 3, 21, 23, 41, and 43, wherein the nucleic acid encodes a full length 69087, 15821, or 15418 protein or an active fragment of one of these.

In a related aspect, the invention further provides nucleic acid constructs that include a 69087, 15821, or 15418 nucleic acid molecule described herein.

In a related aspect, the invention provides 69087, 15821, or 15418 polypeptides or fragments operatively linked to non-69087, non-15821, or non-15418 polypeptides to form fusion proteins.

In another aspect, the invention features antibodies and antigen-binding fragments thereof, that react with, or more preferably, specifically bind, 69087, 15821, or 15418 polypeptides.

In another aspect, the invention provides methods of screening for compounds that modulate the expression or activity of the 69087, 15821, or 15418 polypeptides or nucleic acids.

In still another aspect, the invention provides a process for modulating 69087, 15821, or 15418 polypeptide or nucleic acid expression or activity, e.g., using the screened compounds. In certain embodiments, the methods involve treatment of conditions related to aberrant activity or expression of the 69087, 15821, or 15418 polypeptides or nucleic acids, such as conditions involving, for 69087, aberrant or deficient protein phosphorylation or aberrant or deficient cell process regulation (e.g., aberrant or deficient cell signaling or aberrant or inadequately-suppressed tumorigenesis), for 15821, aberrant or deficient gene expression or aberrant or deficient nuclear membrane function (e.g., aberrant or deficient nuclear membrane permeability or aberrant or deficient nuclear transmembrane signaling), or for 15418, aberrant or supra-physiological protein phosphorylation (e.g., aberrant or deficient MAPKP activity) or aberrant or deficient cell process regulation (e.g., aberrant or deficient cell signaling or aberrant or inadequately-suppressed tumorigenesis).

The invention also provides assays for determining the activity of or the presence or absence of 69087, 15821, or 15418 polypeptides or nucleic acid molecules in a biological sample, including for disease diagnosis.

In further aspect the invention provides assays for determining the presence or absence of a genetic alteration in a 69087, 15821, or 15418 polypeptide or nucleic acid molecule, including for disease diagnosis.

The invention includes a method of modulating the ability of a cell to affect the phosphorylation state of a G protein-coupled receptor. The method comprises modulating the activity of 69087 protein in the cell. The activity of 69087 protein can be modulated by inhibiting expression of the 69087 gene in the cell, for example by administering to the cell an antisense oligonucleotide which hybridizes under stringent conditions with a transcript (e.g., an mRNA) of the 69087 gene, an antisense oligonucleotide which hybridizes under stringent conditions with a polynucleotide having the nucleotide sequence SEQ ID NO: 1, or an antisense oligonucleotide which hybridizes under stringent conditions with a polynucleotide having the nucleotide sequence SEQ ID NO: 3. Alternatively the activity of 69087 protein can be inhibited without significantly affecting 69087 gene expression in the cell. For example, the activity of 69087 protein can be inhibited by administering to the cell an agent which inhibits an activity of 69087 protein, such as an antibody which specifically binds with 69087 protein. In a related aspect, the activity of 69087 can be modulated by enhancing expression of 69087 in the cell. For example, expression of 69087 in a cell can be enhanced by administering to the cell an agent that enhances expression of 69087, such as an expression vector encoding 69087 protein.

In another aspect, the invention relates to a method for assessing whether a test compound is useful for modulating at least one phenomenon selected from the group consisting of cell signaling, cell growth, cell differentiation, tumorigenesis, tumor growth, tumor metastasis, cell motility, entry of a cell into the cell cycle, transcription of a gene in a cell, cardiac function, transmission of a nerve impulse, olfactory sensation, photoreceptor signaling, uncoupling of a receptor and a heterotrimeric G-protein, photoreceptor signaling, color vision, night vision, visual pigmentation, and photoreceptor desensitization. The method comprises:

a) adding the test compound to a first composition comprising a polypeptide that has an amino acid sequence at least 90% identical to SEQ ID NO: 2 and that exhibits a 69087 activity and;

b) comparing the 69087 activity in the first composition and in a second composition that is substantially identical to the first composition, except that it lacks the test compound. A difference in the 69087 activity in the first and second compositions is an indication that the test compound is useful for modulating the phenomenon.

The invention also includes a method for assessing whether a test compound is useful for modulating at least one phenomenon selected from the group consisting of cell signaling, cell growth, cell differentiation, tumorigenesis, tumor growth, tumor metastasis, cell motility, entry of a cell into the cell cycle, transcription of a gene in a cell, cardiac function, transmission of a nerve impulse, olfactory sensation, photoreceptor signaling, uncoupling of a receptor and a heterotrimeric G-protein, photoreceptor signaling, color vision, night vision, visual pigmentation, and photoreceptor desensitization. This method comprises:

a) adding the test compound to a composition comprising a cell which comprises a nucleic acid that encodes a polypeptide that has an amino acid sequence at least 90% identical to SEQ ID NO: 2 and exhibits a 69087 activity and;

b) comparing the 69087 activity in the first composition and in a second composition that is substantially identical to the first composition, except that it lacks the test compound. A difference in the 69087 activity in the first and second compositions is an indication that the test compound is useful for modulating the phenomenon.

The invention further relates to a method of making a pharmaceutical composition for modulating at least one phenomenon selected from the group consisting of cell signaling, cell growth, cell differentiation, tumorigenesis, tumor growth, tumor metastasis, cell motility, entry of a cell into the cell cycle, transcription of a gene in a cell, cardiac function, transmission of a nerve impulses, olfactory sensation, photoreceptor signaling, uncoupling of a receptor and a heterotrimeric G-protein, photoreceptor signaling, color vision, night vision, visual pigmentation, and photoreceptor desensitization. The method comprises selecting a test compound useful for modulating the phenomenon as described herein and combining the test compound with a pharmaceutically acceptable carrier in order to make the pharmaceutical composition. This composition can be used to modulate one or more of these phenomena in a human.

The invention includes another method or identifying compounds useful for modulating at least one phenomenon selected from the group consisting of cell signaling, cell growth, cell differentiation, tumorigenesis, tumor growth, tumor metastasis, cell motility, entry of a cell into the cell cycle, transcription of a gene in a cell, cardiac function, transmission of a nerve impulses, olfactory sensation, photoreceptor signaling, uncoupling of a receptor and a heterotrimeric G-protein, photoreceptor signaling, color vision, night vision, visual pigmentation, and photoreceptor desensitization. This method comprises:

a) contacting the test compound and a polypeptide selected from the group consisting of
   i) a polypeptide which is encoded by a nucleic acid molecule comprising a portion having a nucleotide sequence which is at least 90% identical to one of SEQ ID NOs: 1 and 3; and
   ii) a fragment of a polypeptide having either an amino acid sequence comprising SEQ ID NO: 2, wherein the fragment comprises at least 15 contiguous amino acid residues of SEQ ID NO: 2 or a cell that expresses the polypeptide; and b) determining whether the polypeptide binds with the test compound.

Binding of the polypeptide and the test compound is an indication that the test compound is useful for modulating the phenomenon. For example, the polypeptide can be one which exhibits an epitope in common with a polypeptide having the amino acid sequence SEQ ID NO: 2.

The invention also includes a method of modulating the ability of a cell to catalyze interconversion of the phosphorylated and de-phosphorylated forms a mitogen-activated protein kinase. The method comprises modulating 15418 protein activity in the cell. The activity of 15418 protein can be modulated by modulating expression of the 15418 gene in the cell, for example by administering to the cell an antisense oligonucleotide which hybridizes under stringent conditions with a transcript (e.g., an mRNA) of the 15418 gene, an antisense oligonucleotide which hybridizes under stringent conditions with a polynucleotide having the nucleotide sequence SEQ ID NO: 41, or an antisense oligonucleotide which hybridizes under stringent conditions with a polynucleotide having the nucleotide sequence SEQ ID NO: 43. Alternatively, the activity of 15418 protein can be modulated without significantly affecting 15418 gene expression in the cell. For example, the activity of 15418 protein activity can be inhibited by administering to the cell an agent which inhibits an activity of 15418, such as an antibody which specifically binds with 15418 protein. The inhibited activity can, for example, be protein phosphatase activity, ability to modulate proliferation of a cell, ability to modulate differentiation of a cell, or ability to modulate a response of a cell to an adrenocortical hormone.

In another aspect, the invention relates to a method for assessing whether a test compound is useful for modulating at least one phenomenon selected from the group consisting of (1) interconversion of the phosphorylated and de-phosphorylated forms of a serine, threonine, or tyrosine residue of a MAPK protein; (2) cell signaling; (3) cell growth; (4) cell differentiation; (5) tumorigenesis; (6) entry of a cell into the cell cycle; (7) progression of a cell through the cell cycle; (8) mitogenesis; (9) cell motility; (10) a cell-to-cell interaction; (11) cell metabolism; (12) gene transcription; (13) an immune response; (14) a cellular response to an adrenocortical hormone; (15) skeletal muscle development; (16) development or progression of muscular dystrophy; (17) spermatogenesis; (18) fertility; (19) tumorigenesis; (20) tumor growth; (21) tumor metastasis; (22) a testosterone-associated disorder; (23) tissue growth in an embryo or fetus; (24) tissue differentiation in an embryo or fetus; (25) organogenesis in an embryo or fetus; (26) wound healing; (27) neuronal growth; and (28) neuronal interconnection. The method comprises:

a) adding the test compound to a first composition comprising a polypeptide that has an amino acid sequence at least 90% identical to SEQ ID NO: 42 and that exhibits a 15418 activity and;

b) comparing the 15418 activity in the first composition and in a second composition that is substantially identical to the first composition except that it does not comprise the test compound.

A difference in the 15418 activity in the first and second compositions is an indication that the test compound is useful for modulating the phenomenon.

The invention also includes a method for assessing whether a test compound is useful for modulating at least one phenomenon selected from the group consisting of (1) interconversion of the phosphorylated and de-phosphorylated forms of a serine, threonine, or tyrosine residue of a MAPK protein; (2) cell signaling; (3) cell growth; (4) cell differentiation; (5) tumorigenesis; (6) entry of a cell into the cell cycle; (7) progression of a cell through the cell cycle; (8) mitogenesis; (9) cell motility; (10) a cell-to-cell interaction; (11) cell metabolism; (12) gene transcription; (13) an immune response; (14) a cellular response to an adrenocortical hormone; (15) skeletal muscle development; (16) development or progression of muscular dystrophy; (17) spermatogenesis; (18) fertility; (i 9) tumorigenesis; (20) tumor growth; (21) tumor metastasis; (22) a testosterone-associated disorder; (23) tissue growth in an embryo or fetus; (24) tissue differentiation in an embryo or fetus; (25) organogenesis in an embryo or fetus; (26) wound healing; (27) neuronal growth; and (28) neuronal interconnection. This method comprises:

a) adding the test compound to a first composition comprising a cell which comprises a nucleic acid that encodes a polypeptide that has an amino acid sequence at least 90% identical to SEQ ID NO: 42 and that exhibits a 15418 activity and;

b) comparing 15418 activity in the first composition and in a second composition that is substantially identical to the first composition except that it does not comprise the test compound.

A difference in the 15418 activity in the first and second compositions is an indication that the test compound is useful for modulating the phenomenon.

The invention further relates to a method of making a pharmaceutical composition for modulating at least one phenomenon selected from the group consisting of (1) interconversion of the phosphorylated and de-phosphorylated forms of a serine, threonine, or tyrosine residue of a MAPK protein; (2) cell signaling; (3) cell growth; (4) cell differentiation; (5) tumorigenesis; (6) entry of a cell into the cell cycle; (7) progression of a cell through the cell cycle; (8) mitogenesis; (9) cell motility; (10) a cell-to-cell interaction; (11) cell metabolism; (12) gene transcription; (13) an immune response; (14) a cellular response to an adrenocortical hormone; (15) skeletal muscle development; (16) development or progression of muscular dystrophy; (17) spermatogenesis; (18) fertility; (19) tumorigenesis; (20) tumor growth; (21) tumor metastasis; (22) a testosterone-associated disorder; (23) tissue growth in an embryo or fetus; (24) tissue differentiation in an embryo or fetus; (25) organogenesis in an embryo or fetus; (26) wound healing; (27) neuronal growth; and (28) neuronal interconnection. The method comprises selecting a test compound useful for modulating the phenomenon as described herein and combining the test compound with a pharmaceutically acceptable carrier in order to make the pharmaceutical composition. This composition can be used to modulate one or more of these phenomena.

The invention includes another method for identifying a compound useful for modulating at least one phenomenon selected from the group consisting of (1) interconversion of the phosphorylated and de-phosphorylated forms of a serine, threonine, or tyrosine residue of a MAPK protein; (2) cell signaling; (3) cell growth; (4) cell differentiation; (5) tumorigenesis; (6) entry of a cell into the cell cycle; (7) progression of a cell through the cell cycle; (8) mitogenesis; (9) cell motility; (10) a cell-to-cell interaction; (11) cell metabolism; (12) gene transcription; (13) an immune response; (14) a cellular response to an adrenocortical hormone; (15) skeletal muscle development; (16) development or progression of muscular dystrophy; (17) spermatogenesis; (18) fertility; (19) tumorigenesis; (20) tumor growth; (21) tumor metastasis; (22) a testosterone-associated disorder; (23) tissue growth in an embryo or fetus; (24) tissue differentiation in an embryo or fetus; (25) organogenesis in an embryo or fetus; (26) wound healing; (27) neuronal growth; and (28) neuronal interconnection. This method comprises:

a) contacting the test compound and a polypeptide selected from the group consisting of
   i) a polypeptide which is encoded by a nucleic acid molecule comprising a portion having a nucleotide sequence which is at least 90% identical to one of SEQ ID NOs: 41 and 43; and
   ii) a fragment of a polypeptide having either an amino acid sequence comprising SEQ ID NO: 42, wherein the fragment comprises at least 25 contiguous amino acid residues of SEQ ID NO: 42 or a cell that expresses the polypeptide; and b) determining whether the polypeptide binds with the test compound.

Binding of the polypeptide and the test compound is an indication that the test compound is useful for modulating the phenomenon. For example, the polypeptide can be one which exhibits an epitope in common with a polypeptide having the amino acid sequence SEQ ID NO: 42.

Other features and advantages of the invention will be apparent from the following detailed description, and from the claims.

BRIEF DESCRIPTION OF THE SEVERAL VIEWS OF THE DRAWINGS

FIG. 1, comprising FIGS. 1A through 1D, depicts a cDNA sequence (SEQ ID NO: 1) and predicted amino acid sequence (SEQ ID NO: 2) of human 69087. The methionine-initiated open reading frame of human 69087 (without the 5'- and 3'-non-translated regions) starts at nucleotide 291 of SEQ ID NO: 1, and the coding region (not including the terminator codon; shown in SEQ ID NO: 3) extends through nucleotide 1949 of SEQ ID NO: 1.

FIG. 3, comprising FIGS. 3A through 3C, is an alignment of the amino acid sequence of 69087 ("69087"; SEQ ID NO:2), SGK064 ("SGK064"; SEQ ID NO: 11), *Spermophilus tridecemlineatus* GRK7 ("ST GRK7"; SEQ ID NO: 12), *Oryzias latipes* GRK ("OL GRK7"; SEQ ID NO: 13), and *Cyprinus carpio* GRK7 ("CC GRK7"; SEQ ID NO: 14), made using the ALIGN software and its default settings. The amino acid sequence "SGK064" corresponds to the amino acid sequence in the PCT application having publication number WO 01/38503 designated SGK064 and appearing as seq id no: 59 of the sequence listing in that publication. The amino acid sequence "ST GRK7" corresponds to GENBANK® accession number AAC95001 which is the amino acid sequence encoded by the G protein-coupled receptor kinase 7 (GRK7) gene from ground squirrel. The amino acid sequence "OL GRK7" corresponds to GENBANK® accession number BAA25670 which is the amino acid sequence encoded by the GRK7 gene from Japanese medaka fish. The amino acid sequence "CC GRK7" corresponds to GENBANK® accession number BAB32498 which is the amino acid sequence encoded by the GRK7 gene from carp. The ALIGN software is available at various World Wide Web addresses, and default parameters used at any of those sites can be used.

FIG. 4, comprising FIGS. 4A through 4E, depicts a cDNA sequence (SEQ ID NO: 21) and predicted amino acid sequence (SEQ ID NO: 22) of human 15821. The methionine-initiated open reading frame of human 15821 (without the 5'- and 3'-non-translated regions) starts at nucleotide 235 of SEQ ID NO: 21, and the coding region (not including the terminator codon; shown in SEQ ID NO: 23) extends through nucleotide 1926 of SEQ ID NO: 21.

FIG. 6, comprising FIGS. 6A through 6C, is an alignment of the amino acid sequence of human 15821 ("15821 "; SEQ ID NO: 22), a protein designated C14orf4 ("C14orf4"; SEQ ID NO: 31), and a protein designated KIAA1865 ("KIAA1865"; SEQ ID NO: 32), made using the ALIGN software and its default settings. The amino acid sequence "C14orf4" corresponds to GENBANK® accession number CAC10539. The amino acid sequence "KIAA 1865" corresponds to GENBANK® accession number BAB47494. The ALIGN software is available at various World Wide Web addresses, and default parameters used at any of those sites can be used.

FIG. 7, comprising FIGS. 7A and 7B is an alignment of a carboxy-terminal portion of the amino acid sequence of human 15821 ("15821 "; SEQ ID NO: 22), a protein designated C14orf4 ("C14orf4"; SEQ ID NO: 31), a protein designated KIAA1865 ("KIAA1865"; SEQ ID NO: 32), a breast and ovarian cancer associated antigen protein ("736"; SEQ ID NO: 33), a human transcriptional regulator molecule ("HTRM"; SEQ ID NO: 34), a human secreted protein ("dn740_3"; SEQ ID NO: 35), and an unnamed protein ("Unnamed"; SEQ ID NO: 36) made using the ALIGN software and its default settings. An underline indicates a predicted C3HC4 type zinc finger (RING finger) domain in the amino acid sequence of human 15821 and bold-face type indicates the cysteine and histidine residues predicted to comprise part of the C3HC4 structure. The amino acid sequence "C14orf4" corresponds to GENBANK® accession number CAC10539. The amino acid sequence "KIAA 1865" corresponds to GENBANK® accession number BAB47494. The amino acid sequence "736" corresponds to the amino acid sequence in the PCT application having publication number WO 98/41539 appearing as seq id no: 736 of the sequence listing in that publication. The amino acid sequence "HTRM" corresponds to the amino acid sequence in the PCT application having publication number WO 99/57144 designated clone 1821233 and appearing as seq id no: 56 of the sequence listing in that publication. The amino acid sequence "dn740_3" corresponds to the amino acid sequence in the PCT application having publication number WO 98/41539 designated dn740_3 and appearing as seq id no: 13 of the sequence listing in that publication. The amino acid sequence "Unnamed" corresponds to GENBANK® accession number CAC38497 and is an amino acid sequence in the PCT application having publication number WO 01/29221. The ALIGN software is available at various World Wide Web addresses, and default parameters used at any of those sites can be used.

FIG. 8, comprising FIGS. 8A and 8B, lists the cDNA sequence (SEQ ID NO: 41) and predicted amino acid sequence (SEQ ID NO: 42) of human 15418. The methionine-initiated open reading frame of human 15418 (without the 5'- and 3'-non-translated regions) starts at nucleotide 164 of SEQ ID NO: 41, and the coding region (not including the terminator codon; shown in SEQ ID NO: 43) extends through nucleotide 733 of SEQ ID NO: 41.

FIG. 10 is an alignment of the amino acid sequence of 15418 protein (SEQ ID NO: 42) and the amino acid sequence of DSP-8 protein (SEQ ID NO: 44), which is disclosed in the PCT application having publication number WO 00/63393.

DETAILED DESCRIPTION OF THE INVENTION

69087 Nucleic Acid and Protein

Figure 2:
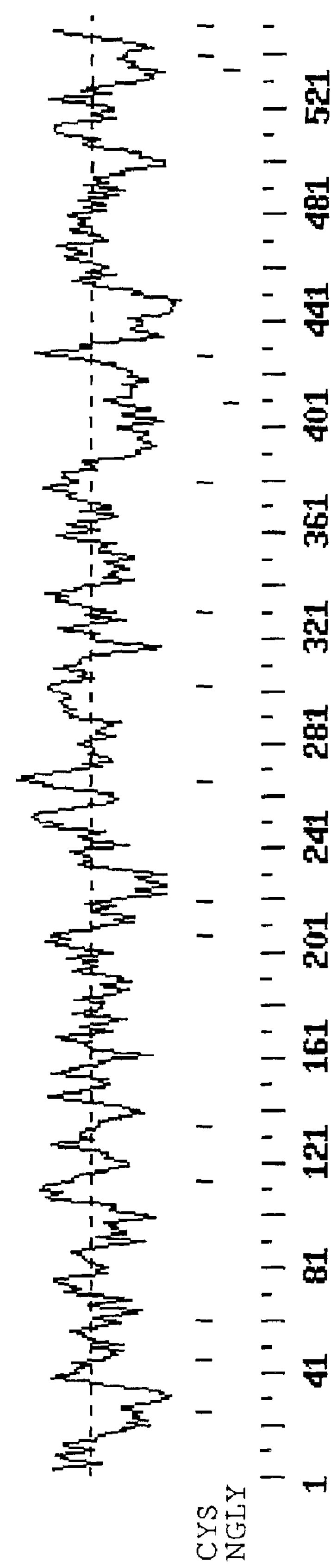
FIG. 2 depicts a hydropathy plot of human 69087. Relatively hydrophobic residues are shown above the dashed horizontal line, and relative hydrophilic residues are below the dashed horizontal line. The cysteine residues (cys) are indicated by short vertical lines below the hydropathy trace. The numbers corresponding to the amino acid sequence of human 69087 are indicated. Polypeptides of the invention include fragments which include: all or part of a hydrophobic sequence, i.e., a sequence above the dashed line, e.g., the sequence of about residues 290–310 of SEQ ID NO: 2; all or part of a hydrophilic sequence, i.e., a sequence below the dashed line, e.g., the sequence of residues 15–30 and 385–415 of SEQ ID NO: 2; a sequence which includes a cysteine residue; or a glycosylation site.
Figure 5:
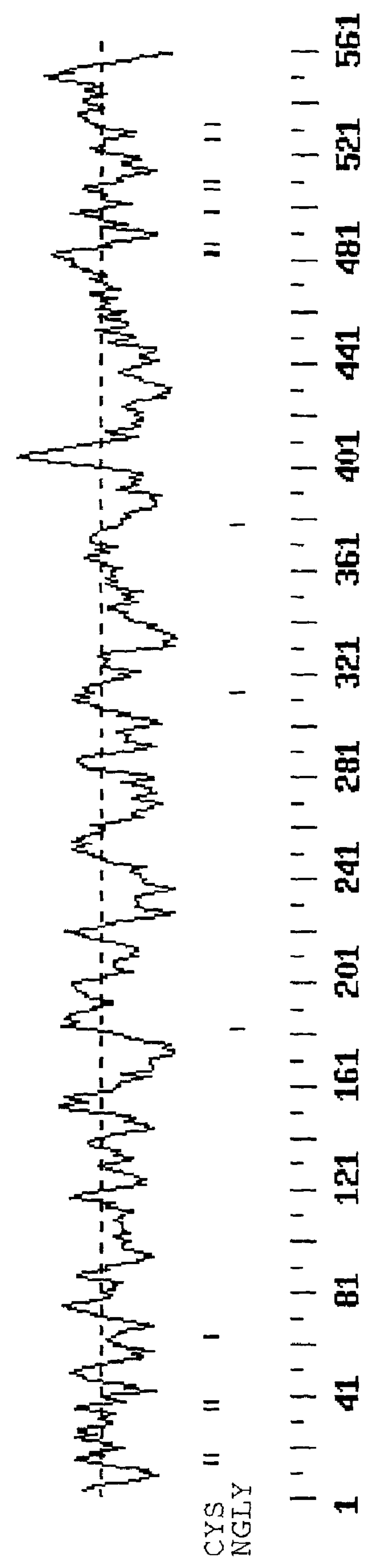
FIG. 5 depicts a hydropathy plot of human 15821. Relatively hydrophobic residues are shown above the dashed horizontal line, and relative hydrophilic residues are below the dashed horizontal line. The cysteine residues (cys) are indicated by short vertical lines below the hydropathy trace. The numbers corresponding to the amino acid sequence of human 15821 are indicated. Polypeptides of the invention include fragments which include: all or part of a hydrophobic sequence, i.e., a sequence above the dashed line, e.g., the sequence of about residues 395–405 of SEQ ID NO: 22; all or part of a hydrophilic sequence, i.e., a sequence below the dashed line, e.g., the sequence of about residues 160–180 or 220–240 of SEQ ID NO: 22; a sequence which includes a cysteine residue; or a glycosylation site.
Figure 9:
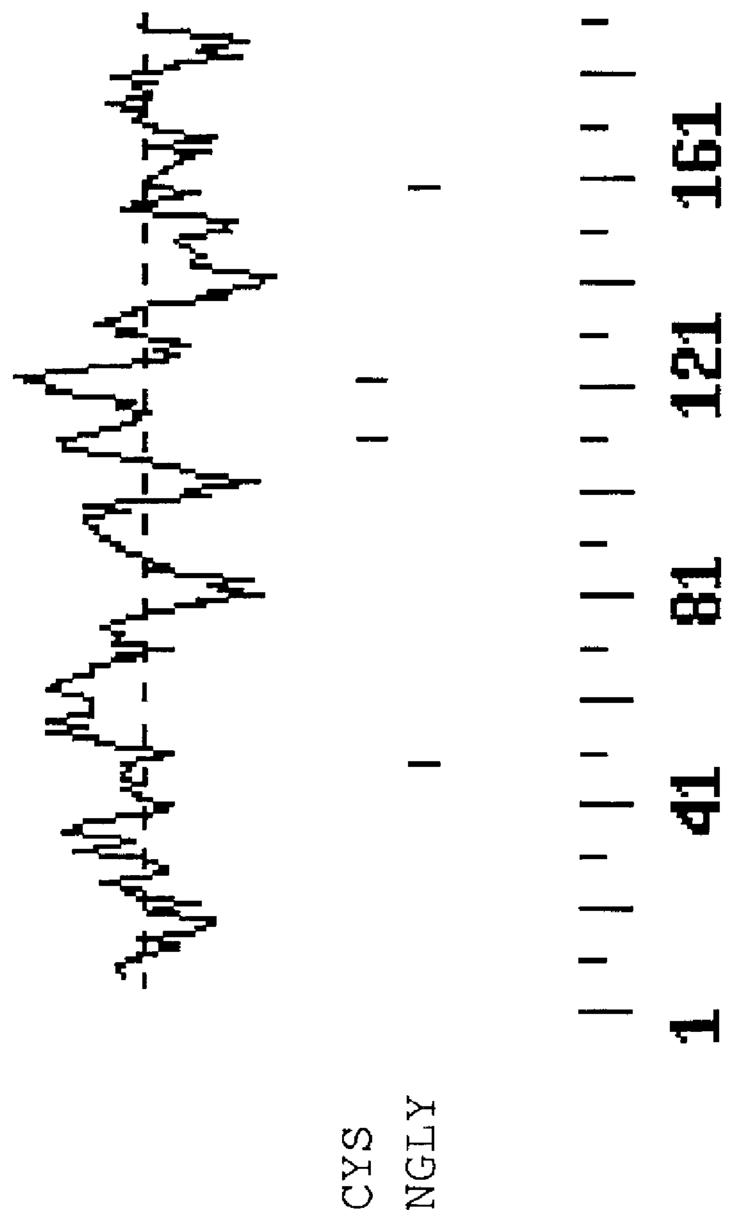
FIG. 9 depicts a hydropathy plot of human 15418. Relatively hydrophobic residues are shown above the dashed horizontal line, and relative hydrophilic residues are below the dashed horizontal line. The cysteine residues (cys) are indicated by short vertical lines below the hydropathy trace The numbers corresponding to the amino acid sequence of human 15418 are indicated. Polypeptides of the invention include fragments which include: all or part of a hydrophobic sequence, i.e., a sequence above the dashed line, e.g., the sequence of about residues 45–60 of SEQ ID NO: 42; all or part of a hydrophilic sequence, i.e., a sequence below the dashed line, e.g., the sequence of residues 130–155 of SEQ ID NO: 42; a sequence which includes a cysteine residue; or a glycosylation site.

The human 69087 cDNA sequence (FIG. 1; SEQ ID NO: 1), which is approximately 2198 nucleotide residues long including non-translated regions, contains a predicted methionine-initiated coding sequence of about 1659 nucleotide residues, excluding termination codon (i.e., nucleotide residues 291–1949 of SEQ ID NO: 1; also shown in SEQ ID NO: 3). The coding sequence encodes a 553 amino acid protein having the amino acid sequence SEQ ID NO: 2.

Human 69087 contains the following regions or other structural features: a predicted pkinase domain (PF00069) at about amino acid residues 191 to 454 of SEQ ID NO: 2, a predicted protein kinase C terminal domain (PF00442) at residues 455 to 471 of SEQ ID NO: 2, and RGS domains at residues 55 to 78 and 162 to 176 of SEQ ID NO: 2.

The human 69087 protein has predicted N-glycosylation sites (Pfam accession number PS00001) at about amino acid residues 418–421 and 543–546 of SEQ ID NO: 2; predicted cAMP-/cGMP-dependent protein kinase phosphorylation sites (Pfam accession number PS00004) at about amino acid residues 20–23 and 33–36 of SEQ ID NO: 2; predicted protein kinase C phosphorylation sites (Pfam accession number PS00005) at about amino acid residues 79–81, 148–150, 187–189, 213–215, 348–350, and 544–546 of SEQ ID NO: 2; predicted casein kinase II phosphorylation sites (Pfam accession number PS00006) located at about amino acid residues 23–26, 58–61, 85–88, 138–141, 380–383, 399–402, 407–410, and 537–540 of SEQ ID NO: 2; predicted N-myristoylation sites (Pfam accession number PS00008) at about amino acid residues 5–10, 41–46, 108–113, 287–292, and 538–543 of SEQ ID NO: 2; a predicted amidation site (Pfam accession number PS00009) at about amino acid residues 65–68 of SEQ ID NO: 2, a predicted protein kinase ATP-binding region signature domain (Pfam accession number PS00107) at residues 197–205 of SEQ ID NO: 2, a predicted serine/threonine protein kinase active site signature sequence (Pfam accession number PS00108) at residues 312–324 of SEQ ID NO: 2, and a predicted prenyl group binding site (Pfam accession number PS00294) at residues 550–553 of SEQ ID NO: 2.

For general information regarding PFAM identifiers, PS prefix and PF prefix domain identification numbers, refer to Sonnhammer et al. (1997, Protein 28:405–420) and www.psc.edu/general/software/packages/pfam/pfam.html.

The 69087 protein contains a significant number of structural characteristics in common with members of the GPCRK family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., GPCRK proteins for any species described in the art (e.g., Bünemann et al., 1999, J. Physiol.

517.1:5–23 and references cited therein). Members of a family can also have common functional characteristics.

A 69087 polypeptide can include a pkinase domain. As used herein, the term "pkinase domain" refers to a protein domain having an amino acid sequence of about 200–300 amino acid residues in length, preferably, at least about 225–300 amino acids, more preferably about 278 amino acid residues or about 251 amino acid residues and has a bit score for the alignment of the sequence to the pkinase domain (HMM) of at least 100 or greater, preferably 200 or greater, and more preferably 300 or greater. The pkinase domain has been assigned the PFAM accession PF00069 (genome.wustl.edu/Pfam/html).

A 69087 polypeptide can also include one or more Regulator of G protein Signaling (RGS) domains. As used herein, the term "RGS domain" refers to a protein domain having a conserved amino acid sequence as described (Watson et al., 1996, Nature 383:172–175 and references cited therein). The RGS domain has been assigned the PFAM accession PF00615 (genome.wustl.edu/Pfam/html).

In a preferred embodiment, 69087 polypeptide or protein has a pkinase domain or a region which includes at least about 200–300, more preferably about 225–300, 278, or 251 amino acid residues and has at least about 60%, 70%, 80%, 90%, 95%, 99%, or 100% homology with a pkinase domain, e.g., the pkinase domain of human 69087 (e.g., residues 191–454 of SEQ ID NO: 2). The 69087 preferably also has a RGS domain that has at least about 60%, 70%, 80%, 90%, 95%, 99%, or 100% homology with an RGS domain of 69087 (e.g., residues 55–78 or 162–176 of SEQ ID NO: 2).

To identify the presence of a pkinase domain profile in a 69087 receptor, the amino acid sequence of the protein is searched against a database of HMMs (e.g., the Pfam database, release 2.1) using common default parameters (www.sanger.ac.uk/Software/Pfam/HMM_search). For example, the hmmsf program, which is available as part of the HMMER package of search programs, is a family specific default program for PF00069 and score of 100 is the default threshold score for determining a hit. For example, using ORF Analyzer software, a pkinase domain profile was identified in the amino acid sequence of SEQ ID NO: 2 (e.g., amino acids 53–303 of SEQ ID NO: 2). Accordingly, a 69087 protein having at least about 60–70%, more preferably about 70–80%, or about 80–90% homology with the pkinase domain profile of human 69087 is within the scope of the invention. To identify the presence of an RGS domain profile in a 69087 receptor, the amino acid sequence of the protein is searched using a family specific default program for PF00615 and a default score of 1 or greater (preferably 10 or greater).

In one embodiment of the invention, a 69087 polypeptide includes at least one pkinase domain. In another embodiment, the 69087 polypeptide includes at least one pkinase domain and at least one RGS domain. The 69087 molecules of the present invention can further include one or more of the N-glycosylation, cAMP-/cGMP-dependent protein kinase phosphorylation, protein kinase C phosphorylation, casein kinase II phosphorylation, N-myristoylation, amidation, protein kinase ATP-binding region signature, serine/threonine protein kinase active site, and prenyl group binding sites described herein, and preferably comprises most or all of them.

Because the 69087 polypeptides of the invention can modulate 69087-mediated activities, they can be used to develop novel diagnostic and therapeutic agents for 69087-mediated or related disorders, as described below.

As used herein, a "69087 activity," "biological activity of 69087," or "functional activity of 69087," refers to an activity exerted by a 69087 protein, polypeptide or nucleic acid molecule on, for example, a 69087-responsive cell or on a 69087 substrate (e.g., a protein substrate) as determined in vivo or in vitro. In one embodiment, a 69087 activity is a direct activity, such as association with a 69087 target molecule. A "target molecule" or "binding partner" of a 69087 protein is a molecule (e.g., a protein or nucleic acid) with which the 69087 protein binds or interacts in nature. In an exemplary embodiment, such a target molecule is a GPCR receptor. A 69087 activity can also be an indirect activity, such as a cellular signaling activity mediated by phosphorylation of a GPCR receptor mediated by the 69087 protein.

The 69087 molecules of the present invention are predicted to have similar biological activities as GPCRK family members. For example, the 69087 proteins of the present invention can have one or more of the following activities:

(1) catalyzing formation of a covalent bond within or between an amino acid residue of a GPCR and a phosphate moiety;
(2) modulating cell signaling;
(3) modulating cell growth;
(4) modulating cell differentiation;
(5) modulating tumorigenesis;
(6) modulating entry of a cell into the cell cycle;
(7) modulating progression of a cell through the cell cycle;
(8) modulating mitogenesis;
(9) modulating cell motility;
(10) modulating a cell-to-cell interaction;
(11) modulating cell metabolism;
(12) modulating gene transcription;
(13) modulating cardiac function;
(14) modulating transmission of nerve impulses;
(15) modulating olfaction;
(16) modulating vision;
(17) modulating photoreceptor signaling;
(18) modulating uncoupling of receptors and heterotrimeric G-proteins;
(19) modulating development of color-blindness;
(20) modulating susceptibility to impaired night vision;
(21) modulating susceptibility to blindness;
(22) modulating susceptibility to retinitis pigmentosa;
(23) modulating susceptibility to macular degeneration;
(24) modulating photoreceptor cell apoptosis;
(25) modulating photoreceptor cell differentiation;
(26) modulating visual pigmentation; and
(27) modulating photoreceptor desensitization.

Thus, 69087 molecules described herein can act as novel diagnostic targets and therapeutic agents for prognosticating, diagnosing, preventing, inhibiting, alleviating, or curing GPCRK-related disorders.

As indicated in FIG. 3, human 69087 protein exhibits significant sequence homology with a protein designated GRK7 which has been identified in both medaka retina, ground squirrel retina, and carp retina (Hisatomi et al., 1998, FEBS Letters 424:159–164; Weiss et al., 1998, Mol. Vis. 4:27–34; Shimauchi et al., 2001, direct GENBANK® submission, accession no. BAB32498). Ground squirrel GRK7 phosphorylates rhodopsin in a light-dependent manner, consistent with a role as an opsin kinase. The homology data presented herein indicates that human 69087 is a human GRK7 protein that can function as a G protein-coupled receptor kinase. More specifically, these data indicate that human 69087 can phosphorylate cone opsins (i.e., red, green, or blue opsin) and rod opsins (i.e., rhodopsin). Therefore, human 69087 can function in one or more aspect relating to vision and visual signaling pathways. For example, 69087 can mediate one or more of desensitization of photoreceptors, uncoupling of receptors and G proteins, regulation of visual pigmentation, and color perception.

Human 69087 protein also exhibits substantial sequence identity with a protein designated SGK064 (disclosed in the PCT application having publication number WO 01/38503). The 69087 polypeptide differs from SGK064 at amino acid residues 150, 322, and 440. SGK064 has been tentatively mapped to human chromosomal location 3q24. Previously recognized genetic aberrations associated with various disorders and diseases (e.g., uveal melanoma {Tschentscher et al., 2001, Cancer Res. 61:3439–3442}, diploid meningioma {Farber et al., 1991, Cytogenet. Cell Genet. 57:157–8}, squamous cell carcinoma {Hermsen et al., 2001, J. Pathol. 194:177–182}, lung adenocarcinomas {Pei et al., 2001, Genes Chromosomes Cancer 31:282–287}, Usher syndrome {Gasparini et al., 1998, J. Med. Genet. 35:666–667}, neuroblastomas {Brinkschmidt et al., 1997, J. Pathol. 181:394–400}, and maple syrup urine disease {Chuang et al., 1991, Mol. Biol. Med., 8:49–63}) have been mapped to this region, indicating that 69087 can affect susceptibility of an individual to one or more of these disorders or progression or severity of any of these disorders.

Other activities, as described below, include the ability to modulate function, survival, morphology, proliferation and/or differentiation of cells of tissues in which 69087 molecules are expressed. Thus, the 69087 molecules can act as novel diagnostic targets and therapeutic agents for controlling disorders involving aberrant activities of these cells.

The 69087 molecules can also act as novel diagnostic targets and therapeutic agents for controlling cellular proliferative and/or differentiative disorders (e.g., hematopoietic neoplastic disorders, leukemia, carcinoma, sarcoma, or metastatic disorders). A metastatic tumor can arise from a multitude of primary tumor types, including but not limited to those of prostate, colon, lung, breast, eye, and liver origin.

15821 Nucleic Acid and Protein

The human 15821 cDNA sequence (FIG. 4; SEQ ID NO: 21), which is approximately 3003 nucleotide residues long including non-translated regions, contains a predicted methionine-initiated coding sequence of about 1692 nucleotide residues, excluding termination codon (i.e., nucleotide residues 235–1926 of SEQ ID NO: 21; also shown in SEQ ID NO: 23). The coding sequence encodes a 564 amino acid residue protein having the amino acid sequence SEQ ID NO: 22.

Human 15821 contains a predicted C3HC4 type zinc finger domain (RING finger domain; PF00069) at about amino acid residues 483 to 528 of SEQ ID NO: 22. A transmembrane domain is predicted at about amino acid residues 470 to 486 of SEQ ID NO: 22.

The human 15821 protein has predicted N-glycosylation sites (Pfam accession number PS00001) at about amino acid residues 191–194, 322–325 and 387–390 of SEQ ID NO: 22; predicted cAMP-/cGMP-dependent protein kinase phosphorylation sites (Pfam accession number PS00004) at about amino acid residues 10–13, 334–337, and 429–432 of SEQ ID NO: 22; predicted protein kinase C phosphorylation sites (Pfam accession number PS00005) at about amino acid residues 8–10, 53–55, 85–87, 133–135, 281–283, 330–332, 386–388, 427–429, 503–505, and 514–516 of SEQ ID NO: 22; predicted casein kinase II phosphorylation sites (Pfam accession number PS00006) located at about amino acid residues 85–88, 161–164, 281–284, 359–362, 390–393, and 469–472 of SEQ ID NO: 22; and predicted N-myristoylation sites (Pfam accession number PS00008) at about amino acid residues 72–77, 100–105, 128–133, 263–268, 320–325, 413–418, and 452–457 of SEQ ID NO: 22.

For general information regarding PFAM identifiers, PS prefix and PF prefix domain identification numbers, refer to Sonnhammer et al. (1997, Protein 28:405–420) and www.psc.edu/general/software/packages/pfam/pfam.html.

The 15821 protein contains a significant number of structural characteristics in common with members of the zinc finger and nuclear signaling families of proteins. For example, the family can contain a first protein of human origin as well as other distinct proteins of human origin, or alternatively, can contain homologues of non-human origin, e.g., other RING finger proteins, such as those described in PDOC00449, which can be accessed through the Pfam site described elsewhere herein. Examples of such proteins include mammalian V(D)J recombination activating protein RAG1, murine Rpt1 protein, human Rfp protein, human 52 Kd Ro/SS-A protein, human histocompatibility locus protein RING1, human probable transcription factor PML, mammalian breast cancer type I susceptibility protein Brca1, mammalian proto-oncogene cbl, mammalian proto-oncogene bmi-1, vertebrate CDK-activating kinase assembly factor MAT1 mammalian transcriptional repressor mel-18, mammalian peroxisome assembly factor-1, Xenopus probable transcription factor XNF7, Trypanosomal post-transcriptional regulator protein ESAG-8, Drosophila PSC protein, *Drosophila* Su(z)2 protein, Drosophila DNA-binding protein msl-2, *Arabidopsis thaliana* photomorphogenesis regulatory protein COP1, fungal DNA repair proteins RAD5, RAD16, RAD18, and RAD8, herpesvirus trans-acting transcriptional protein ICP0/IE110, baculovirus protein CG30, baculovirus major immediate early protein PE-38, baculovirus immediate-early regulatory protein IE-N/IE-2, Caenorhabditis elegans hypothetical proteins F54G8.4, R05D3.4, and T02C1.1, and yeast hypothetical proteins YER116c and YKR017c. Members of a family can also have common functional characteristics.

A 15821 polypeptide can include a C3HC4 type zing finger domain (a RING finger domain). As used herein, the term “RING finger domain” refers to a protein domain having an amino acid sequence of about 30–70 amino acid residues in length, preferably, at least about 40–70 amino acids, more preferably about 46 amino acid residues and has a bit score for the alignment of the sequence to the RING finger domain (HMM) of at least 5 or greater, preferably 10 or greater, and more preferably 13 or greater. The RING finger domain has been assigned the PFAM accession PF00097 (genome.wustl.edu/Pfam/html).

In a preferred embodiment, 15821 polypeptide or protein has a RING finger domain or a region which includes at least about 30–70, more preferably about 40–60, or 46 amino acid residues and has at least about 60%, 70%, 80%, 90%, 95%, 99%, or 100% homology with a RING finger domain, e.g., the RING finger domain of human 15821 (e.g., residues 483–528 of SEQ ID NO: 22).

To identify the presence of a RING finger domain profile in a 15821 receptor, the amino acid sequence of the protein is searched against a database of HMMs (e.g., the Pfam database, release 2.1) using common default parameters such as those found at (www.sanger.ac.uk/Software/Pfam/

HMM_search). For example, the hmmsf program, which is available as part of the HMMER package of search programs, is a family specific default program for PF00097 and score of 5 is the default threshold score for determining a hit. For example, using ORFAnalyzer software, a RING finger domain profile was identified in the amino acid sequence of SEQ ID NO: 22 (e.g., amino acids 483–528 of SEQ ID NO: 22). Accordingly, a 15821 protein having at least about 60–70%, more preferably about 70–80%, or about 80–90% homology with the RING finger domain profile of human 15821 is within the scope of the invention.

In one embodiment, a 15821 protein includes at least one transmembrane domain. As used herein, the term "transmembrane domain" includes an amino acid sequence of about 5 amino acid residues in length that spans the plasma membrane. More preferably, a transmembrane domain includes about at least 10, 15, 20 or 22 amino acid residues and spans a membrane. Transmembrane domains are rich in hydrophobic residues, and typically have an alpha-helical structure. In a preferred embodiment, at least 50%, 60%, 70%, 80%, 90%, or 95% or more of the amino acids of a transmembrane domain are hydrophobic, e.g., leucines, isoleucines, tyrosines, or tryptophans. Transmembrane domains are described in, for example, pfam.wustl.edu/cgi-bin/getdesc?name=7tm-1, and Zagotta W. N. et al. (1996, Annu. Rev. Neurosci. 19: 235–263), the contents of which are incorporated herein by reference. Amino acid residues 470 to about 482 of SEQ ID NO: 22 comprise a transmembrane domain in a 15821 protein. In one embodiment, the amino-terminal domain of 15821 protein (i.e., about residues 1–469 of SEQ ID NO: 22) is on the cytoplasmic side of a cellular membrane (e.g., the nuclear membrane or the cytoplasmic membrane) and the carboxyl-terminal domain (i.e., about residues 483–564 of SEQ ID NO: 22) is on the non-cytoplasmic side of the same membrane. In another embodiment, the amino-terminal domain is oriented on the non-cytoplasmic side of the membrane and the carboxyl-terminal domain is oriented on the cytoplasmic side.

While not being bound by any particular theory of operation, 15821 protein is believed to be, in at least one embodiment, a nuclear membrane protein having its amino-terminal domain oriented within the nuclear envelope. In this embodiment, 15821 protein is capable of transmitting signaling information from the cytoplasm to the nucleus, whereby, for example, gene transcription can be regulated. 15821 protein can, in a different embodiment, have the opposite orientation, with its carboxyl-terminal domain oriented within the nuclear envelope.

In one embodiment of the invention, a 15821 polypeptide includes at least one RING finger domain. In another embodiment, the 15821 polypeptide includes at least one RING finger domain and at least one transmembrane domain. The 15821 molecules of the present invention can further include one or more of the N-glycosylation, cAMP-/cGMP-dependent protein kinase phosphorylation, protein kinase C phosphorylation, casein kinase II phosphorylation, and N-myristoylation sites described herein, and preferably comprises most or all of them.

Because the 15821 polypeptides of the invention can modulate 15821-mediated activities, they can be used to develop novel diagnostic and therapeutic agents for 15821-mediated or related disorders, as described below.

As used herein, a "15821 activity," "biological activity of 15821," or "functional activity of 15821," refers to an activity exerted by a 15821 protein, polypeptide or nucleic acid molecule on, for example, a 15821-responsive cell or on a 15821 substrate (e.g., a protein substrate) as determined in vivo or in vitro. In one embodiment, a 15821 activity is a direct activity, such as association with a 15821 target molecule. A "target molecule" or "binding partner" of a 15821 protein is a molecule (e.g., a protein or nucleic acid) with which the 15821 protein binds or interacts in nature. In an exemplary embodiment, such a target molecule is a 15821 receptor. A 15821 activity can also be an indirect activity, such as a cellular (e.g., nuclear transmembrane) signaling activity mediated by interaction of the 15821 protein with a 15821 receptor.

The 15821 molecules of the present invention are predicted to have similar biological activities as nuclear signaling protein and RING finger protein family members. For example, the 15821 proteins of the present invention can have one or more of the following activities:

(1) binding with a cytoplasmic cell signaling mediator;
(2) binding with a nuclear cell signaling mediator;
(3) binding with a nuclear membrane protein to form a signaling complex;
(4) modulating cell signaling;
(5) modulating cell growth;
(6) modulating cell differentiation;
(7) modulating tumorigenesis;
(8) modulating entry of a cell into the cell cycle;
(9) modulating progression of a cell through the cell cycle;
(10) modulating mitogenesis;
(11) modulating cell motility;
(12) modulating a cell-to-cell interaction;
(13) modulating cell metabolism;
(14) modulating gene transcription;
(15) modulating an immune response;
(16) modulating apoptosis;
(17) modulating neural degeneration;
(18) modulating formation of inclusion bodies;
(19) modulating proteosome activities;
(20) modulating protein clearance;
(21) modulating metabolic stress;
(22) modulating protein translation;
(23) modulating transcription
(24) modulating vesicle transport;
(25) modulating protein localization; and
(25) modulating cytoskeleton integrity.

Thus, 15821 molecules described herein can act as novel diagnostic targets and therapeutic agents for prognosticating, diagnosing, preventing, inhibiting, alleviating, or curing disorders related to aberrant or undesired cell or nuclear signaling.

As shown in FIG. 6, human 15821 exhibits significant sequence homology with a protein designated C14orf4 (Rampazzo et al., 2000, Biochem. Biophys. Res. Commun. 278:766–774). C14orf4 comprises polyglutamine and polyalanine tracts that vary in length and are present at the amino terminus. The codons which encode glutamine and alanine are often associated with trinucleotide instability which can lead to expansion of a poly-amino acid tract. Trinucleotide instability is associated with numerous disorders.

Human 15821 protein comprises an amino-terminal stretch of glutamine residues (beginning at amino acid 92 of SEQ ID NO: 22). An analogous region of C14orf4 comprises a polyglutamine tract which exhibits variable lengths.

Polyglutamine expansion results in a protein that can be toxic to a cell. Proteins comprising expanded polyglutamine tracts fail to fold properly and are susceptible to abnormal proteolytic cleavage, yielding glutamine-rich protein fragments that form aggregates that are most often found in the nucleus (i.e., intranuclear inclusions) but are also often found in the cytoplasm and near intracellular membranes. The aggregates are frequently associated with proteins associated with the proteolytic pathway, such as ubiquitin, heat shock proteins, and components of the proteosome. The association of polyglutamine-containing protein aggregates with components of the proteolytic pathway results in an inability of a cell to properly degrade proteins and clear protein debris from the cell. Furthermore, evidence suggests that intranuclear inclusions instigate an apoptotic cascade leading to pathological cell death.

The homology data presented herein indicate that human 15821 gene can be susceptible to trinucleotide repeat instability and can be involved in a disorder that results from trinucleotide repeat expansion, aberrant aggregation of polyglutamine-containing proteins, or another property of aberrant 15821 nucleic acids or proteins. Therefore, identification of molecules that modulate 15821 expression, activity, or both, can provide useful tools for diagnosing, preventing, alleviating, treating, reducing, reversing, or curing such disorders. Examples of these disorders include neuronal disorders such as cognitive disorders, neurodegenerative disorders, mental disorders, and ischemic neural damage. Examples of these include a variety of neurological disorders such Huntington's disease, dentatorubralpallidoluysian atrophy, spinobulbar muscular dystrophy, spinocerebellar ataxia, myotonic dystrophy, Fragile X syndrome, and Friedreich's ataxia. Other disorders that can involve polyglutamine expansions include, for example, bipolar disorder, schizophrenia, mental retardation, Parkinson's disease, Alzheimer's disease, epilepsy, obsessive-compulsive disorder, depression, major depressive disorder, addictive behaviors, inappropriate aggression, attention deficit disorder, insomnia, seizures of various etiologies (including epileptic seizures), tardive dyskinesia, motor function disturbances, and developmental abnormalities (such as delayed development).

Other activities, as described below, include the ability to modulate function, survival, morphology, proliferation and/or differentiation of cells of tissues in which 15821 molecules are expressed. Thus, the 15821 molecules can act as novel diagnostic targets and therapeutic agents for controlling disorders involving aberrant activities of these cells.

The 15821 molecules can also act as novel diagnostic targets and therapeutic agents for controlling cellular proliferative and/or differentiative disorders (e.g., hematopoietic neoplastic disorders, carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

15418 Nucleic Acid and Protein

The human 15418 cDNA sequence (FIG. 8; SEQ ID NO: 41), which is approximately 923 nucleotide residues long including non-translated regions, contains a predicted methionine-initiated coding sequence of about 570 nucleotide residues, excluding termination codon (i.e., nucleotide residues 164–733 of SEQ ID NO: 41; also shown in SEQ ID NO: 43). The coding sequence encodes a 190 amino acid protein having the amino acid sequence SEQ ID NO: 42.

Human 15418 contains a predicted dual specificity phosphatase catalytic domain (PF00782) at about amino acid residues 21–159 of SEQ ID NO: 42 and a predicted tyrosine specific protein phosphatase active site (Pfam accession number PS00383) at residues 104–116 of SEQ ID NO: 42.

The human 15418 protein has predicted N-glycosylation sites (Pfam accession number PS00001) at about amino acid residues 53–56 and 163–166 of SEQ ID NO: 42; predicted protein kinase C phosphorylation sites (Pfam accession number PS00005) at about amino acid residues 45–47, 138–140, and 165–167 of SEQ ID NO: 42; a predicted casein kinase II phosphorylation site (Pfam accession number PS00006) located at about amino acid residues 128–131 of SEQ ID NO: 42; and predicted N-myristoylation sites (Pfam accession number PS00008) at about amino acid residues 34–39 and 109–114 of SEQ ID NO: 42.

For general information regarding PFAM identifiers, PS prefix and PF prefix domain identification numbers, refer to Sonnhammer et al. (1997, Protein 28:405–420) and www.psc.edu/general/software/packages/pfam/pfam.html.

The 15418 protein contains a significant number of structural characteristics in common with members of the MAPKP family. For example, the family can contain a first protein of human origin as well as other distinct proteins of human origin, or alternatively, can contain homologues of non-human origin, e.g., MAPKP proteins for any species described in the art. Examples of human MAPKPs that have been described include DUSP1 (MAPKP-1), DUSP2 (PAC-1), DUSP3 (VHR), DUSP4 (HVH2), DUSP5 (HVH3), DUSP6 (MKP-3), and DUSP7 (MKP-X). Members of a family can also have common functional characteristics.

A 15418 polypeptide can include a dual specificity phosphatase catalytic domain (DSPc) domain. As used herein, the term "DSPc domain" refers to a protein domain having an amino acid sequence of about 100–300 amino acid residues in length, preferably, at least about 125–300 amino acids, more preferably about 138 amino acid residues and has a bit score for the alignment of the sequence to the DSPc domain (HMM) of at least 50 or greater, preferably 100 or greater, and more preferably 125 or greater. The DSPc domain has been assigned the PFAM accession PS50054 (genome.wustl.edu/Pfam/html).

In a preferred embodiment, 15418 polypeptide or protein has a DSPc domain or a region which includes at least about 100–300 amino acid residues in length, preferably, at least about 125–300 amino acids, more preferably about 138 amino acid residues and has at least about 60%, 70%, 80%, 90%, 95%, 99%, or 100% homology with a DSPc domain, e.g., the DSPc domain of human 15418 (e.g., residues 21 to 159 of SEQ ID NO: 42).

To identify the presence of a DSPc domain profile in a 15418 receptor, the amino acid sequence of the protein is searched against a database of HMMs (e.g., the Pfam database, release 2.1) using common default parameters such as those found at (www.sanger.ac.uk/Software/Pfaf/HMM_search). For example, the hmmsf program, which is available as part of the HMMER package of search programs, is a family specific default program for P550054 and score of 50 is the default threshold score for determining a hit. For example, using ORFAnalyzer software, a DSPc domain profile was identified in the amino acid sequence of SEQ ID NO: 42 (e.g., amino acids 21–159 of SEQ ID NO: 42). Accordingly, a 15418 protein having at least about 60–70%, more preferably about 70–80%, or about 80–90% homology with the DSPc domain profile of human 15418 is within the scope of the invention.

While not being bound by any particular theory of operation, 15418 protein is, in at least one embodiment, a nuclear protein. In this embodiment, 15418 protein is capable of modulating cell signaling by de-phosphorylating MAPK molecules in the nucleus, whereby, for example, gene transcription can be regulated. In another embodiment, 15418 protein a cytoplasmic protein.

In one embodiment of the invention, a 15418 polypeptide includes at least one DSPc domain. In another embodiment, the 15418 polypeptide includes at least one DSPc domain and at least one tyrosine specific protein phosphatase active site. The 15418 molecules of the present invention can further include one or more of the N-glycosylation, protein kinase C phosphorylation, casein kinase II phosphorylation, and N-myristoylation sites described herein, and preferably comprises most or all of them.

Because the 15418 polypeptides of the invention can modulate 15418-mediated activities, they can be used to develop novel diagnostic and therapeutic agents for 15418-mediated or related disorders, as described below.

As used herein, a "15418 activity," "biological activity of 15418," or "functional activity of 15418," refers to an activity exerted by a 15418 protein, polypeptide or nucleic acid molecule on, for example, a 15418-responsive cell or on a 15418 substrate (e.g., a phosphorylated MAPK protein) as determined in vivo or in vitro. In one embodiment, a 15418 activity is a direct activity, such as association with a 15418 target molecule. A "target molecule" or "binding partner" of a 15418 protein is a molecule (e.g., a protein or nucleic acid) with which the 15418 protein binds or interacts in nature. In an exemplary embodiment, such a target molecule is a 15418 receptor or a MAPK protein. A 15418 activity can also be an indirect activity, such as a cellular signaling activity mediated by interaction of the 15418 protein with a 15418 receptor or with a MAPK protein.

15418 is expressed in at least skeletal muscle and testis tissues in adult humans, and is expressed in one or both of spleen and liver tissues in human fetuses.

In skeletal muscle, 15418 can be involved in both normal and aberrant physiological processes. By way of example, 15418 can modulate muscle cell growth, proliferation, and differentiation that occurs in response to occurrence of hormones (e.g., various adrenal hormones) in the bloodstream or in muscle tissue. Modulating expression, activity, or both of 15418 can modulate the rate or extent of muscle mass development. 15418 can also have a role in development or progression of muscular dystrophy (e.g., Duchenne, Becker's, or limb muscle girdle) in a human patient. These conditions can be diagnosed or prognosticated by assessing expression or activity of 15418 in a skeletal muscle tissue of a patient. Furthermore, modulating expression or activity of 15418 in a skeletal muscle tissue of a patient can alleviate or reverse these conditions.

In testis tissue, 15418 can be involved in both normal and aberrant physiological processes. By way of example, 15418 can modulate spermatogenesis, development and differentiation of normal testis tissue, and development, growth, and metastasis of hyperplastic testis tissue. 15418 can modulate these processes by modulating cell signaling and protein phosphorylation processes associated with occurrence of hormones (e.g., adrenal hormones) in the bloodstream and testis tissue. Disorders in which 15418 can have a role include infertility, sperm motility disorders, testicular tumor development, growth, and metastasis, hypogonadism (endocrinologic, gametogenic, or both), and growth and developmental disorders associated with testicular hormones (e.g., testosterone). These conditions can be diagnosed or prognosticated by assessing expression or activity of 15418 in a testis tissue of a patient. Furthermore, modulating expression or activity of 15418 in a testis tissue of a patient can alleviate or reverse these conditions.

In fetal tissues such as liver and spleen, 15418 can be involved in normal and aberrant developmental processes. By way of example, 15418 can influence tissue growth and differentiation in a human embryo or fetus. Modulating 15418 expression, activity, or both can modulate the rate and extent of organogenesis. Modulation of 15418 expression or activity can also modulate the rate and extent of differentiation of tissues within an organ (e.g., formation of the hepatic cellular plate, bile-collecting space, and lymph and blood flow systems of liver lobules or the capillaries, pulp cords, and venous sinuses of the spleen). Developmental disorders in which 15418 can have a role include numerous types of birth defects (e.g., mental retardation and congenital defects of liver and spleen formation), jaundice, and congenital immunodeficiency disorders. 15418 can also have a role in disorders associated with aberrant regenerative capacity, such as aberrant wound healing, liver fibrosis, and peripheral nerve deficit. These conditions can be diagnosed or prognosticated by assessing expression or activity of 15418 in a tissue of a patient. Furthermore, modulating expression or activity of 15418 in a tissue of a patient can alleviate or reverse these conditions.

When 15418 is expressed in neuronal tissues, it can modulate growth and interconnection (e.g., synapse formation) of neurons. Because injured neurons normally do not regenerate at most body locations, ability of 15418 to modulate neuronal growth and interconnection can be used to enhance healing of damage caused to neuronal tissue by traumatic injury (e.g., mechanical or ischemic damage) or chronic injury (e.g., neurodegeneration or formation of abnormal neuronal structures such as neurofibrillary tangles associated with Alzheimer's disease). This ability can also be used to enhance neuronal growth and interconnection in non-injured tissue, enhancing processes such as intellectual learning, cognition, and memory. Assessment of expression or activity of 15418 can be used to diagnose a neuronal disorder in a human patient or to predict the likelihood that a patient will develop such a disorder. Modulating expression, activity, or both, of 15418 can alleviate, inhibit, or reverse occurrence of such disorders in a patient.

Expression of 15418 in tissues which are influenced by adrenocortical hormones (i.e., including mineralocorticoids, glucocorticoids, and androgens) indicates that 15418 can have a role in regulation of metabolic and developmental processes mediated by adrenocortical hormones. Among other functions, adrenocortical hormones modulate development of skeletal muscle, maturation and differentiation of gonadal tissues (i.e., ovary and testis tissues), glucose metabolism in the liver and skeletal muscle, inflammation, development of secondary sexual characteristics, extra-adrenal testosterone production, and mobilization of fatty acids. In addition, a global defect in 15418 expression or activity can exhibit the characteristic symptoms of adrenal insufficiency, even if systemic levels of adrenocortical hormones are normal or nearly normal. Assessing expression or activity of 15418 in a tissue that normally exhibits a response to the presence of an adrenocortical hormone can indicate whether a disorder (apparent Addison's disease) or a physiological state (e.g., delayed or incomplete sexual development) is attributable to aberrant production of an adrenocortical hormone or to a deficiency in the affected tissue's ability to react to normal production of the hormone. Modulating 15418 expression or activity in a tissue can affect the reactivity of the tissue to occurrence in the patient of an adrenocortical hormone. Disorders in which aberrant 15418 expression or activity can have a role include diabetes, insulin resistance, hyperinsulinism, Addison's disease, Cushing's syndrome, aldosteronism, adrenogenital syndrome, and disorders in which the symptoms of one of the preceding disorders occur, but in which levels of adrenocortical hormones are not abnormal.

The 15418 molecules of the present invention are predicted to have similar biological activities as MAPKP family members. For example, the 15418 proteins of the present invention can have one or more of the following activities:

(1) catalyzing interconversion of the phosphorylated and de-phosphorylated forms of a serine, threonine, or tyrosine residue of a MAPK protein (e.g., by catalyzing cleavage of a covalent bond between the amino acid residue and a phosphate moiety;

(2) modulating cell signaling;

(3) modulating cell growth;

(4) modulating cell differentiation;

(5) modulating tumorigenesis;

(6) modulating entry of a cell into the cell cycle;

(7) modulating progression of a cell through the cell cycle;

(8) modulating mitogenesis;

(9) modulating cell motility;

(10) modulating a cell-to-cell interaction;

(11) modulating cell metabolism;

(12) modulating gene transcription;

(13) modulating an immune response;

(14) modulating a cellular response to an adrenocortical hormone;

(15) modulating skeletal muscle development;

(16) modulating development or progression of muscular dystrophy;

(17) modulating spermatogenesis;

(18) modulating fertility;

(19) modulating tumorigenesis;

(20) modulating tumor growth;

(21) modulating tumor metastasis;

(22) modulating a testosterone-associated disorder;

(23) modulating tissue growth in an embryo or fetus;

(24) modulating tissue differentiation in an embryo or fetus;

(25) modulating organogenesis in an embryo or fetus;

(26) modulating wound healing;

(27) modulating neuronal growth; and

(28) modulating neuronal interconnection.

Thus, 15418 molecules described herein can act as novel diagnostic targets and therapeutic agents for prognosticating, diagnosing, preventing, inhibiting, alleviating, or curing MAPKP-related disorders.

Other activities, as described below, include the ability to modulate function, survival, morphology, proliferation and/or differentiation of cells of tissues in which 15418 molecules are expressed. Thus, the 15418 molecules can act as novel diagnostic targets and therapeutic agents for controlling disorders involving aberrant activities of these cells.

The 15418 molecules can also act as novel diagnostic targets and therapeutic agents for controlling cellular proliferative and/or differentiative disorders (e.g., hematopoietic neoplastic disorders, carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer," "hyperproliferative" and "neoplastic" refer to cells having the capacity for autonomous growth, i.e., an abnormal state or condition characterized by rapidly proliferating cell growth. Hyperproliferative and neoplastic disease states can be categorized as pathologic, i.e., characterizing or constituting a disease state, or can be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting eye, lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas (e.g., uveal melanoma). Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. The disorders can arise from poorly differentiated acute leukemias, e.g., erythroblastic leukemia and acute megakaryoblastic leukemia. Exemplary myeloid disorders include, but are not limited to, acute promyeloid leukemia, acute myelogenous leukemia and chronic myelogenous leukemia (reviewed in Vaickus, 1991, Crit. Rev. Oncol./Hemotol. 11:267–297); lymphoid malignancies include, but are not limited to acute lymphoblastic leukemia which includes B-lineage ALL and T-lineage ALL, chronic lymphocytic leukemia, prolymphocytic leukemia, hairy cell leukemia, and Waldenstrom's macroglobulinemia. Additional forms of malignant lymphomas include, but are not limited to non-Hodgkin lymphoma and variants thereof, peripheral T cell lymphomas, adult T cell leukemia/lymphoma, cutaneous T-cell lymphoma, large granular lymphocytic leukemia, Hodgkin's disease and Reed-Sternberg disease.

The 69087 protein, 15821 protein, 15418 protein, fragments of these, and derivatives and other variants of the sequences in SEQ ID NOs: 2, 22, and 42 are collectively referred to as "polypeptides or proteins of the invention," "69087 polypeptides or proteins," "15821 polypeptides or proteins," or "15418 polypeptides or proteins." Nucleic acid molecules encoding such polypeptides or proteins are collectively referred to as "nucleic acids of the invention," "69087 nucleic acids," "15821 nucleic acids," or "15418 nucleic acids." "69087 molecules" refer to 69087 nucleic acids, polypeptides, and antibodies. "15821 molecules" refer to 15821 nucleic acids, polypeptides, and antibodies. "15418 molecules" refer to 15418 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5'- and/or 3'-ends of the nucleic acid) in the genomic DNA of the organism from which the nucleic acid is derived. For example, in various embodiments, the isolated nucleic acid molecule can contain less than about 5 kilobases, 4 kilobases, 3 kilobases, 2 kilobases, 1 kilobase, 0.5 kilobase or 0.1 kilobase of 5'- and/or 3'-nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in available references (e.g., Current Protocols in Molecular Biology, John Wiley & Sons, N.Y., 1989, 6.3.1–6.3.6). Aqueous and non-aqueous methods are described in that reference and either can be used. A preferred example of stringent hybridization conditions are hybridization in 6× sodium chloride/sodium citrate (SSC) at about 45° C., followed by one or more washes in 0.2×SSC, 0.1% (w/v) SDS at 50° C. Another example of stringent hybridization conditions are hybridization in 6×SSC at about 45° C., followed by one or more washes in 0.2×SSC, 0.1% (w/v) SDS at 55° C. A further example of stringent hybridization conditions are hybridization in 6×SSC at about 45° C., followed by one or more washes in 0.2×SSC, 0.1% (w/v) SDS at 60° C. Preferably, stringent hybridization conditions are hybridization in 6×SSC at about 45° C., followed by one or more washes in 0.2×SSC, 0.1% (w/v) SDS at 65° C. Particularly preferred stringency conditions (and the conditions that should be used if the practitioner is uncertain about what conditions should be applied to determine if a molecule is within a hybridization limitation of the invention) are 0.5 molar sodium phosphate, 7% (w/v) SDS at 65° C., followed by one or more washes at 0.2×SSC, 1% (w/v) SDS at 65° C. Preferably, an isolated nucleic acid molecule of the invention that hybridizes under stringent conditions to the sequence of one of SEQ ID NOs: 1, 3, 21, 23, 41, and 43 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 69087, 15821, or 15418 protein, preferably a mammalian 69087, 15821, or 15418 protein, and can further include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 69087, 15821, or 15418 protein having less than about 30%, 20%, 10% and more preferably 5% (by dry weight), of non-69087, non-15821, or non-15418 protein (also referred to herein as a "contaminating protein"), or of chemical precursors or non-69087, non-15821, or non-15418 chemicals. When the 69087, 15821, or 15418 protein or a biologically active portion of one of these is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 69087, 15821, or 15418 (e.g., the sequence of one of SEQ ID NOs: 1, 3, 21, 23, 41, and 43) without abolishing or, more preferably, without substantially altering a biological activity, whereas an "essential" amino acid residue results in such a change. For example, amino acid residues that are conserved among the polypeptides of the present invention, e.g., those present in the pkinase domain are predicted to be particularly non-amenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 69087, 15821, or 15418 protein is preferably replaced with another amino acid residue from the same side chain family. Alternatively, in another embodiment, mutations can be introduced randomly along all or part of a 69087, 15821, or 15418 coding sequence, such as by saturation mutagenesis, and the resultant mutants can be screened for 69087, 15821, or 15418 biological activity to identify mutants that retain activity. Following mutagenesis of one of SEQ ID NOs: 1, 3, 21, 23, 41, and 43, the encoded protein can be expressed recombinantly and the activity of the protein can be determined.

As used herein, a "biologically active portion" of a 69087, 15821, or 15418 protein includes a fragment of a 69087, 15821, or 15418 protein that participates in an interaction between a 69087, 15821, or 15418 molecule and a non-69087, non-15821, or non-15418 molecule. Biologically active portions of a 69087, 15821, or 15418 proteins include peptides comprising amino acid sequences sufficiently homologous to or derived from the amino acid sequence of the 69087, 15821, or 15418 protein, e.g., the amino acid sequence shown in one of SEQ ID NOs: 2, 22, and 42, which include less amino acids than the full length 69087, 15821, or 15418 proteins, and exhibit at least one activity of a 69087, 15821, or 15418 protein. Typically, biologically active portions comprise a domain or motif with at least one activity of the 69087, 15821, or 15418 protein, e.g., a domain or motif capable of catalyzing an activity described herein, such as (for 69087) covalent addition of a phosphate moiety to a protein amino acid residue (e.g., to a serine or threonine hydroxyl group of a GPCR).

A biologically active portion of a 69087, 15821, or 15418 protein can be a polypeptide that is, for example, 10, 25, 50, 100, 150, 200, 300, 400, 500, 600, 700, 800, or 900 or more amino acids in length. Biologically active portions of a 69087, 15821, or 15418 protein can be used as targets for developing agents that modulate a 69087-mediated activity, a 15821-mediated activity, or a 15418-mediated activity, e.g., a biological activity described herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 69087 amino acid sequence of SEQ ID NO: 2, 100 amino acid residues, preferably at least 200, 300, 400, or 500 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970, J. Mol. Biol. 48:444–453) algorithm which has been incorporated into the GAP program in the GCG software package (available at www.gcg.com), using either a BLOSUM 62 matrix or a PAM250 matrix, and a gap weight of 16, 14, 12, 10, 8, 6, or 4 and a length weight of 1, 2,3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989, CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990, J. Mol. Biol. 215:403–410). BLAST nucleotide searches can be performed with the NBLAST program, score=100, wordlength=12 to obtain nucleotide sequences homologous to 69087, 15821, or 15418 nucleic acid molecules of the invention. BLAST protein searches can be performed with the XBLAST program, score=50, wordlength=3 to obtain amino acid sequences homologous to 69087, 15821, or 15418 protein molecules of the invention. To obtain gapped alignments for comparison purposes, gapped BLAST can be utilized as described in Altschul et al. (1997, Nucl. Acids Res. 25 :3389–l 3402). When using BLAST and gapped BLAST programs, the default parameters of the respective programs (e.g., XBLAST and NBLAST) can be used. See <www.ncbi.nlm.nih.gov>.

"Malexpression or aberrant expression," as used herein, refers to a non-wild-type pattern of gene expression, at the RNA or protein level. It includes: expression at non-wild-type levels, i.e., over- or under-expression; a pattern of expression that differs from wild-type in terms of the time or stage at which the gene is expressed, e.g., increased or decreased expression (as compared with wild-type) at a predetermined developmental period or stage; a pattern of expression that differs from wild-type in terms of decreased expression (as compared with wild-type) in a predetermined cell type or tissue type; a pattern of expression that differs from wild-type in terms of the splicing size, amino acid sequence, post-transitional modification, or biological activity of the expressed polypeptide; a pattern of expression that differs from wild-type in terms of the effect of an environmental stimulus or extracellular stimulus on expression of the gene, e.g., a pattern of increased or decreased expression (as compared with wild-type) in the presence of an increase or decrease in the strength of the stimulus.

"Subject," as used herein, can refer to a mammal, e.g., a human, or to an experimental or animal or disease model. The subject can also be a non-human animal, e.g., a horse, cow, goat, or other domestic animal.

A "purified preparation of cells," as used herein, refers to, in the case of plant or animal cells, an in vitro preparation of cells and not an entire intact plant or animal. In the case of cultured cells or microbial cells, it consists of a preparation of at least 10%, and more preferably, 50% of the subject cells.

Various aspects of the invention are described in further detail below.

Isolated Nucleic Acid Molecules

In one aspect, the invention provides, an isolated or purified, nucleic acid molecule that encodes a 69087, 15821, or 15418 polypeptide described herein, e.g., a full-length 69087, 15821, or 15418 protein or a fragment of one of these, e.g., a biologically active portion of 69087, 15821, or 15418 protein. Also included is a nucleic acid fragment suitable for use as a hybridization probe, which can be used, e.g., to a identify nucleic acid molecule encoding a polypeptide of the invention, 69087 mRNA, 15821 mRNA, or 15418 mRNA, and fragments suitable for use as primers, e.g., PCR primers for the amplification or mutation of nucleic acid molecules.

In one embodiment, an isolated nucleic acid molecule of the invention includes the nucleotide sequence shown in one of SEQ ID NOs: 1, 21, or 41, or a portion of one of these nucleotide sequences.

In one embodiment, the nucleic acid molecule includes sequences encoding the human 69087 protein (i.e., "the coding region," from nucleotides 291–1949 of SEQ ID NO: 1), as well as 5'-non-translated sequences (nucleotides 1–290 of SEQ ID NO: 1) or 3'-non-translated sequences (nucleotides 1950–2198 of SEQ ID NO: 1). Alternatively, the nucleic acid molecule can include only the coding region of SEQ ID NO: 1 (e.g., nucleotides 291–1949, corresponding to SEQ ID NO: 3) and, e.g., no flanking sequences which normally accompany the subject sequence. In another embodiment, the nucleic acid molecule encodes a sequence corresponding to the 553 amino acid residue protein of SEQ ID NO: 2.

In another embodiment, the nucleic acid molecule includes sequences encoding the human 15821 protein (i.e., "the coding region," from nucleotides 235–1926 of SEQ ID NO: 21), as well as 5'-non-translated sequences (nucleotides 1–234 of SEQ ID NO: 21) or 3'-non-translated sequences (nucleotides 1927–3003 of SEQ ID NO: 21). Alternatively, the nucleic acid molecule can include only the coding region of SEQ ID NO: 21(e.g., nucleotides 235–1926, corresponding to SEQ ID NO: 23) and, e.g., no flanking sequences which normally accompany the subject sequence. In another embodiment, the nucleic acid molecule encodes a sequence corresponding to the 564 amino acid residue protein of SEQ ID NO: 22.

In still another embodiment, the nucleic acid molecule includes sequences encoding the human 15418 protein (i.e., "the coding region," from nucleotides 164–733 of SEQ ID NO: 41), as well as 5'-non-translated sequences (nucleotides 1–165 of SEQ ID NO: 41) or 3'-non-translated sequences (nucleotides 734–923 of SEQ ID NO: 41). Alternatively, the nucleic acid molecule can include only the coding region of SEQ ID NO: 41 (e.g., nucleotides 164–733, corresponding to SEQ ID NO: 43) and, e.g., no flanking sequences which normally accompany the subject sequence. In another embodiment, the nucleic acid molecule encodes a sequence corresponding to the 190 amino acid residue protein of SEQ ID NO: 42.

In another embodiment, an isolated nucleic acid molecule of the invention includes a nucleic acid molecule which is a complement of the nucleotide sequence shown in one of SEQ ID NOs: 1, 3, 21, 23, 41, and 43, and a portion of any of these sequences. In other embodiments, the nucleic acid molecule of the invention is sufficiently complementary to the nucleotide sequence shown in one of SEQ ID NOs: 1, 3, 21, 23, 41, and 43 that it can hybridize with a nucleic acid having that sequence, thereby forming a stable duplex.

In one embodiment, an isolated nucleic acid molecule of the invention includes a nucleotide sequence which is at least about 60%, 65%, 70%, 75%, 80%, 85%, 90%, 91%, 92%, 93%, 94%, 95%, 96%, 97%, 98%, or 99% or more homologous to the entire length of the nucleotide sequence shown in one of SEQ ID NOs: 1, 3, 21, 23, 41, and 43, and a portion, preferably of the same length, of any of these nucleotide sequences.

Nucleic Acid Fragments

A nucleic acid molecule of the invention can include only a portion of the nucleic acid sequence of one of SEQ ID NOs: 1, 3, 21, 23, 41, and 43. For example, such a nucleic acid molecule can include a fragment that can be used as a probe or primer or a fragment encoding a portion of a 69087, 15821, or 15418 protein, e.g., an immunogenic or biologically active portion of a 69087, 15821, or 15418 protein. A fragment can comprise nucleotides corresponding to residues 191–454 of SEQ ID NO: 2, which encodes a pkinase domain of human 69087 or nucleotides corresponding to residues 55–78 or 162–176 of SEQ ID NO: 2, each of which encodes an RGS domain of human 69087. A fragment can instead comprise nucleotides corresponding to residues 483–528 of SEQ ID NO: 22, which encodes a RING finger domain of human 15821. Alternatively, a fragment can comprise nucleotides corresponding to residues 21–159 of SEQ ID NO: 42, which encodes a DSPc domain of human 15418. The nucleotide sequence determined from the cloning of the 69087, 15821, or 15418 gene facilitates generation of probes and primers for use in identifying and/or cloning other 69087, 15821, or 15418 family members, or fragments thereof, as well as 69087, 15821, or 15418 homologues, or fragments thereof, from other species.

In another embodiment, a nucleic acid includes a nucleotide sequence that includes part, or all, of the coding region and extends into either (or both) the 5'- or 3'-non-coding region. Other embodiments include a fragment that includes a nucleotide sequence encoding an amino acid fragment described herein. Nucleic acid fragments can encode a specific domain or site described herein or fragments thereof, particularly fragments thereof that are at least about 250 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein.

69087, 15821, and 15418 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of one of SEQ ID NOs: 1, 3, 21, 23, 41, and 43, and a naturally occurring allelic variant or mutant of SEQ ID NOs: 1, 3, 21, 23, 41, and 43.

In a preferred embodiment the nucleic acid is a probe which is at least 5 or 10, and less than 200, more preferably less than 100, or less than 50, base pairs in length. It should be identical, or differ by 1, or fewer than 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid that encodes a pkinase domain at about amino acid residues 191 to 454 of SEQ ID NO: 2 or a predicted RGS domain at about amino acid residues 55 to 78 or 162 to 176 of SEQ ID NO: 2. Alternatively, a probe or primer can be derived from the sense or anti-sense strand of a nucleic acid that encodes a RING finger domain at about amino acid residues 483 to 528 of SEQ ID NO: 22 or the predicted transmembrane domain at about amino acid residues 470 to 482 of SEQ ID NO: 22. As another alternative, a probe or primer can be derived from the sense or anti-sense strand of a nucleic acid that encodes a DSPc domain at about amino acid residues 21 to 159 of SEQ ID NO: 42 or the predicted tyrosine specific protein phosphatase active site domain at about amino acid residues 104 to 114 of SEQ ID NO: 42.

In another embodiment a set of primers is provided, e.g., primers suitable for use in a PCR, which can be used to amplify a selected region of a 69087, 15821, or 15418 sequence. The primers should be at least 5, 10, or 50 base pairs in length and less than 100, or less than 200, base pairs in length. The primers should be identical, or differs by one base from a sequence disclosed herein or from a naturally occurring variant. Primers suitable for amplifying all or a portion of any of the following regions are provided: e.g., one or more a pkinase domain and the predicted transmembrane domain, as defined above relative to SEQ ID NOs: 2, 22, and 42.

A nucleic acid fragment can encode an epitope bearing region of a polypeptide described herein.

A nucleic acid fragment encoding a "biologically active portion of a 69087, 15821, or 15418 polypeptide" can be prepared by isolating a portion of the nucleotide sequence of one of SEQ ID NOs: 1, 3, 21, 23, 41, and 43, which encodes a polypeptide having a 69087, 15821, or 15418 biological activity (e.g., the biological activities of the 69087, 15821, and 15418 proteins are described herein), expressing the encoded portion of the 69087, 15821, or 15418 protein (e.g., by recombinant expression in vitro) and assessing the activity of the encoded portion of the 69087, 15821, or 15418 protein. For example, a nucleic acid fragment encoding a biologically active portion of 69087 includes a pkinase domain, e.g., amino acid residues 191 to 454 of SEQ ID NO: 2, a nucleic acid fragment encoding a biologically active portion of 15821 includes a RING finger domain, e.g., amino acid residues 483 to 528 of SEQ ID NO: 22, and a nucleic acid fragment encoding a biologically active portion of 15418 includes a DSPc domain, e.g., amino acid residues 21 to 159 of SEQ ID NO: 42. A nucleic acid fragment encoding a biologically active portion of a 69087, 15821, or 15418 polypeptide can comprise a nucleotide sequence that is greater than 25 or more nucleotides in length.

In one embodiment, a nucleic acid includes one that has a nucleotide sequence which is greater than 260, 300, 400, 500, 600, 700, 800, 900, 1000, 1100, 1200, 1300, 1400, 1500, 2000, 2500, or 3000 or more nucleotides in length and that hybridizes under stringent hybridization conditions with a nucleic acid molecule having the sequence of one of SEQ ID NOs: 1, 3, 21, 23, 41, and 43.

Nucleic Acid Variants

The invention further encompasses nucleic acid molecules having a sequence that differs from the nucleotide sequence shown in one of SEQ ID NOs: 1, 3, 21, 23, 41, and 43. Such differences can be attributable to degeneracy of the genetic code (i.e., differences which result in a nucleic acid that encodes the same 69087, 15821, or 15418 proteins as those encoded by the nucleotide sequences disclosed herein). In another embodiment, an isolated nucleic acid molecule of the invention encodes a protein having an amino acid sequence which differs by at least 1, but by fewer than 5, 10, 20, 50, or 100, amino acid residues from one of SEQ ID NOs: 2, 22, and 42. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. For example, the nucleic acid can be one in which at least one codon, at preferably at least 10%, or 20% of the codons has been altered such that the sequence is optimized for expression in *E. coli,* yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid has a sequence that differs from that of one of SEQ ID NOs: 1, 3, 21, 23, 41, and 43, e.g., as follows: by at least one, but by fewer than 10, 20, 30, or 40, nucleotide residues; or by at least one but by fewer than 1%, 5%, 10% or 20% of the nucleotide residues in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in one of SEQ ID NOs: 1, 3, 21, 23, 41, and 43, or a fragment of one of these sequences. Such nucleic acid molecules can readily be identified as being able to hybridize under stringent conditions, to the nucleotide sequence shown in one of SEQ ID NOs: 1, 3, 21, 23, 41, and 43, or a fragment of one of these sequences. Nucleic acid molecules corresponding to orthologs, homologs, and allelic variants of the 69087, 15821, or 15418 cDNAs of the invention can further be isolated by mapping to the same chromosome or locus as the corresponding gene.

Preferred variants include those that are correlated with any of the 69087, 15821, or 15418 biological activities described herein, e.g., catalyzing formation of a covalent bond between an amino acid residue of a protein (e.g., a serine or threonine residue) and a phosphate moiety for 69087.

Allelic variants of 69087, 15821, or 15418 (e.g., human 69087, 15821, or 15418) include both functional and non-functional proteins. Functional allelic variants are naturally occurring amino acid sequence variants of the 69087, 15821, or 15418 proteins within a population that maintain the ability to mediate any of the corresponding biological activities described herein.

Functional allelic variants will typically contain only conservative substitution of one or more amino acids of one of SEQ ID NOs: 2, 22, and 42 or substitution, deletion or insertion of non-critical residues in non-critical regions of the protein. Non-functional allelic variants are naturally-occurring amino acid sequence variants of the 69087, 15821, or 15418 (e.g., human 69087, 15821, or 15418) protein within a population that do not have the ability to mediate any of the corresponding biological activities described herein. Non-functional allelic variants will typically contain a non-conservative substitution, a deletion, or insertion, or premature truncation of the amino acid sequence of one of SEQ ID NOs: 2, 22, and 42 or a substitution, insertion, or deletion in critical residues or critical regions of the protein.

Moreover, nucleic acid molecules encoding other 69087, 15821, or 15418 family members and, thus, which have a nucleotide sequence which differs from the 69087, 15821, or 15418 sequences of SEQ ID NOs: 1, 3, 21, 23, 41, and 43 are within the scope of the invention.

Antisense Nucleic Acid Molecules, Ribozymes and Modified Nucleic Acid Molecules

In another aspect, the invention features, an isolated nucleic acid molecule that is antisense to 69087, 15821, or 15418. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 69087, 15821, or 15418 coding strand, or to only a portion thereof (e.g., the coding region of human 69087 corresponding to SEQ ID NO: 3, the coding region of human 15821 corresponding to SEQ ID NO: 23, or the coding region of human 15814 corresponding to SEQ ID NO: 43). In another embodiment, the antisense nucleic acid molecule is antisense to a "non-coding region" of the coding strand of a nucleotide sequence encoding 69087, 15821, or 15418 (e.g., the 5'- and 3'-non-translated regions).

An antisense nucleic acid can be designed such that it is complementary to the entire coding region of 69087, 15821, or 15418 mRNA, but more preferably is an oligonucleotide that is antisense to only a portion of the coding or non-coding region of the mRNA. For example, the antisense oligonucleotide can be complementary to the region surrounding the translation start site of 69087, 15821, or 15418 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, or 80 or more nucleotide residues in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 69087 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., 1987, Nucl. Acids. Res. 15:6625–6641). The antisense nucleic acid molecule can also comprise a 2'-o-methylribonucleotide (Inoue et al., 1987, Nucl. Acids Res. 15:6131–6148) or a chimeric RNA-DNA analogue (Inoue et al., 1987, FEBS Lett. 215:327–330).

In still another embodiment, an antisense nucleic acid of the invention is a ribozyme. A ribozyme having specificity for a nucleic acid of the invention can include one or more sequences complementary to the nucleotide sequence of a 69087, 15821, or 15418 cDNA disclosed herein (i.e., one of SEQ ID NOs: 1, 3, 21, 23, 41, and 43), and a sequence having known catalytic sequence responsible for mRNA cleavage (see, for example, U.S. Pat. No. 5,093,246 or Haselhoff et al. (1988, Nature 334:585–591). For example, a derivative of a Tetrahymena L-19 IVS RNA can be constructed in which the nucleotide sequence of the active site is complementary to the nucleotide sequence to be cleaved in a 69087-, 15821-, or 15418-encoding mRNA (e.g., U.S. Pat. Nos. 4,987,071; and 5,116,742). Alternatively, 69087, 15821, or 15418 mRNA can be used to select a catalytic RNA having a specific ribonuclease activity from a pool of RNA molecules (e.g., Bartel et al., 1993, Science 261:1411–1418).

69087, 15821, or 15418 gene expression can be inhibited by targeting nucleotide sequences complementary to the regulatory region of the corresponding gene (e.g., the 69087, 15821, or 15418 promoter and/or enhancers) to form triple helical structures that prevent transcription of the gene in target cells (Helene, 1991, Anticancer Drug Des. 6:569–584; Helene, et al., 1992, Ann. N.Y. Acad. Sci. 660:27–36; Maher, 1992, Bioassays 14:807–815). The potential sequences that can be targeted for triple helix formation can be increased by creating a so-called "switchback" nucleic acid molecule. Switchback molecules are synthesized in an alternating 5' to 3', 3' to 5' manner, such that they hybridize with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 69087, 15821, or 15418 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (Hyrup et al., 1996, Bioorg. Med. Chem. 4:5–23). As used herein, the terms "peptide nucleic acid" (PNA) refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996, supra; Perry-O'Keefe et al., Proc. Natl. Acad. Sci. USA 93:14670–14675).

PNAs of 69087, 15821, or 15418 nucleic acid molecules can be used in therapeutic and diagnostic applications. For example, PNAs can be used as antisense or anti-gene agents for sequence-specific modulation of gene expression by, for example, inducing transcription or translation arrest or inhibiting replication. PNAs of 69087, 15821, or 15418 nucleic acid molecules can also be used in the analysis of single base pair mutations in a gene, (e.g., by PNA-directed PCR clamping); as 'artificial restriction enzymes' when used in combination with other enzymes, (e.g., S1 nucleases, as described in Hyrup et al., 1996, supra); or as probes or primers for DNA sequencing or hybridization (Hyrup et al., 1996, supra; Perry-O'Keefe, supra).

In other embodiments, the oligonucleotide can include other appended groups such as peptides (e.g., for targeting host cell receptors in vivo), or agents facilitating transport across the cell membrane (e.g., Letsinger et al., 1989, Proc. Natl. Acad. Sci. USA 86:6553–6556; Lemaitre et al., 1987, Proc. Natl. Acad. Sci. USA 84:648–652; PCT publication number WO 88/09810) or the blood-brain barrier (see, e.g., PCT publication number WO 89/10134). In addition, oligonucleotides can be modified with hybridization-triggered cleavage agents (e.g., Krol et al., 1988, Bio-Techniques 6:958–976) or intercalating agents (e.g., Zon, 1988, Pharm. Res. 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 69087, 15821, or 15418 nucleic acid of the invention, two complementary regions, one having a fluorophore and the other having a quencher, such that the molecular beacon is useful for quantitating the presence of the 69087, 15821, or 15418 nucleic acid of the invention in a sample. Molecular beacon nucleic acids are described, for example, in U.S. Pat. Nos. 5,854,033, 5,866,336, and 5,876,930.

Isolated Polypeptides

In another aspect, the invention features, an isolated 69087, 15821, or 15418 protein, or fragment, e.g., a biologically active portion, for use as immunogens or antigens to raise or test (or more generally to bind) anti-69087, anti-15821, or anti-15418 antibodies. 69087, 15821, or 15418 protein can be isolated from cells or tissue sources using standard protein purification techniques. 69087, 15821, or 15418 protein or fragments of one of these can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present when expressed in a native cell.

In a preferred embodiment, a 69087 polypeptide has one or more of the following characteristics:

(1) it catalyzes formation of a covalent bond within or between an amino acid residue of a GPCR and a phosphate moiety;

(2) it modulates cell signaling;

(3) it modulates cell growth;

(4) it modulates cell differentiation;

(5) it modulates tumorigenesis;

(6) it modulates entry of a cell into the cell cycle;

(7) it modulates progression of a cell through the cell cycle;

(8) it modulates mitogenesis;

(9) it modulates cell motility;

(10) it modulates a cell-to-cell interaction;

(11) it modulates cell metabolism;

(12) it modulates gene transcription;

(13) it modulates cardiac function;

(14) it modulates transmission of nerve impulses;

(15) it modulates olfaction;

(16) it modulates vision;

(17) it modulates photoreceptor signaling;

(18) it modulates uncoupling of receptors and heterotrimeric G-proteins;

(19) it modulates development of color-blindness;

(20) it modulates susceptibility to impaired night vision;

(21) it modulates susceptibility to blindness;

(22) it modulates susceptibility to retinitis pigmentosa;

(23) it modulates susceptibility to macular degeneration;

(24) it modulates photoreceptor cell apoptosis;

(25) it modulates photoreceptor cell differentiation;

(26) it modulates visual pigmentation;

(27) it modulates photoreceptor desensitization; (28) it has a molecular weight, amino acid composition or other physical characteristic of a 69087 protein of SEQ ID NO: 2;

(29) it has an overall sequence similarity (identity) of at least 60–65%, preferably at least 70%, more preferably at least 75, 80, 85, 86, 87, 88, 89, 90, 91, 92, 93, 94, 95, 96, 97, 98, or 99% or more, with a portion of SEQ ID NO: 2; and

(30) it has a pkinase domain which is preferably about 70%, 80%, 90%, 95%, 96%, 97%, 98%, 99% or higher, identical with amino acid residues 191–454 of SEQ ID NO: 2.

In another preferred embodiment, a 15821 polypeptide has one or more of the following characteristics:

(1) it binds with a cytoplasmic cell signaling mediator;

(2) it binds with a nuclear cell signaling mediator;

(3) it binds with a nuclear membrane protein to form a signaling complex;

(4) it modulates cell signaling;

(5) it modulates cell growth;

(6) it modulates cell differentiation;

(7) it modulates tumorigenesis;

(8) it modulates entry of a cell into the cell cycle;

(9) it modulates progression of a cell through the cell cycle;

(10) it modulates mitogenesis;

(11) it modulates cell motility;

(12) it modulates a cell-to-cell interaction;

(13) it modulates cell metabolism;

(14) it modulates gene transcription;

(15) it modulates an immune response;

(16) it modulates apoptosis;

(17) it modulates neural degeneration;

(18) it modulates formation of inclusion bodies;

(19) it modulates proteosome activities;

(20) it modulates protein clearance;

(21) it modulates metabolic stress;

(22) it modulates protein translation;

(23) it modulates transcription; (24) modulating vesicle transport;

(25) it modulates protein localization;

(25) it modulates cytoskeleton integrity;

(26) it has a molecular weight, amino acid composition or other physical characteristic of a 15821 protein of SEQ ID NO: 22;

(27) it has an overall sequence similarity (identity) of at least 60–65%, preferably at least 70%, more preferably at least 75, 80, 85, 86, 87, 88, 89, 90, 91, 92, 93, 94, 95, 96, 97, 98, or 99% or more, with a portion of SEQ ID NO: 22;

(28) it has a transmembrane domain which is preferably about 70%, 80%, 90%, 95%, 96%, 97%, 98%, or 99% or more, identical with amino acid residues 470–482 of SEQ ID NO: 22;

(29) it has at least one non-transmembrane domain which is preferably about 70%, 80%, 90%, 95%, 96%, 97%, 98%, or 99% or more, identical with amino acid residues 1–469 of SEQ ID NO: 22;

(30) it has at least one non-transmembrane domain which is preferably about 70%, 80%, 90%, 95%, 96%, 97%, 98%, or 99% or more, identical with amino acid residues 483–564 of SEQ ID NO: 22; or

(31) it has a RING finger domain which is preferably about 70%, 80%, 90%, 95%, 96%, 97%, 98%, 99% or higher, identical with amino acid residues 483–528 of SEQ ID NO: 22.

In still another preferred embodiment, a 15418 polypeptide has one or more of the following characteristics:

(1) it catalyzes interconversion of the phosphorylated and de-phosphorylated forms of a serine, threonine, or tyrosine residue of a MAPK protein (e.g., by catalyzing cleavage of a covalent bond between the amino acid residue and a phosphate moiety;

(2) it modulates cell signaling;

(3) it modulates cell growth;

(4) it modulates cell differentiation;

(5) it modulates tumorigenesis;

(6) it modulates entry of a cell into the cell cycle;

(7) it modulates progression of a cell through the cell cycle;

(8) it modulates mitogenesis;

(9) it modulates cell motility;

(10) it modulates a cell-to-cell interaction;

(11) it modulates cell metabolism;

(12) it modulates gene transcription;

(13) it modulates an immune response;

(14) it modulates a cellular response to an adrenocortical hormone;

(15) it modulates skeletal muscle development;

(16) it modulates development or progression of muscular dystrophy;

(17) it modulates spermatogenesis;

(18) it modulates fertility;

(19) it modulates tumorigenesis;

(20) it modulates tumor growth;

(21) it modulates tumor metastasis;

(22) it modulates a testosterone-associated disorder;

(23) it modulates tissue growth in an embryo or fetus;

(24) it modulates tissue differentiation in an embryo or fetus;

(25) it modulates organogenesis in an embryo or fetus;

(26) it modulates wound healing;

(27) it modulates neuronal growth;

(28) it modulates neuronal interconnection;

(29) it has a molecular weight, amino acid composition or other physical characteristic of a 15418 protein of SEQ ID NO: 42;

(30) it has an overall sequence similarity (identity) of at least 60–65%, preferably at least 70%, more preferably at least 75, 80, 85, 86, 87, 88, 89, 90, 91, 92, 93, 94, 95, 96, 97, 98, or 99% or more, with a portion of SEQ ID NO: 42; or

(31) it has a DSPc domain which is preferably about 70%, 80%, 90%, 95%, 96%, 97%, 98%, 99% or higher, identical with amino acid residues 53–303 of SEQ ID NO: 42.

In a preferred embodiment, the 69087, 15821, or 15418 protein or fragment thereof differs only insubstantially, if at all, from the corresponding sequence in SEQ ID NOs: 2, 22, and 42. In one embodiment, it differs by at least one, but by fewer than 15, 10 or 5 amino acid residues. In another, it differs from the corresponding sequence in SEQ ID NOs: 2, 22, and 42 by at least one residue but fewer than 20%, 15%, 10% or 5% of the residues differ from the corresponding sequence in SEQ ID NOs: 2, 22, and 42 (if this comparison requires alignment the sequences should be aligned for maximum homology. "Looped" out sequences from deletions or insertions, or mismatches, are considered differences). The differences are, preferably, differences or changes at a non-essential amino acid residues or involve a conservative substitution of one residue for another. In a preferred embodiment the differences are not in residues 191–454 (and are especially not in residues 312–324) of SEQ ID NO: 2, in residues 483 to 528 of SEQ ID NO: 22, or in residues 53 to 303 of SEQ ID NO: 42.

Other embodiments include a protein that has one or more changes in amino acid sequence, relative to one of SEQ ID NOs: 2, 22, and 42 (e.g., a change in an amino acid residue which is not essential for activity). Such 69087, 15821, and 15418 proteins differ in amino acid sequence from the corresponding one of SEQ ID NOs: 2, 22, and 42, yet retain biological activity.

In one embodiment, the protein includes an amino acid sequence at least about 60%, 65%, 70%, 75%, 80%, 85%, 90%, 95%, 98% or more homologous to one of SEQ ID NOs: 2, 22, and 42.

A 69087 protein or fragment is provided which has an amino acid sequence which varies from SEQ ID NO: 2 in one or both of the regions corresponding to residues 1–190 and 455–553 of SEQ ID NO: 2 by at least one, but by fewer than 15, 10 or 5 amino acid residues, but which does not differ from SEQ ID NO: 2 in the region corresponding to residues 191–454 of SEQ ID NO: 2 (if this comparison requires alignment the sequences should be aligned for maximum homology). Also provided is a 15821 protein or fragment which has an amino acid sequence which varies from SEQ ID NO: 22 in one or both of the regions corresponding to residues 1–482 and 529–564 of SEQ ID NO: 22 by at least one, but by fewer than 15, 10 or 5 amino acid residues, but which does not differ from SEQ ID NO: 22 in the region corresponding to residues 483–528 of SEQ ID NO: 22 (if this comparison requires alignment the sequences should be aligned for maximum homology). Also provided is a 15418 protein or fragment which has an amino acid sequence which varies from SEQ ID NO: 42 in one or both of the regions corresponding to residues 1–20 and 160–190 of SEQ ID NO: 42 by at least one, but by fewer than 15, 10 or 5 amino acid residues, but which does not differ from SEQ ID NO: 42 in the region corresponding to residues 21–159 of SEQ ID NO: 42 (if this comparison requires alignment the sequences should be aligned for maximum homology). "Looped" out sequences from deletions or insertions, or mismatches, are considered differences). In some embodiments the difference is at a non-essential residue or is a conservative substitution, while in others the difference is at an essential residue or is a non-conservative substitution.

A biologically active portion of a 69087 protein should include at least the 69087 pkinase domain. A biologically active portion of a 15821 protein should include at least the 15821 RING finger domain. A biologically active portion of a 15418 protein should include at least the 15418 DSPc domain. Moreover, other biologically active portions, in which other regions of the protein are deleted, can be prepared by recombinant techniques and evaluated for one or more of the functional activities of a native 69087, 15821, or 15418 protein.

In a preferred embodiment, the 69087 protein has the amino acid sequence SEQ ID NO: 2. In other embodiments, the 69087 protein is substantially identical to SEQ ID NO: 2. In yet another embodiment, the 69087 protein is substantially identical to SEQ ID NO: 2 and retains the functional activity of the protein of SEQ ID NO: 2.

In a preferred embodiment, the 15821 protein has the amino acid sequence SEQ ID NO: 22. In other embodiments, the 15821 protein is substantially identical to SEQ ID NO: 22. In yet another embodiment, the 15821 protein is substantially identical to SEQ ID NO: 22 and retains the functional activity of the protein of SEQ ID NO: 22.

In a preferred embodiment, the 15418 protein has the amino acid sequence SEQ ID NO: 42. In other embodiments, the 15418 protein is substantially identical to SEQ ID NO: 42. In yet another embodiment, the 15418 protein is substantially identical to SEQ ID NO: 42 and retains the functional activity of the protein of SEQ ID NO: 42.

Chimeric or Fusion Proteins

In another aspect, the invention provides 69087, 15821, and 15418 chimeric or fusion proteins. As used herein, a 69087, 15821, or 15418 "chimeric protein" or "fusion protein" includes a 69087, 15821, or 15418 polypeptide linked to a non-69087, non- 15821, or non-15418 polypeptide. A "non-69087 polypeptide" refers to a polypeptide having an amino acid sequence corresponding to a protein which is not substantially homologous to the 69087 protein, e.g., a protein which is different from the 69087 protein and which is derived from the same or a different organism. The 69087, 15821, or 15418 polypeptide of the fusion protein can correspond to all or a portion e.g., a fragment described herein of the corresponding amino acid sequence. In a preferred embodiment, a 69087, 15821, or 15418 fusion protein includes at least one or more biologically active portions of the corresponding protein. The non-69087, non-15821, or non-15418 polypeptide can be fused to the amino or carboxyl terminus of the corresponding 69087, 15821, or 15418 polypeptide.

The fusion protein can include a moiety that has a high affinity for a ligand. For example, the fusion protein can be a GST-69087 fusion protein in which the 69087 sequences are fused to the carboxyl terminus of the GST sequences. Such fusion proteins can facilitate the purification of recombinant 69087, 15821, or 15418. Alternatively, the fusion protein can be a 69087, 15821, or 15418 protein containing a heterologous signal sequence at its amino terminus. In certain host cells (e.g., mammalian host cells), expression and/or secretion of 69087, 15821, or 15418 can be increased through use of a heterologous signal sequence.

Fusion proteins can include all or a part of a serum protein, e.g., an IgG constant region, or human serum albumin.

The 69087, 15821, or 15418 fusion proteins of the invention can be incorporated into pharmaceutical compositions and administered to a subject in vivo. The fusion proteins can be used to affect the bioavailability of a 69087, 15821, or 15418 substrate. 69087, 15821, or 15418 fusion proteins can be useful therapeutically for the treatment of disorders caused by, for example, (i) aberrant modification or mutation of a gene encoding a 69087, 15821, or 15418 protein; (ii) mis-regulation of the 69087, 15821, or 15418 gene; and (iii) aberrant post-translational modification of a 69087, 15821, or 15418 protein.

Moreover, the 69087, 15821, or 15418 fusion proteins of the invention can be used as immunogens to produce anti-69087, anti-15821, or anti-15418 antibodies in a subject, to purify 69087, 15821, or 15418 ligands and in screening assays to identify molecules that inhibit the interaction of 69087, 15821, or 15418 with a substrate.

Expression vectors are commercially available that already encode a fusion moiety (e.g., a GST polypeptide). A 69087-, 15821-, or 15418-encoding nucleic acid can be cloned into such an expression vector such that the fusion moiety is linked in-frame to the 69087, 15821, or 15418 protein.

Variants of 69087, 15821, and 15418 Proteins

In another aspect, the invention also features a variant of a 69087, 15821, or 15418 polypeptide, e.g., which functions as an agonist (mimetics) or as an antagonist. Variants of the 69087, 15821, or 15418 proteins can be generated by mutagenesis, e.g., discrete point mutation, the insertion or deletion of sequences or the truncation of a 69087, 15821, or 15418 protein. An agonist of the 69087, 15821, or 15418 proteins can retain substantially the same, or a subset, of the biological activities of the naturally occurring form of the corresponding protein. An antagonist of a 69087, 15821, or 15418 protein can inhibit one or more of the activities of the naturally occurring form of the corresponding protein by, for example, competitively modulating an activity of the corresponding protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the corresponding 69087, 15821, or 15418 protein.

Variants of a 69087, 15821, or 15418 protein can be identified by screening combinatorial libraries of mutants, e.g., truncation mutants, of a 69087, 15821, or 15418 protein for agonist or antagonist activity.

Libraries of fragments e.g., amino-terminal, carboxyl-terminal, or internal fragments, of a 69087, 15821, or 15418 protein coding sequence can be used to generate a variegated population of fragments for screening and subsequent selection of variants of a 69087, 15821, or 15418 protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a technique which enhances the frequency of functional mutants in the libraries, can be used in combination with the screening assays to identify 69087, 15821, or 15418 variants (Arkin et al., 1992, Proc. Natl. Acad. Sci. USA 89:7811–7815; Delgrave et al., 1993, Protein Engr. 6:327–331).

Cell based assays can be exploited to analyze a variegated 69087, 15821, or 15418 library. For example, a library of expression vectors can be transfected into a cell line, e.g., a cell line, which ordinarily responds to 69087 in a substrate-dependent manner. The transfected cells are then contacted with 69087 and the effect of the expression of the mutant on signaling by the 69087 substrate can be detected, e.g., by measuring changes in cell growth and/or enzymatic activity. Plasmid DNA can then be recovered from the cells that score for inhibition, or alternatively, potentiation of signaling by the 69087 substrate, and the individual clones further characterized.

In another aspect, the invention features a method of making a 69087, 15821, or 15418 polypeptide, e.g., a peptide having a non-wild-type activity, e.g., an antagonist, agonist, or super agonist of a naturally-occurring 69087, 15821, or 15418 polypeptide, e.g., a naturally-occurring 69087, 15821, or 15418 polypeptide. The method includes: altering the sequence of a 69087, 15821, or 15418 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 69087, 15821, or 15418 polypeptide a biological activity of a naturally occurring 69087, 15821, or 15418 polypeptide. The method includes: altering the sequence, e.g., by substitution or deletion of one or more residues, of a 69087, 15821, or 15418 polypeptide, e.g., altering the sequence of a non-conserved region, or a domain or residue described herein, and testing the altered polypeptide for the desired activity.

Anti-69087, Anti-15821, and Anti-15418 Antibodies

In another aspect, the invention provides anti-69087 antibodies, anti-15821 antibodies, and anti-15418 antibodies. The term "antibody" as used herein refers to an immunoglobulin molecule or immunologically active portion thereof, i.e., an antigen-binding portion. Examples of immunologically active portions of immunoglobulin molecules include F(ab) and $F(ab')_2$ fragments which can be generated by treating the antibody with an enzyme such as pepsin.

The antibody can be a polyclonal, monoclonal, recombinant, e.g., a chimeric or humanized, fully-human, non-human, e.g., murine, or single chain antibody. In a preferred embodiment, it has effector function and can fix complement. The antibody can be coupled to a toxin or imaging agent.

A full-length 69087, 15821, or 15418 protein or an antigenic peptide fragment of one of these proteins can be used as an immunogen or can be used to identify anti-69087, anti-15821, or anti-15418 antibodies made with other immunogens, e.g., cells, membrane preparations, and the like. The antigenic peptide of 69087, 15821, or 15418 should include at least 8 amino acid residues of the amino acid sequence shown in one of SEQ ID NOs: 2, 22, and 42 and encompasses an epitope of 69087, 15821, or 15418. Preferably, the antigenic peptide includes at least 10 amino acid residues, more preferably at least 15 amino acid residues, even more preferably at least 20 amino acid residues, and most preferably at least 30 amino acid residues.

Fragments of 69087 which include about residues 234–250 of SEQ ID NO: 2 can be used to make antibodies, e.g., for use as immunogens or to characterize the specificity of an antibody, against hydrophobic regions of the 69087 protein. Similarly, a fragment of 69087 which include about residues 40–55 or 445–470 of SEQ ID NO: 2 can be used to make an antibody against a hydrophilic region of the 69087 protein. Fragments of 15821 which include about residues 395–405 of SEQ ID NO: 22 can be used to make antibodies, e.g., for use as immunogens or to characterize the specificity of an antibody, against hydrophobic regions of the 15821 protein. Similarly, a fragment of 15821 which include about residues 160–180 or 220–240 of SEQ ID NO: 22 can be used to make an antibody against a hydrophilic region of the 15821 protein. Fragments of 15418 which include about residues 45–60 of SEQ ID NO: 42 can be used to make antibodies, e.g., for use as immunogens or to characterize the specificity of an antibody, against hydrophobic regions of the 15418 protein. Similarly, a fragment of 15418 which include about residues 130–155 of SEQ ID NO: 42 can be used to make an antibody against a hydrophilic region of the 15418 protein.

Antibodies reactive with, or specific for, any of these regions, or other regions or domains described herein are provided.

Preferred epitopes encompassed by the antigenic peptide are regions of 69087, 15821, or 15418 are located on the surface of the protein, e.g., hydrophilic regions, as well as regions with high antigenicity. For example, an Emini surface probability analysis of the human 69087, 15821, or 15418 protein sequence can be used to indicate the regions that have a particularly high probability of being localized to the surface of the corresponding protein and are thus likely to constitute surface residues useful for targeting antibody production.

Chimeric, humanized, but most preferably, completely human antibodies are desirable for applications which include repeated administration, e.g., therapeutic treatment (and some diagnostic applications) of human patients.

The anti-69087, anti-15821, or anti-15418 antibody can be a single chain antibody. A single-chain antibody (scFV) can be engineered (e.g., Colcher et al., 1999, Ann. N.Y. Acad. Sci. 880:263–280; Reiter, 1996, Clin. Cancer Res. 2:245–252). The single chain antibody can be dimerized or multimerized to generate multivalent antibodies having specificities for different epitopes of the same target protein.

In a preferred embodiment, the antibody has reduced or no ability to bind an Fc receptor. For example, it can be an isotype, subtype, fragment or other mutant, which does not support binding to an Fc receptor, e.g., it can have a mutated or deleted Fc receptor binding region.

An anti-69087, anti-15821, or anti-15418 antibody (e.g., monoclonal antibody) can be used to isolate the corresponding protein by standard techniques, such as affinity chromatography or immunoprecipitation. Moreover, an anti-69087, anti-15821, or anti-15418 antibody can be used to detect the corresponding protein (e.g., in a cellular lysate or cell supernatant) in order to evaluate the abundance and pattern of expression of the protein. Anti-69087, anti-15821, or anti-15418 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 69087, 15821, or 15418 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 69087, 15821, or 15418 proteins, mutant forms of 69087, 15821, or 15418 proteins, fusion proteins, and the like).

The recombinant expression vectors of the invention can be designed for expression of 69087, 15821, or 15418 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel (1990, Gene Expression Technology: Methods in Enzymology 185, Academic Press, San Diego). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith et al., 1988, Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 69087, 15821, or 15418 activity assays, (e.g., direct assays or competitive assays described in detail below), or to generate antibodies specific for 69087, 15821, or 15418 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six weeks).

To maximize recombinant protein expression in *E. coli*, the protein is expressed in a host bacterial strain with an impaired capacity to proteolytically cleave the recombinant protein (Gottesman, 1990, Gene Expression Technology: Methods in Enzymology 185, Academic Press, San Diego, 119–128). Another strategy is to alter the nucleic acid sequence of the nucleic acid to be inserted into an expression vector so that the individual codons for each amino acid are those preferentially utilized in *E. coli* (Wada et al., 1992, Nucl. Acids Res. 20:2111–2118). Such alteration of nucleic acid sequences of the invention can be carried out by standard DNA synthesis techniques.

The expression vector can be a yeast expression vector, a vector for expression in insect cells, e.g., a baculovirus expression vector, or a vector suitable for expression in mammalian cells.

When used in mammalian cells, the expression vector's control functions are often provided by viral regulatory elements. For example, commonly used viral promoters are derived from polyoma, adenovirus 2, cytomegalovirus and simian virus 40 (SV40).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., 1987, Genes Dev. 1:268–277), lymphoid-specific promoters (Calame et al., 1988, Adv. Immunol. 43:235–275), in particular promoters of T cell receptors (Winoto et al., 1989, EMBO J. 8:729–733) and immunoglobulins (Banerji et al., 1983, Cell 33:729–740; Queen et al., 1983, Cell 33:741–748), neuron-specific promoters (e.g., the neurofilament promoter; Byrne et al., 1989, Proc. Natl. Acad. Sci. USA 86:5473–5477), pancreas-specific promoters (Edlund et al., 1985, Science 230:912–916), and mammary gland-specific promoters (e.g., milk whey promoter; U.S. Pat. No. 4,873,316 and European Patent Application publication number 264,166).

Developmentally-regulated promoters are also encompassed, for example, the murine hox promoters (Kessel et al., 1990, Science 249:374–379) and the alpha-fetoprotein promoter (Campes et al., 1989, Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes, see Weintraub, H. et al. (1986, Trends Genet. 1:Review).

Another aspect the invention provides a host cell which includes a nucleic acid molecule described herein, e.g., a 69087, 15821, or 15418 nucleic acid molecule within a recombinant expression vector or a 69087, 15821, or 15418 nucleic acid molecule containing sequences which allow it to homologously recombine into a specific site of the host cell's genome. The terms "host cell" and "recombinant host cell" are used interchangeably herein. Such terms refer not only to the particular subject cell, but also to the progeny or potential progeny of such a cell. Because certain modifications can occur in succeeding generations due to either mutation or environmental influences, such progeny may not, in fact, be identical to the parent cell, but are included within the scope of the term as used herein.

A host cell can be any prokaryotic or eukaryotic cell. For example, a 69087, 15821, or 15418 protein can be expressed in bacterial cells such as *E. coli,* insect cells, yeast or mammalian cells (such as Chinese hamster ovary (CHO) cells) or COS cells. Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 69087, 15821, or 15418 protein. Accordingly, the invention further provides methods for producing a 69087, 15821, or 15418 protein using the host cells of the invention. In one embodiment, the method includes culturing the host cell of the invention (into which a recombinant expression vector encoding the corresponding protein has been introduced) in a suitable medium such that the protein is produced. In another embodiment, the method further includes isolating a 69087, 15821, or 15418 protein from the medium or the host cell.

In another aspect, the invention features, a cell or purified preparation of cells which include a 69087, 15821, or 15418 transgene, or which otherwise mal-express 69087, 15821, or 15418. The cell preparation can consist of human or non-human cells, e.g., rodent cells, e.g., mouse or rat cells, rabbit cells, or pig cells. In preferred embodiments, the cell or cells include a 69087, 15821, or 15418 transgene, e.g., a heterologous form of 69087, 15821, or 15418, e.g., a gene derived from humans (in the case of a non-human cell). The transgene can be mal-expressed, e.g., over-expressed or under-expressed. In other preferred embodiments, the cell or cells include a gene that mal-expresses an endogenous 69087, 15821, or 15418, e.g., a gene the expression of which is disrupted, e.g., a knockout. Such cells can serve as a model for studying disorders that are related to mutated or mal-expressed 69087, 15821, or 15418 alleles or for use in drug screening.

In another aspect, the invention includes, a human cell, e.g., a hematopoietic stem cell, transformed with nucleic acid that encodes a 69087, 15821, or 15418 polypeptide.

Also provided are cells, preferably human cells, e.g., human hematopoietic or fibroblast cells, in which an endogenous 69087, 15821, or 15418 is under the control of a regulatory sequence that does not normally control expression of the endogenous 69087, 15821, or 15418 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 69087, 15821, or 15418 gene. For example, an endogenous 69087 gene that is "transcriptionally silent," e.g., not normally expressed, or expressed only at very low levels, can be activated by inserting a regulatory element that is capable of promoting the expression of a normally expressed gene product in that cell. Techniques such as targeted homologous recombination, can be used to insert the heterologous DNA as described (e.g., U.S. Pat. No. 5,272,071; PCT publication number WO 91/06667).

Transgenic Animals

The invention provides non-human transgenic animals. Such animals are useful for studying the function and/or activity of a 69087, 15821, or 15418 protein and for identifying and/or evaluating modulators of 69087, 15821, or 15418 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 69087, 15821, or 15418 gene has been altered, e.g., by homologous recombination between the endogenous gene and an exogenous DNA molecule introduced into a cell of the animal (e.g., an embryonic cell of the animal, prior to development of the animal).

Intronic sequences and polyadenylation signals can also be included in the transgene to increase the efficiency of expression of the transgene. A tissue-specific regulatory sequence(s) can be operably linked to a transgene of the invention to direct expression of a 69087, 15821, or 15418 protein to particular cells. A transgenic founder animal can be identified based upon the presence of a 69087, 15821, or 15418 transgene in its genome and/or expression of the corresponding mRNA in tissues or cells of the animals. A transgenic founder animal can then be used to breed additional animals carrying the transgene. Moreover, transgenic animals carrying a transgene encoding a 69087, 15821, or 15418 protein can further be bred to other transgenic animals carrying other transgenes.

69087, 15821, or 15418 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk- or egg-specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 69087, 15821, or 15418 protein (e.g., via a recombinant expression vector in a host cell in gene therapy applications), to detect a 69087, 15821, or 15418 mRNA (e.g., in a biological sample), to detect a genetic alteration in a 69087, 15821, or 15418 gene and to modulate 69087, 15821, or 15418 activity, as described further below. The 69087, 15821, or 15418 proteins can be used to treat disorders characterized by insufficient or excessive production of the corresponding protein's substrate or production of inhibitors of the corresponding protein. In addition, the 69087, 15821, or 15418 proteins can be used to screen for naturally occurring substrates of the individual proteins, to screen for drugs or compounds which modulate 69087, 15821, or 15418 activity, as well as to treat disorders characterized by insufficient or excessive production of 69087, 15821, or 15418 protein or production of 69087, 15821, or 15418 protein forms which have decreased, aberrant or unwanted activity compared to the corresponding wild-type proteins.

Exemplary disorders include, for 69087, those in which protein phosphorylation is aberrant (e.g., cancer, viral infection, auto-immune diseases such as arthritis or muscular dystrophy, neural and sensory disorders such as olfactory and vision disorders, cardiac disorders, and developmental disorders). Moreover, the anti-69087 antibodies of the invention can be used to detect and isolate 69087 proteins, regulate the bioavailability of 69087 proteins, and modulate 69087 activity.

A method of evaluating a compound for the ability to interact with, e.g., bind to, a 69087, 15821, or 15418 polypeptide is provided. The method includes: contacting the compound with the 69087, 15821, or 15418 polypeptide; and evaluating the ability of the compound to interact with, e.g., to bind or form a complex with, the polypeptide. This method can be performed in vitro, e.g., in a cell free system, or in vivo, e.g., in a two-hybrid interaction trap assay. This method can be used to identify naturally-occurring molecules that interact with a 69087, 15821, or 15418 polypeptide. It can also be used to find natural or synthetic inhibitors of a 69087, 15821, or 15418 polypeptide. Screening methods are discussed in more detail below.

Screening Assays

The invention provides screening methods (also referred to herein as "assays") for identifying modulators, i.e., candidate or test compounds or agents (e.g., proteins, peptides, peptidomimetics, peptoids, small molecules or other drugs) which bind with 69087, 15821, or 15418 proteins, have a stimulatory or inhibitory effect on, for example, expression or activity of the corresponding protein, or have a stimulatory or inhibitory effect on, for example, the expression or activity of a substrate of the protein. Compounds thus identified can be used to modulate the activity of target gene products (e.g., 69087, 15821, or 15418 genes) in a therapeutic protocol, to elaborate the biological function of the target gene product, or to identify compounds that disrupt normal target gene interactions.

In one embodiment, the invention provides assays for screening candidate or test compounds that are substrates of a 69087, 15821, or 15418 protein or polypeptide or a biologically active portion of one of these. In another embodiment, the invention provides assays for screening candidate or test compounds that bind to or modulate the activity of a 69087, 15821, or 15418 protein or polypeptide or a biologically active portion of one of these.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; e.g., Zuckermann et al., 1994, J. Med. Chem. 37:2678–2685); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries have been described (e.g., DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233).

Libraries of compounds can be presented in solution (e.g., Houghten, 1992, Biotechniques 13:412–421), or on beads (Lam, 1991, Nature 354:82–84), chips (Fodor, 1993, Nature 364:555–556), bacteria (U.S. Pat. No. 5,223,409), spores (U.S. Pat. No. 5,223,409), plasmids (Cull et al., 1992, Proc. Natl. Acad. Sci. USA 89:1865–1869), or on phage (Scott et al., 1990, Science 249:386–390; Devlin, 1990, Science 249:404–406; Cwirla et al., 1990, Proc. Natl. Acad. Sci. USA 87:6378–6382; Felici, 1991, J. Mol. Biol. 222:301–310; U.S. Pat. No. 5,223,409).

In one embodiment, an assay is a cell-based assay in which a cell which expresses a 69087, 15821, or 15418 protein or a biologically active portion of one of these is contacted with a test compound, and the ability of the test compound to modulate activity of the corresponding protein is determined. Determining the ability of the test compound to modulate activity can be accomplished by monitoring, for example, changes in enzymatic activity. The cell, for example, can be of mammalian origin.

The ability of the test compound to modulate 69087, 15821, or 15418 binding to a compound, e.g., a substrate, or to bind to 69087, 15821, or 15418 can also be evaluated. This can be accomplished, for example, by coupling the compound, e.g., the substrate, with a radioisotope or enzymatic label such that binding of the compound, e.g., the substrate, to the protein can be determined by detecting the labeled compound, e.g., substrate, in a complex. Alternatively, 69087, 15821, or 15418 could be coupled with a radioisotope or enzymatic label to monitor the ability of a test compound to modulate binding of the protein to a corresponding substrate in a complex. For example, compounds (e.g., 69087, 15821, or 15418 substrates) can be labeled with $^{125}I$, $^{35}S$, $^{14}C$, or $^{3}H$, either directly or indirectly, and the radioisotope detected by direct counting of radio-emission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a substrate) to interact with 69087, 15821, or 15418 with or without the labeling of any of the interactants can be evaluated. For example, a microphysiometer can be used to detect the interaction of a compound with the protein without the labeling of either the compound or the protein (McConnell et al., 1992, Science 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 69087, 15821, or 15418.

In yet another embodiment, a cell-free assay is provided in which a 69087, 15821, or 15418 protein or biologically active portion of one of these is contacted with a test compound and the ability of the test compound to bind to the protein or biologically active portion is evaluated. Preferred biologically active portions of the 69087, 15821, or 15418 proteins to be used in assays of the present invention include fragments that participate in interactions with non-69087, non-15821, or non-15418 molecules, e.g., fragments with high surface probability scores.

Soluble and/or membrane-bound forms of isolated proteins (e.g., 69087, 15821, or 15418 proteins or biologically active portions of one of these) can be used in the cell-free assays of the invention. When membrane-bound forms of the protein are used, it can be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-{(3-cholamidopropyl) dimethylamminio}-1-propane sulfonate (CHAPS), 3-{(3-cholamidopropyl) dimethylamminio}-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET; e.g., U.S. Pat. Nos. 5,631,169; 4,868,103). A fluorophore label is selected such that a first donor molecule's emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 69087, 15821, or 15418 protein to bind to a target molecule can be accomplished using real-time biomolecular interaction analysis (BIA; e.g., Sjolander et al., 1991, Anal. Chem. 63:2338–2345; Szabo et al., 1995, Curr. Opin. Struct. Biol. 5:699–705). "Surface plasmon resonance" (SPR) or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of SPR), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It can be desirable to immobilize one of 69087, 15821, or 15418, an anti-69087 antibody, an anti-15821 antibody, an anti-15418 antibody, or a target molecule of one of 69087, 15821, and 15418 to facilitate separation of complexed from non-complexed forms of one or both of the proteins, as well as to accommodate automation of the assay. Binding of a test compound to a 69087, 15821, or 15418 protein, or interaction of a 69087, 15821, or 15418 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/69087, /15821, or /15418 fusion proteins or glutathione-S-transferase/target fusion proteins can be adsorbed onto glutathione Sepharose™ beads (Sigma Chemical, St. Louis, Mo.) or glutathione-derivatized microtiter plates, which are then combined with the test compound or the test compound and either the non-adsorbed target protein or one of 69087, 15821, or 15418 proteins, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 69087, 15821, or 15418 binding or activity can be determined using standard techniques.

Other techniques for immobilizing either a 69087, 15821, or 15418 protein or a target molecule of one of these proteins on matrices include using conjugation of biotin and streptavidin. Biotinylated 69087, 15821, or 15418 protein or target molecules can be prepared from biotin-N-hydroxy-succinimide using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, non-reacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 69087, 15821, or 15418 protein or with a target molecule of one of these proteins but which do not interfere with binding of the 69087, 15821, or 15418 protein to its corresponding target molecule. Such antibodies can be derivatized to the wells of the plate, and unbound target or protein trapped in the wells by antibody conjugation. Methods for detecting such complexes, in addition to those described above for the GST-immobilized complexes, include immunodetection of complexes using antibodies reactive with the protein or target molecule, as well as enzyme-linked assays which rely on detecting an enzymatic activity associated with the protein or target molecule.

Alternatively, cell free assays can be conducted in a liquid phase. In such an assay, the reaction products are separated from non-reacted components, by any of a number of standard techniques, including, but not limited to: differential centrifugation (e.g., Rivas et al., 1993, Trends Biochem. Sci. 18:284–287); chromatography (e.g., gel filtration chromatography or ion-exchange chromatography); electrophoresis (e.g., Ausubel et al., eds., 1999, Current Protocols in Molecular Biology, J. Wiley, New York); and immunoprecipitation (e.g., Ausubel, supra). Such resins and chromatographic techniques are known to one skilled in the art (e.g., Heegaard, 1998, J. Mol. Recognit. 11: 141–148; Hage et al., 1997, J. Chromatogr. B Biomed. Sci. Appl. 699:499–525). Further, fluorescence energy transfer can also be conveniently utilized, as described herein, to detect binding without further purification of the complex from solution.

In a preferred embodiment, the assay includes contacting a 69087, 15821, or 15418 protein or a biologically active portion of one of these with a known compound which binds the protein to form an assay mixture, contacting the assay mixture with a test compound, and determining the ability of the test compound to interact with the corresponding protein, wherein determining the ability of the test compound to interact with a 69087, 15821, or 15418 protein includes determining the ability of the test compound to preferentially bind to 69087, 15821, or 15418 or to the biologically active portion thereof, or to modulate the activity of a target molecule, as compared to the known compound.

The target gene products of the invention can, in vivo, interact with one or more cellular or extracellular macromolecules, such as proteins (e.g., individual GPCRs and arrestins). For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 69087, 15821, and 15418 genes herein identified. In an alternative embodiment, the invention provides methods for determining the ability of the test compound to modulate the activity of a 69087, 15821, or 15418 protein through modulation of the activity of a downstream effector of a 69087, 15821, or 15418 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt pre-formed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, non-reacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from non-reacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 69087, 15821, and 15418 proteins can be used as "bait proteins" in a two-hybrid assay or three-hybrid assay (e.g., U.S. Pat. No. 5,283,317; Zervos et al., 1993, Cell 72:223–232; Madura et al., 1993, J. Biol. Chem. 268:12046–12054; Bartel et al., 1993, Biotechniques 14:920–924; Iwabuchi et al., 1993, Oncogene 8:1693–1696; PCT publication number WO 94/10300), to identify other proteins, which bind to or interact with 69087, 15821, or 15418 and are involved in 69087, 15821, or 15418 activity. Such binding proteins can be activators or inhibitors of signals by the corresponding protein or a target of the corresponding protein as, for example, downstream elements of a 69087-, 15821-, or 15418-mediated signaling pathway.

The two-hybrid system is based on the modular nature of most transcription factors, which consist of separable DNA-binding and activation domains. Briefly, the assay utilizes two different DNA constructs. In one construct, the gene that codes for a 69087, 15821, or 15418 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively, the protein can be fused to the activator domain). If the "bait" and the "prey" proteins are able to interact in vivo forming a 69087-, 15821-, or 15418-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 69087, 15821, or 15418 protein.

In another embodiment, modulators of 69087, 15821, or 15418 expression are identified. For example, a cell or cell free mixture is contacted with a candidate compound and the expression of 69087, 15821, or 15418 mRNA or protein evaluated relative to the level of expression of the same mRNA or protein in the absence of the candidate compound. When expression of the mRNA or protein is greater in the presence of the candidate compound than in its absence, the candidate compound is identified as a stimulator of mRNA or protein expression. Alternatively, when expression of the mRNA or protein is less (i.e., statistically significantly less) in the presence of the candidate compound than in its absence, the candidate compound is identified as an inhibitor of mRNA or protein expression. The level of 69087, 15821, or 15418 mRNA or protein expression can be determined by methods described herein for detecting the corresponding mRNA or protein.

In another aspect, the invention pertains to a combination of two or more of the assays described herein. For example, a modulating agent can be identified using a cell-based or a cell free assay, and the ability of the agent to modulate the activity of a 69087, 15821, or 15418 protein can be confirmed in vivo, e.g., in an animal such as an animal model for a disease.

This invention further pertains to novel agents identified by the above-described screening assays. Accordingly, it is within the scope of this invention to further use an agent identified as described herein (e.g., a 69087, 15821, or 15418 modulating agent, an antisense 69087, 15821, or 15418 nucleic acid molecule, a 69087-, 15821-, or 15418-specific antibody, or a 69087-, 15821-, or 15418-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome, e.g., to locate gene regions associated with genetic disease or to associate 69087, 15821, or 15418 with a disease; (ii) identify an individual from a minute biological sample (tissue typing); and (iii) aid in forensic identification of a biological sample. These applications are described in the subsections below.

Chromosome Mapping

The 69087, 15821, or 15418 nucleotide sequences or portions thereof can be used to map the location of the corresponding gene on a chromosome. This process is called chromosome mapping. Chromosome mapping is useful in correlating the 69087, 15821, or 15418 sequences with genes associated with disease.

Briefly, 69087, 15821, or 15418 genes can be mapped to chromosomes by preparing PCR primers preferably 15–25 base pairs in length) from the corresponding nucleotide sequence (e.g., one of SEQ ID NOs: 1, 3, 21, 23, 41, and 43). These primers can then be used for PCR screening of somatic cell hybrids containing individual human chromosomes. Only those hybrids containing the human gene corresponding to the 69087, 15821, or 15418 sequence will yield an amplified fragment.

A panel of somatic cell hybrids in which each cell line contains either a single human chromosome or a small number of human chromosomes, and a full set of mouse chromosomes, can allow easy mapping of individual genes to specific human chromosomes (D'Eustachio et al., 1983, Science 220:919–924).

Other mapping strategies e.g., in situ hybridization as described (Fan et al., 1990, Proc. Natl. Acad. Sci. USA 87:6223–6227), pre-screening with labeled flow-sorted chromosomes, and pre-selection by hybridization to chromosome specific cDNA libraries can be used to map 69087, 15821, or 15418 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of FISH, see Verma et al. (1988, Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to non-coding regions of the genes are typically preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), as described (e.g., Egeland et al., 1987, Nature, 325:783–787).

Moreover, differences in the DNA sequences between individuals affected and unaffected with a disease associated with the 69087, 15821, or 15418 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 69087, 15821, and 15418 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 69087, 15821, and 15418 nucleotide sequences described herein can be used to prepare PCR primers homologous to the 5'- and 3'-ends of the sequence. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the non-coding regions. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of SEQ ID NO: 1 can provide positive individual identification with a panel of perhaps 10 to 1,000 primers which each yield a non-coding amplified sequence of 100 bases. If predicted coding sequences are used, such as those in SEQ ID NOs: 3, 23, and 43, a more appropriate number of primers for positive individual identification would be 500–2,000.

If a panel of reagents from 69087, 15821, or 15418 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual nucleotide sequence information can be used for identification as an accurate alternative to patterns formed by restriction enzyme generated fragments. Sequences targeted to non-coding regions of SEQ ID NOs: 1, 21, and 41 (e.g., fragments having a length of at least 20 nucleotide residues, preferably at least 30 nucleotide residues) are particularly appropriate for this use.

The 69087, 15821, and 15418 nucleotide sequences described herein can further be used to provide polynucleotide reagents, e.g., labeled or label-able probes which can be used in, for example, an in situ hybridization technique, to identify a specific tissue, e.g., a tissue containing hematopoietic cells. This can be very useful in cases where a forensic pathologist is presented with a tissue of unknown origin. Panels of such 69087, 15821, or 15418 probes can be used to identify tissue by species and/or by organ type.

In a similar fashion, these reagents, e.g., 69087, 15821, or 15418 primers or probes can be used to screen tissue culture for contamination (i.e., to screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides a method of determining if a subject is at risk for a disorder related to a lesion in, or the malexpression of, a gene that encodes a 69087, 15821, or 15418 polypeptide.

Such disorders include, e.g., a disorder associated with the malexpression of a 69087, 15821, or 15418 polypeptide, e.g., an immune disorder or a neoplastic disorder.

The method includes one or more of the following:

(i) detecting, in a tissue of the subject, the presence or absence of a mutation which affects the expression of the 69087, 15821, or 15418 gene, or detecting the presence or absence of a mutation in a region which controls the expression of the gene, e.g., a mutation in the 5'-control region;

(ii) detecting, in a tissue of the subject, the presence or absence of a mutation which alters the structure of the 69087, 15821, or 15418 gene;

(iii) detecting, in a tissue of the subject, the malexpression of the 69087, 15821, or 15418 gene at the mRNA level, e.g., detecting a non-wild-type level of a mRNA; and (iv) detecting, in a tissue of the subject, the malexpression of the gene at the protein level, e.g., detecting a non-wild-type level of a 69087, 15821, or 15418 polypeptide.

In preferred embodiments the method includes: ascertaining the existence of at least one of: a deletion of one or more nucleotides from the 69087, 15821, or 15418 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from one of SEQ ID NOs: 1, 21, and 41 or naturally occurring mutants thereof, or 5'- or 3'-flanking sequences naturally associated with the 69087, 15821, or 15418 gene; (ii) exposing the probe/primer to nucleic acid of the tissue; and detecting the presence or absence of the genetic lesion by hybridization of the probe/primer to the nucleic acid, e.g., by in situ hybridization.

In preferred embodiments, detecting the malexpression includes ascertaining the existence of at least one of: an alteration in the level of a messenger RNA transcript of the 69087, 15821, or 15418 gene; the presence of a non-wild-type splicing pattern of a messenger RNA transcript of the gene; or a non-wild-type level of 69087, 15821, or 15418 RNA or protein.

Methods of the invention can be used for prenatal screening or to determine if a subject's offspring will be at risk for a disorder.

In preferred embodiments the method includes determining the structure of a 69087, 15821, or 15418 gene, an abnormal structure being indicative of risk for the disorder.

In preferred embodiments the method includes contacting a sample form the subject with an antibody to the 69087, 15821, or 15418 protein or a nucleic acid, which hybridizes specifically with the gene. These and other embodiments are discussed below.

Diagnostic and Prognostic Assays

The presence, level, or absence of 69087, 15821, or 15418 protein or nucleic acid in a biological sample can be evaluated by obtaining a biological sample from a test subject and contacting the biological sample with a compound or an agent capable of detecting the corresponding protein or nucleic acid (e.g., mRNA, genomic DNA) that encodes the corresponding protein such that the presence of the protein or nucleic acid is detected in the biological sample. The term "biological sample" includes tissues, cells and biological fluids isolated from a subject, as well as tissues, cells and fluids present within a subject. A preferred biological sample is serum. The level of expression of the 69087, 15821, or 15418 gene can be measured in a number of ways, including, but not limited to: measuring the mRNA encoded by the 69087, 15821, or 15418 gene; measuring the amount of protein encoded by the 69087, 15821, or 15418 gene; or measuring the activity of the protein encoded by the 69087, 15821, or 15418 gene.

The level of mRNA corresponding to the 69087, 15821, or 15418 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 69087, 15821, or 15418 nucleic acid, such as the nucleic acid of one of SEQ ID NOs: 1, 21, and 41, or a portion thereof, such as an oligonucleotide of at least 7, 15, 30, 50, 100, 250 or 500 nucleotides in length and sufficient to specifically hybridize under stringent conditions to 69087, 15821, or 15418 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 69087, 15821, and 15418 genes.

The level of mRNA in a sample that is encoded by 69087, 15821, or 15418 can be evaluated with nucleic acid amplification, e.g., by RT-PCR (U.S. Pat. No. 4,683,202), ligase chain reaction (Barany, 1991, Proc. Natl. Acad. Sci. USA 88:189–193), self-sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), rolling circle replication (U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5'- or 3'-regions of a 69087, 15821, or 15418 gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence between the primers.

For in situ methods, a cell or tissue sample can be prepared/processed and immobilized on a support, typically a glass slide, and then contacted with a probe that can hybridize to mRNA that encodes the 69087, 15821, or 15418 gene being analyzed.

In another embodiment, the methods include further contacting a control sample with a compound or agent capable of detecting mRNA or genomic DNA corresponding to 69087, 15821, or 15418, and comparing the presence of the mRNA or genomic DNA in the control sample with the presence of the mRNA or genomic DNA in the test sample.

A variety of methods can be used to determine the level of protein encoded by 69087, 15821, or 15418. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 69087, 15821, or 15418 protein in a biological sample in vitro as well as in vivo. In vitro techniques for detection of 69087, 15821, or 15418 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 69087, 15821, or 15418 protein include introducing into a subject a labeled anti-69087, anti-15821, or anti-15418 antibody. For example, the antibody can be labeled with a radioactive marker whose presence and location in a subject can be detected by standard imaging techniques.

In another embodiment, the methods further include contacting the control sample with a compound or agent capable of detecting 69087, 15821, or 15418 protein, and comparing the presence of the protein in the control sample with the presence of the protein in the test sample.

The invention also includes kits for detecting the presence of 69087, 15821, or 15418 in a biological sample. For example, the kit can include a compound or agent capable of detecting 69087, 15821, or 15418 protein or mRNA in a biological sample, and a standard. The compound or agent can be packaged in a suitable container. The kit can further comprise instructions for using the kit to detect the corresponding protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably-labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with malexpressed, aberrant or unwanted 69087, 15821, or 15418 expression or activity. As used herein, the term "unwanted" includes an unwanted phenomenon involved in a biological response such as induction of an inappropriate immune response or deregulated cell proliferation.

In one embodiment, a disease or disorder associated with aberrant or unwanted 69087, 15821, or 15418 expression or activity is identified. A test sample is obtained from a subject and 69087, 15821, or 15418 protein or nucleic acid (e.g., mRNA or genomic DNA) is evaluated, wherein the level, e.g., the presence or absence, of the corresponding protein or nucleic acid is diagnostic for a subject having or at risk of developing a disease or disorder associated with aberrant or unwanted 69087, 15821, or 15418 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 69087, 15821, or 15418 expression or activity. For example, such methods can be used to determine whether a subject can be effectively treated with an agent that modulates 69087, 15821, or 15418 expression or activity.

The methods of the invention can also be used to detect genetic alterations in a 69087, 15821, or 15418 gene, thereby determining if a subject with the altered gene is at risk for a disorder characterized by misregulation in the corresponding protein activity or nucleic acid expression, such as a disorder associated with tumorigenesis or induction of an inappropriate immune response. In preferred embodiments, the methods include detecting, in a sample from the subject, the presence or absence of a genetic alteration characterized by at least one of an alteration affecting the integrity of a gene encoding a 69087, 15821, or 15418 protein, or the malexpression of the 69087, 15821, or 15418 gene. For example, such genetic alterations can be detected by ascertaining the existence of at least one of 1) a deletion of one or more nucleotides from a 69087, 15821, or 15418 gene; 2) an addition of one or more nucleotides to a 69087, 15821, or 15418 gene; 3) a substitution of one or more nucleotides of a 69087, 15821, or 15418 gene, 4) a chromosomal rearrangement of a 69087, 15821, or 15418 gene; 5) an alteration in the level of a messenger RNA transcript of a 69087, 15821, or 15418 gene, 6) aberrant modification of a 69087, 15821, or 15418 gene, such as of the methylation pattern of the genomic DNA, 7) the presence of a non-wild-type splicing pattern of a messenger RNA transcript of a 69087, 15821, or 15418 gene, 8) a non-wild-type level of a 69087, 15821, or 15418 protein, 9) allelic loss of a 69087, 15821, or 15418 gene, and 10) inappropriate post-translational modification of a 69087, 15821, or 15418 protein.

An alteration can be detected without a probe/primer in a polymerase chain reaction, such as anchor PCR or RACE- PCR, or, alternatively, in a ligation chain reaction (LCR), the latter of which can be particularly useful for detecting point mutations in the 69087, 15821, or 15418 gene. This method can include the steps of collecting a sample of cells from a subject, isolating nucleic acid (e.g., genomic, mRNA or both) from the sample, contacting the nucleic acid sample with one or more primers which specifically hybridize to a 69087, 15821, or 15418 gene under conditions such that hybridization and amplification of the gene occurs (if present), and detecting the presence or absence of an amplification product, or detecting the size of the amplification product and comparing the length to a control sample. It is anticipated that PCR and/or LCR can be desirable to use as a preliminary amplification step in conjunction with any of the techniques used for detecting mutations described herein.

Alternative amplification methods include: self sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), or other nucleic acid amplification methods, followed by the detection of the amplified molecules using techniques known to those of skill in the art.

In another embodiment, mutations in a 69087, 15821, or 15418 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis, and compared. Differences in fragment length sizes between sample and control DNA indicates mutations in the sample DNA. Moreover, the use of sequence specific ribozymes (e.g., U.S. Pat. No. 5,498,531) can be used to score for the presence of specific mutations by development or loss of a ribozyme cleavage site.

In other embodiments, genetic mutations in 69087, 15821, or 15418 can be identified by hybridizing a sample to control nucleic acids, e.g., DNA or RNA, by, e.g., two-dimensional arrays, or, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al., 1996, Hum. Mutat. 7:244–255; Kozal et al., 1996, Nature Med. 2:753–759). For example, genetic mutations in 69087, 15821, or 15418 can be identified in two-dimensional arrays containing light-generated DNA probes as described (Cronin et al., supra). Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 69087, 15821, or 15418 gene and detect mutations by comparing the sequence of the sample 69087, 15821, or 15418 with the corresponding wild-type (control) sequence. Automated sequencing procedures can be utilized when performing the diagnostic assays (1995, Biotechniques 19:448), including sequencing by mass spectrometry.

Other methods for detecting mutations in the 69087, 15821, or 15418 gene include methods in which protection from cleavage agents is used to detect mismatched bases in RNA/RNA or RNA/DNA heteroduplexes (Myers et al., 1985, Science 230:1242; Cotton et al., 1988, Proc. Natl. Acad. Sci. USA 85:4397; Saleeba et al., 1992, Meth. Enzymol. 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 69087, 15821, or 15418 cDNAs obtained from samples of cells. For example, the mutY enzyme of *E. coli* cleaves A at G/A mismatches and the thymidine DNA glycosylase from HeLa cells cleaves T at G/T mismatches (Hsu et al., 1994, Carcinogenesis 15:1657–1662; U.S. Pat. No. 5,459,039).

In other embodiments, alterations in electrophoretic mobility will be used to identify mutations in 69087, 15821, or 15418 genes. For example, single strand conformation polymorphism (SSCP) can be used to detect differences in electrophoretic mobility between mutant and wild-type nucleic acids (Orita et al., 1989, Proc. Natl. Acad. Sci. USA 86:2766; Cotton, 1993, Mutat. Res. 285:125–144; Hayashi, 1992, Genet. Anal. Tech. Appl. 9:73–79). Single-stranded DNA fragments of sample and control 69087, 15821, or 15418 nucleic acids will be denatured and allowed to re-nature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., 1991, Trends Genet 7:5).

In yet another embodiment, the movement of mutant or wild-type fragments in polyacrylamide gels containing a gradient of denaturant is assayed using denaturing gradient gel electrophoresis (DGGE) (Myers et al., 1985, Nature 313:495). When DGGE is used as the method of analysis, DNA will be modified to insure that it does not completely denature, for example by adding a GC clamp of approximately 40 base pairs of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension (Saiki et al., 1986, Nature 324:163; Saiki et al., 1989, Proc. Natl. Acad. Sci. USA 86:6230).

Alternatively, allele specific amplification technology that depends on selective PCR amplification can be used in conjunction with the instant invention. Oligonucleotides used as primers for specific amplification can carry the mutation of interest in the center of the molecule (so that amplification depends on differential hybridization; Gibbs et al., 1989, Nucl. Acids Res. 17:2437–2448) or at the extreme 3'-end of one primer where, under appropriate conditions, mismatch can prevent, or reduce polymerase extension (Prossner, 1993, Tibtech 11:238). In addition, it can be desirable to introduce a novel restriction site in the region of the mutation to create cleavage-based detection (Gasparini et al., 1992, Mol. Cell Probes 6:1). It is anticipated that in certain embodiments, amplification can also be performed using Taq ligase for amplification (Barany, 1991, Proc. Natl. Acad. Sci. USA 88:189). In such cases, ligation will occur only if there is a perfect match at the 3'-end of the 5'-sequence making it possible to detect the presence of a known mutation at a specific site by looking for the presence or absence of amplification.

The methods described herein can be performed, for example, using pre-packaged diagnostic kits comprising at least one probe nucleic acid or antibody reagent described herein, which can be conveniently used, e.g., in clinical settings to diagnose patients exhibiting symptoms or family history of a disease or illness involving a 69087, 15821, or 15418 gene.

Use of 69087, 15821, and 15418 Molecules as Surrogate Markers

The 69087, 15821, and 15418 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 69087, 15821, or 15418 molecules of the invention can be detected, and can be correlated with one or more biological states in vivo. For example, the 69087, 15821, or 15418 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers have been described (e.g., Koomen et al., 2000, J. Mass. Spectrom. 35:258–264; James, 1994, AIDS Treat. News Arch. 209).

The 69087, 15821, or 15418 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 69087, 15821, or 15418 marker) transcription or expression, the amplified marker can be in a quantity which is more readily detectable than the drug itself. Also, the marker can be more easily detected due to the nature of the marker itself; for example, using the methods described herein, anti-69087, anti-15821, or anti-15418 antibodies can be employed in an immune-based detection system for a 69087, 15821, or 15418 protein marker, or 69087-, 15821-, or 15418-specific radiolabeled probes can be used to detect a 69087, 15821, or 15418 mRNA marker. Furthermore, the use of a pharmacodynamic marker can offer mechanism-based prediction of risk due to drug treatment beyond the range of possible direct observations. Examples of the use of pharmacodynamic markers have been described (e.g., U.S. Pat. No. 6,033,862; Hattis et al., 1991, Env. Health Perspect. 90: 229–238; Schentag, 1999, Am. J. Health-Syst. Pharm. 56 Suppl. 3: S21–S24; Nicolau, 1999, Am, J. Health-Syst. Pharm. 56 Suppl. 3: S16–S20).

The 69087, 15821, and 15418 molecules of the invention are also useful as pharmacogenomic markers. As used herein, a "pharmacogenomic marker" is an objective biochemical marker which correlates with a specific clinical drug response or susceptibility in a subject (e.g., McLeod et al., 1999, Eur. J. Cancer 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 69087, 15821, or 15418 protein or RNA) for specific tumor markers in a subject, a drug or course of treatment can be selected that is optimized for the treatment of the specific tumor likely to be present in the subject. Similarly, the presence or absence of a specific sequence mutation in 69087, 15821, or 15418 DNA can correlate 69087, 15821, or 15418 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-69087, anti-15821, and anti-15418 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including an agent in the composition that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents and/or adjuvant materials can be included as part of the composition. The tablets, pills, capsules, troches and the like can contain any of the following ingredients, or compounds of a similar nature: a binder, such as microcrystalline cellulose, gum tragacanth or gelatin; an excipient, such as starch or lactose; a disintegrating agent, such as alginic acid, Primogel™, or corn starch; a lubricant, such as magnesium stearate or Sterotes™; a glidant, such as colloidal silicon dioxide; a sweetening agent, such as sucrose or saccharin; or a flavoring agent, such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells using monoclonal antibodies directed towards viral antigens) can also be used as pharmaceutically acceptable carriers. These can be prepared according to described methods (e.g., U.S. Pat. No. 4,522,811).

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 milligrams per kilogram body weight, preferably about 0.01 to 25 milligrams per kilogram body weight, more preferably about 0.1 to 20 milligrams per kilogram body weight, and even more preferably about 1 to 10 milligrams per kilogram, 2 to 9 milligrams per kilogram, 3 to 8 milligrams per kilogram, 4 to 7 milligrams per kilogram, or 5 to 6 milligrams per kilogram body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 milligrams per kilogram of body weight (generally 10 to 20 milligrams per kilogram). If the antibody is to act in the brain, a dosage of 50 to 100 milligrams per kilogram is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for the lipidation of antibodies is described by Cruikshank et al. (1997, J. AIDS Hum. Retrovir. 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including hetero-organic and organo-metallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, and the drug moiety is not to be construed as limited to classical chemical therapeutic agents. For example, the drug moiety can be a protein or polypeptide possessing a desired biological activity. Such proteins can include, for example, a toxin such as abrin, ricin A, gelonin, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukins-1, -2, and -6, granulocyte macrophage colony stimulating factor, granulocyte colony stimulating factor, or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (e.g., Chen et al., 1994, Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 69087, 15821, or 15418 expression or activity. With regards to both prophylactic and therapeutic methods of treatment, such treatments can be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype".) Thus, another aspect of the invention provides methods for tailoring an individual's prophylactic or therapeutic treatment with either the 69087, 15821, or 15418 molecules of the present invention or 69087, 15821, or 15418 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

A therapeutic agent includes, but is not limited to, small molecules, peptides, antibodies, ribozymes and antisense oligonucleotides.

In one aspect, the invention provides a method for preventing a disease or condition in a subject associated with an aberrant or unwanted 69087, 15821, or 15418 expression or activity, by administering to the subject a 69087, 15821, or 15418 molecule or an agent which modulates 69087, 15821, or 15418 expression, or at least one activity of 69087, 15821, or 15418 protein. Subjects at risk for a disease which is caused or contributed to by aberrant or unwanted 69087, 15821, or 15418 expression or activity can be identified by, for example, any or a combination of diagnostic or prognostic assays as described herein. Administration of a prophylactic agent can occur prior to the manifestation of symptoms characteristic of the 69087, 15821, or 15418 aberrance, such that a disease or disorder is prevented or, alternatively, delayed in its progression. Depending on the type of 69087, 15821, or 15418 aberrance, for example, a corresponding protein, agonist, or antagonist agent can be used for treating the subject. The appropriate agent can be determined based on screening assays described herein.

It is possible that some 69087, 15821, or 15418 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 69087, 15821, or 15418 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 69087, 15821, or 15418 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, $F(ab')_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 69087, 15821, or 15418 expression is through the use of aptamer molecules specific for the corresponding protein. Aptamers are nucleic acid molecules having a tertiary structure that permits them to specifically bind to protein ligands (e.g., Osborne et al., 1997, Curr. Opin. Chem. Biol. 1:5–9; Patel, 1997, Curr. Opin. Chem. Biol. 1:32–46). Since nucleic acid molecules can in many cases be more conveniently introduced into target cells than therapeutic protein molecules can be, aptamers offer a method by which 69087, 15821, or 15418 protein activity can be specifically decreased without the introduction of drugs or other molecules which can have pluripotent effects.

Antibodies can be generated that are both specific for target gene product and that reduce target gene product activity. Such antibodies may, therefore, by administered in instances whereby negative modulatory techniques are appropriate for the treatment of 69087, 15821, or 15418 disorders.

In circumstances wherein injection of an animal or a human subject with a 69087, 15821, or 15418 protein or epitope for stimulating antibody production is harmful to the subject, it is possible to generate an immune response against the protein through the use of anti-idiotypic antibodies (e.g., Herlyn, 1999, Ann. Med. 31:66–78;

Bhattacharya-Chatterjee et al., 1998, Cancer Treat. Res. 94:51–68). If an anti-idiotypic antibody is introduced into a mammal or human subject, it should stimulate the production of anti-anti-idiotypic antibodies, which should be specific to the 69087, 15821, or 15418 protein. Vaccines directed to a disease characterized by 69087, 15821, or 15418 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (e.g., Marasco et al., 1993, Proc. Natl. Acad. Sci. USA 90:7889–7893).

The identified compounds that inhibit target gene expression, synthesis and/or activity can be administered to a patient at therapeutically effective doses to prevent, treat or ameliorate 69087, 15821, or 15418 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 69087, 15821, or 15418 activity is used as a template, or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. Detailed reviews of this technique appear in the art (Ansell et al., 1996, Curr. Opin. Biotechnol. 7:89–94; Shea, 1994, Trends Polymer Sci. 2:166–173). Such "imprinted" affinity matrixes are amenable to ligand-binding assays, whereby the immobilized monoclonal antibody component is replaced by an appropriately imprinted matrix (e.g., a matrix described in Vlatakis et al., 1993, Nature 361:645–647. Through the use of isotope-labeling, the "free" concentration of compound which modulates the expression or activity of 69087, 15821, or 15418 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiber optic devices, in turn allowing the dose in a test subject to be quickly optimized based on its individual $IC_{50}$. A rudimentary example of such a "biosensor" is discussed in Kriz et al. (1995, Anal. Chem. 67:2142–2144).

Another aspect of the invention pertains to methods of modulating 69087, 15821, or 15418 expression or activity for therapeutic purposes. Accordingly, in an exemplary embodiment, the modulatory method of the invention involves contacting a cell with a 69087, 15821, or 15418 polypeptide or an agent that modulates one or more of the activities of the protein. An agent that modulates 69087, 15821, or 15418 protein activity can be an agent as described herein, such as a nucleic acid or a protein, a naturally-occurring target molecule of a 69087, 15821, or 15418 protein (e.g., a substrate or receptor), an anti-69087, anti-15821, or anti-15418 antibody, an agonist or antagonist of 69087, 15821, or 15418, a peptidomimetic of a 69087, 15821, or 15418 agonist or antagonist, or another small molecule.

In one embodiment, the agent stimulates one or more activities of 69087, 15821, or 15418 protein. Examples of such stimulatory agents include active 69087, 15821, and 15418 proteins and nucleic acid molecules encoding one of 69087, 15821, and 15418. In another embodiment, the agent inhibits one or more activities of 69087, 15821, or 15418 protein. Examples of such inhibitory agents include antisense 69087, 15821, and 15418 nucleic acid molecules, anti-69087, anti-15821, and anti-15418 antibodies, and inhibitors of 69087, 15821, or 15418 protein activity. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 69087, 15821, or 15418 protein or nucleic acid molecule. In one embodiment, the method involves administering an agent (e.g., an agent identified by a screening assay described herein), or combination of agents that modulates (e.g., up-regulates or down-regulates) 69087, 15821, or 15418 expression or activity. In another embodiment, the method involves administering a 69087, 15821, or 15418 protein or nucleic acid molecule as therapy to compensate for reduced, aberrant, or unwanted expression or activity.

Stimulation of 69087, 15821, or 15418 activity is desirable in situations in which expression of the gene is abnormally down-regulated and/or in which increased activity of the corresponding protein is likely to have a beneficial effect. For example, stimulation of 69087 activity is desirable in situations in which a 69087 is down-regulated and/or in which increased 69087 activity is likely to have a beneficial effect. Likewise, inhibition of 69087 activity is desirable in situations in which 69087 is abnormally up-regulated and/or in which decreased 69087 activity is likely to have a beneficial effect.

Pharmacogenomics

The 69087, 15821, and 15418 molecules of the present invention, as well as agents, or modulators which have a stimulatory or inhibitory effect on 69087, 15821, or 15418 activity (e.g., agents which affect 69087, 15821, or 15418 gene expression) as identified by a screening assay described herein can be administered to individuals to treat (prophylactically or therapeutically) disorders associated with aberrant or unwanted 69087, 15821, or 15418 activity (e.g., disorders associated with tumorigenesis, induction of an inappropriate immune response, or another disorder disclosed herein). In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 69087, 15821, or 15418 molecule or a 69087, 15821, or 15418 modulator as well as tailoring the dosage and/or therapeutic regimen of treatment with a 69087, 15821, or 15418 molecule or a 69087, 15821, or 15418 modulator.

Pharmacogenomics deals with clinically significant hereditary variations in the response to drugs due to altered drug disposition and abnormal action in affected persons (e.g., Eichelbaum et al., 1996, Clin. Exp. Pharmacol. Physiol. 23:983–985; Linder et al., 1997, Clin. Chem. 43:254–266). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP can be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach" can be utilized to identify genes that predict drug response. According to this method, if a gene that encodes a drug's target is known (e.g., a 69087, 15821, or 15418 protein of the present invention), all common variants of that gene can be fairly easily identified in the population and it can be determined if having one version of the gene versus another is associated with a particular drug response.

Alternatively, a method termed "gene expression profiling," can be utilized to identify genes that predict drug response. For example, the gene expression of an animal dosed with a drug (e.g., a 69087, 15821, or 15418 molecule or a 69087, 15821, or 15418 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 69087, 15821, or 15418 molecule or a 69087, 15821, or 15418 modulator, such as a modulator identified by one of the exemplary screening assays described herein.

The present invention further provides methods for identifying new agents, or combinations, that are based on identifying agents that modulate the activity of one or more of the gene products encoded by one or more of the 69087, 15821, and 15418 genes of the present invention, wherein these products can be associated with resistance of the cells to a therapeutic agent. Specifically, the activity of the proteins encoded by the 69087, 15821, and 15418 genes of the present invention can be used as a basis for identifying agents for overcoming agent resistance. By blocking the activity of one or more of the resistance proteins, target cells, e.g., cells of the immune system, will become sensitive to treatment with an agent that the unmodified target cells were resistant to.

Monitoring the influence of agents (e.g., drugs) on the expression or activity of a 69087, 15821, or 15418 protein can be applied in clinical trials. For example, the effectiveness of an agent determined by a screening assay as described herein to increase 69087, 15821, or 15418 gene expression, protein levels, or up-regulate 69087, 15821, or 15418 protein activity, can be monitored in clinical trials of subjects exhibiting decreased 69087, 15821, or 15418 gene expression, protein levels, or down-regulated 69087, 15821, or 15418 protein activity. Alternatively, the effectiveness of an agent determined by a screening assay to decrease 69087, 15821, or 15418 gene expression, decrease 69087, 15821, or 15418 protein levels, or down-regulate 69087, 15821, or 15418 activity, can be monitored in clinical trials of subjects exhibiting increased 69087, 15821, or 15418 gene expression, increased 69087, 15821, or 15418 protein levels, or up-regulated 69087, 15821, or 15418 activity. In such clinical trials, the expression or activity of a 69087, 15821, or 15418 gene, and preferably, other genes that have been implicated in, for example, a 69087-, 15821-, or 15418-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two-dimensional array having a plurality of addresses, each address of the plurality being positionally distinguishable from each other address of the plurality, and each address of the plurality having a unique capture probe, e.g., a nucleic acid or peptide sequence; contacting the array with a 69087, 15821, or 15418, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 69087, 15821, or 15418 nucleic acid, polypeptide, or antibody.

The capture probes can be a set of nucleic acids from a selected sample, e.g., a sample of nucleic acids derived from a control or non-stimulated tissue or cell.

The method can include contacting the 69087, 15821, or 15418 nucleic acid, polypeptide, or antibody with a first array having a plurality of capture probes and a second array having a different plurality of capture probes. The results of hybridization can be compared, e.g., to analyze differences in expression between a first and second sample. The first plurality of capture probes can be from a control sample, e.g., a wild-type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 69087, 15821, or 15418. Such methods can be used to diagnose a subject, e.g., to evaluate risk for a disease or disorder, to evaluate suitability of a selected treatment for a subject, to evaluate whether a subject has a disease or disorder. 69087 and 15418 are associated with protein phosphorylation, thus it is useful for evaluating disorders relating to aberrant protein phosphorylation, such as tumorigenesis and inappropriate cell signaling. 15821 is also associated with aberrant cell signaling, and can be used to evaluate the same kinds of disorders.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 69087, 15821, or 15418 or from a cell or subject in which a 69087-, 15821-, or 15418-mediated response has been elicited, e.g., by contact of the cell with 69087, 15821, or 15418 nucleic acid or protein, or administration to the cell or subject 69087, 15821, or 15418 nucleic acid or protein; contacting the array with one or more inquiry probe, wherein an inquiry probe can be a nucleic acid, polypeptide, or antibody (which is preferably other than 69087, 15821, or 15418 nucleic acid, polypeptide, or antibody); providing a two-dimensional array having a plurality of addresses, each address of the plurality being positionally distinguishable from each other address of the plurality, and each address of the plurality having a unique capture probe, e.g., wherein the capture probes are from a cell or subject which does not express the 69087, 15821, or 15418 (or does not express as highly as in the case of the 69087-, 15821-, or 15418-positive plurality of capture probes) or from a cell or subject which in which a 69087-, 15821-, or 15418-mediated response has not been elicited (or has been elicited to a lesser extent than in the first sample); contacting the array with one or more inquiry probes (which is preferably other than a 69087, 15821, or 15418 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or malexpress 69087, 15821, or 15418 or from a cell or subject in which a 69087-, 15821-, or 15418-mediated response has been elicited, e.g., by contact of the cell with 69087, 15821, or 15418 nucleic acid or protein, or administration to the cell or subject a 69087, 15821, or 15418 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 69087, 15821, or 15418 (or does not express as highly as in the case of the 69087-, 15821-, or 15418-positive plurality of capture probes) or from a cell or subject which in which a 69087-, 15821-, or 15418-mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 69087, 15821, or 15418, e.g., analyzing structure, function, or relatedness to other nucleic acid or amino acid sequences. The method includes: providing a 69087, 15821, or 15418 nucleic acid or amino acid sequence, e.g., nucleotide sequence from 69087, 15821, or 15418 or a portion thereof; comparing the 69087, 15821, or 15418 sequence with one or more preferably a plurality of sequences from a collection of sequences, e.g., a nucleic acid or protein sequence database; to thereby analyze 69087, 15821, or 15418.

The method can include evaluating the sequence identity between a 69087, 15821, or 15418 sequence and a database sequence. The method can be performed by accessing the database at a second site, e.g., via the internet.

In another aspect, the invention features, a set of oligonucleotides, useful, e.g., for identifying SNPs, or identifying specific alleles of 69087, 15821, or 15418. The set includes a plurality of oligonucleotides, each of which has a different nucleotide at an interrogation position, e.g., an SNP or the site of a mutation. In a preferred embodiment, the plurality of oligonucleotides are identical in sequence with one another (except for differences in length). The oligonucleotides can be provided with differential labels, such that an oligonucleotide that hybridizes to one allele provides a signal that is distinguishable from an oligonucleotide that hybridizes to a second allele.

The sequence of a 69087, 15821, or 15418 molecules is provided in a variety of mediums to facilitate use thereof. A sequence can be provided as a manufacture, other than an isolated nucleic acid or amino acid molecule, which contains a 69087, 15821, or 15418. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form.

A 69087, 15821, or 15418 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect™ and Microsoft Word™, or represented in the form of an ASCII file, stored in a database application, such as DB2, Sybase™, Oracle™, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention that match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, can be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBIA).

Thus, the invention features a method of making a computer readable record of a sequence of a 69087, 15821, or 15418 sequence that includes recording the sequence on a computer readable matrix. In a preferred embodiment, the record includes one or more of the following: identification of an open reading frame; identification of a domain, region, or site; identification of the start of transcription; identification of the transcription terminator; the full length amino acid sequence of the protein, or a mature form thereof; the 5'- end of the translated region; or 5'- and/or 3'-regulatory regions.

In another aspect, the invention features, a method of analyzing a sequence. The method includes: providing a 69087, 15821, or 15418 sequence or record, in computer readable form; comparing a second sequence to the gene name sequence; thereby analyzing a sequence. Comparison can include comparing to sequences for sequence identity or determining if one sequence is included within the other, e.g., determining if the 69087, 15821, or 15418 sequence includes a sequence being compared. In a preferred embodiment, the 69087, 15821, or 15418 or second sequence is stored on a first computer, e.g., at a first site and the comparison is performed, read, or recorded on a second computer, e.g., at a second site. E.g., the 69087, 15821, or 15418 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5'-end of the translated region; or 5'- and/or 3'-regulatory regions.

This invention is further illustrated by the following examples that should not be construed as limiting. The contents of all references, patents and published patent applications cited throughout this application are incorporated herein by reference.

EXAMPLES

Example 1

Identification and Characterization of Human 69087 cDNA

The human 69087 nucleotide sequence (FIG. 1; SEQ ID NO: 1), which is approximately 2198 nucleotides in length including non-translated regions, contains a predicted methionine-initiated coding sequence at about nucleotide residues 291–1949. The coding sequence encodes a 553 amino acid protein (SEQ ID NO: 2).

Example 2

Identification and Characterization of Human 15821 cDNA

The human 15821 nucleotide sequence (FIG. 4; SEQ ID NO: 21), which is approximately 3003 nucleotides in length including non-translated regions, contains a predicted methionine-initiated coding sequence at about nucleotide residues 235–1926. The coding sequence encodes a 564 amino acid protein (SEQ ID NO: 22).

Example 3

Identification and Characterization of Human 15418 cDNA

The human 15418 nucleotide sequence (FIG. 8; SEQ ID NO: 41), which is approximately 923 nucleotides in length including non-translated regions, contains a predicted methionine-initiated coding sequence at about nucleotide residues 164–733. The coding sequence encodes a 190 amino acid protein (SEQ ID NO: 42).

Example 4

Tissue Distribution of 69087, 15821, or 15418 mRNA

Northern blot hybridizations with various RNA samples can be performed under standard conditions and washed under stringent conditions, i.e., 0.2×SSC at 65° C. A DNA probe corresponding to all or a portion of the 69087, 15821, or 15418 cDNA (e.g., one of SEQ ID NOs: 1, 21, and 41) can be used. The DNA can, for example, be radioactively labeled with $^{32}$P-dCTP using the Prime-It™ Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb™ hybridization solution (Clontech) and washed at high stringency according to manufacturer's recommendations.

Example 5

Recombinant Expression of 69087, 15821, or 15418 in Bacterial Cells

In this example, 69087, 15821, or 15418 is expressed as a recombinant glutathione-S-transferase (GST) fusion polypeptide in *E. coli* and the fusion polypeptide is isolated and characterized. Specifically, 69087, 15821, or 15418 nucleic acid sequences are fused to GST nucleic acid sequences and this fusion construct is expressed in *E. coli,* e.g., strain PEB199. Expression of the GST-69087, GST-15821, or GST-15418 fusion construct in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 6

Expression of Recombinant 69087, 15821, or 15418 Protein in COS Cells

To express the 69087, 15821, or 15418 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 69087, 15821, or 15418 protein and an HA tag (Wilson et al., 1984, Cell 37:767) or a FLAG® tag fused in-frame to its 3'-end of the fragment is cloned into the polylinker region of the vector, thereby placing the expression of the recombinant protein under the control of the CMV promoter.

To construct the plasmid, the 69087, 15821, or 15418 DNA sequence is amplified by PCR using two primers. The 5' primer contains the restriction site of interest followed by approximately twenty nucleotides of the 69087, 15821, or 15418 coding sequence starting from the initiation codon; the 3'-end sequence contains complementary sequences to the other restriction site of interest, a translation stop codon, the HA tag or FLAG® tag and the last 20 nucleotides of the corresponding coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the gene is inserted in the desired orientation. The ligation mixture is transformed into *E. coli* cells (strains HB101, DH5alpha, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 69087-pcDNA/Amp, 15821-pcDNA/Amp, or 15418-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook et al., (1989, Molecular Cloning: A Laboratory Manual. 2nd ed., Cold Spring Harbor Laboratory Press, Cold Spring Harbor, N.Y.). The expression of the 69087, 15821, or 15418 polypeptide is detected by radiolabeling ($^{35}$S-methionine or $^{35}$-cysteine, available from NEN, Boston, Mass., can be used) and immunoprecipitation (Harlow et al., 1988, Antibodies: A Laboratory Manual, Cold Spring Harbor Laboratory Press, Cold Spring Harbor, N.Y.) using an HA-specific monoclonal antibody. Briefly, the cells are labeled for 8 hours with $^{35}$S-methionine (or $^{35}$S-cysteine). The culture media are then collected and the cells are lysed using detergents (RIPA buffer, 150 millimolar NaCl, 1% NP-40, 0.1% SDS, 0.5% DOC, 50 millimolar Tris, pH 7.5). Both the cell lysate and the culture media are precipitated with an HA-specific monoclonal antibody. Precipitated polypeptides are then analyzed by SDS-PAGE.

Alternatively, DNA containing the 69087, 15821, or 15418 coding sequence is cloned directly into the polylinker of the pcDNA/Amp vector using the appropriate restriction sites. The resulting plasmid is transfected into COS cells in the manner described above, and the expression of the 69087, 15821, or 15418 polypeptide is detected by radiolabeling and immunoprecipitation using a 69087-, 15821-, or 15418-specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:

a) a nucleic acid molecule comprising the nucleic acid sequence of SEQ ID NO:1 or SEQ ID NO:3, or a full complement thereof;

b) a nucleic acid molecule consisting of the nucleic acid sequence of SEQ ID NO:1 or SEQ ID NO:3, or a full complement thereof;

c) a nucleic acid molecule which encodes a polypeptide comprising the amino acid sequence of SEQ ID NO:2, or a full complement thereof; and d) a nucleic acid molecule which encodes a polypeptide consisting of the amino acid sequence of SEQ ID NO:2, or a full complement thereof.

2. The nucleic acid molecule of claim 1, further comprising vector nucleic acid sequences.

3. The nucleic acid molecule of claim 1, further comprising nucleic acid sequences encoding a heterologous polypeptide.

4. An isolated host cell which contains the nucleic acid molecule of claim 2.

5. The host cell of claim 4, which is a mammalian host cell.

6. A method for producing the polypeptide comprising the amino acid sequence of SEQ ID NO:2, comprising culturing the host cell of claim 4 in an appropriate culture medium to produce the polypeptide.

7. A method for producing the polypeptide consisting of the amino acid sequence of SEQ ID NO:2, comprising culturing the host cell of claim 4 in an appropriate culture medium to produce the polypeptide.

* * * * *

SEQUENCE LISTING

<160> NUMBER OF SEQ ID NOS: 44

<210> SEQ ID NO 1
<211> LENGTH: 2198
<212> TYPE: DNA
<213> ORGANISM: Homo sapiens

<400> SEQUENCE: 1
gaccctaaga tgaagggacc tcactatagg gctcgagcgg ccgcccgggc aggtgctttc 60
gccttggcag gtgggagcat gacctatcgt gtgcagttcc tggcgggcta tacatagcca 120
gtcaaagctt cttacaaaag aaacctcttt cacaccctcc acgggtccca cccacaggcc 180
acaggactca ctgtaaatcc cttggacgtt gtctcacccg ggaagggaaa gcagccagca 240
gccctccagc cctcttgtgc tttccctggg agtgcgcccc gtgctcagcc atggtggaca 300
tgggggccct ggacaacctg atcgccaaca ccgcctacct gcaggcccgg aagccctcgg 360
actgcgacag caaagagctg cagcggcggc ggcgtagcct ggccctgccc gggctgcagg 420
gctgcgcgga gctccgccag aagctgtccc tgaacttcca cagcctgtgt gagcagcagc 480
ccatcggtcg ccgcctcttc cgtgacttcc tagccacagt gcccacgttc cgcaaggcgg 540
caaccttcct agaggacgtg cagaactggg agctggccga ggagggaccc accaaagaca 600
gcgcgctgca ggggctggtg gccacttgtg cgagtgcccc tgccccgggg aacccgcaac 660
ccttcctcag ccaggccgtg gccaccaagt gccaagcagc caccactgag gaagagcgag 720
tggctgcagt gacgctgcgc aaggctgagg ccatggcttt cttgcaagag cagcccttta 780
aggatttcgt gaccagcgcc ttctacgaca agtttctgca gtggaaactc ttcgagatgc 840
aaccagtgtc agacaagtac ttcactgagt tcagagtgct ggggaaaggt ggttttgggg 900
aggtatgtgc cgtccaggtg aaaaacactg ggaagatgta tgcctgtaag aaactggaca 960
agaagcggct gaagaagaaa ggtggcgaga agatggctct cttggaaaag gaaatcttgg 1020
agaaggtcag cagccctttc attgtctctc tggcctatgc ctttgagagc aagacccatc 1080
tctgccttgt catgagcctg atgaatgggg gagacctcaa gttccacatc tacaacgtgg 1140
gcacgcgtgg cctggacatg agccgggtga tcttttactc ggcccagata gcctgtggga 1200
tgctgcacct ccatgaactc ggcatcgtct atcgggacat gaagcctgag aatgtgcttc 1260
tggatgacct cggcaactgc aggttatctg acctggggct ggccgtggag atgaagggtg 1320
gcaagcccat cacccagagg gctggaacca atggttacat ggctcctgag atcctaatgg 1380
aaaaggtaag ttattcctat cctgtggact ggtttgccat gggatgcagc atttatgaaa 1440
tggttgctgg acgaacacca ttcaaagatt acaaggaaaa ggtcagtaaa gaggatctga 1500
agcaaagaac tctgcaagac gaggtcaaat tccagcatga taacttcaca gaggaagcaa 1560
aagatatttg caggctcttc ttggctaaga aaccagagca acgcttagga agcagagaaa 1620
agtctgatga tcccaggaaa catcatttct ttaaaacgat caactttcct cgcctggaag 1680
ctggcctaat tgaacccccca tttgtgccag acccttcagt ggtttatgcc aaagacatcg 1740
ctgaaattga tgatttctct gaggttcggg gggtggaatt tgatgacaaa gataagcagt 1800
tcttcaaaaa ctttgcgaca ggtgctgttc ctatagcatg gcaggaagaa attatagaaa 1860
cgggactgtt tgaggaactg aatgacccca acagacctac gggttgtgag gagggtaatt 1920
catccaagtc tggcgtgtgt ttgttattgt aaattgctct ctttaccaga caggcagcag 1980
gagtctcggc tgacataatc ctcgaatgtt ccacacgtgg aaatctgtgg aatgagggct 2040

```
aatcagttag gagggacatc acaaccacaa aacaattcaa aagacaggca agctcactac   2100

tagaacacat tttattttct ttttctttct tcataaagat gagtaaagtc tcagttttca   2160

ctgagggcag ggaaaaggaa cactcaggtt tattttga                           2198


<210> SEQ ID NO 2
<211> LENGTH: 553
<212> TYPE: PRT
<213> ORGANISM: Homo sapiens

<400> SEQUENCE: 2

Met Val Asp Met Gly Ala Leu Asp Asn Leu Ile Ala Asn Thr Ala Tyr
1               5                   10                  15

Leu Gln Ala Arg Lys Pro Ser Asp Cys Asp Ser Lys Glu Leu Gln Arg
            20                  25                  30

Arg Arg Arg Ser Leu Ala Leu Pro Gly Leu Gln Gly Cys Ala Glu Leu
        35                  40                  45

Arg Gln Lys Leu Ser Leu Asn Phe His Ser Leu Cys Glu Gln Gln Pro
    50                  55                  60

Ile Gly Arg Arg Leu Phe Arg Asp Phe Leu Ala Thr Val Pro Thr Phe
65                  70                  75                  80

Arg Lys Ala Ala Thr Phe Leu Glu Asp Val Gln Asn Trp Glu Leu Ala
                85                  90                  95

Glu Glu Gly Pro Thr Lys Asp Ser Ala Leu Gln Gly Leu Val Ala Thr
            100                 105                 110

Cys Ala Ser Ala Pro Ala Pro Gly Asn Pro Gln Pro Phe Leu Ser Gln
        115                 120                 125

Ala Val Ala Thr Lys Cys Gln Ala Ala Thr Thr Glu Glu Glu Arg Val
    130                 135                 140

Ala Ala Val Thr Leu Arg Lys Ala Glu Ala Met Ala Phe Leu Gln Glu
145                 150                 155                 160

Gln Pro Phe Lys Asp Phe Val Thr Ser Ala Phe Tyr Asp Lys Phe Leu
                165                 170                 175

Gln Trp Lys Leu Phe Glu Met Gln Pro Val Ser Asp Lys Tyr Phe Thr
            180                 185                 190

Glu Phe Arg Val Leu Gly Lys Gly Gly Phe Gly Glu Val Cys Ala Val
        195                 200                 205

Gln Val Lys Asn Thr Gly Lys Met Tyr Ala Cys Lys Lys Leu Asp Lys
    210                 215                 220

Lys Arg Leu Lys Lys Lys Gly Gly Glu Lys Met Ala Leu Leu Glu Lys
225                 230                 235                 240

Glu Ile Leu Glu Lys Val Ser Ser Pro Phe Ile Val Ser Leu Ala Tyr
                245                 250                 255

Ala Phe Glu Ser Lys Thr His Leu Cys Leu Val Met Ser Leu Met Asn
            260                 265                 270

Gly Gly Asp Leu Lys Phe His Ile Tyr Asn Val Gly Thr Arg Gly Leu
        275                 280                 285

Asp Met Ser Arg Val Ile Phe Tyr Ser Ala Gln Ile Ala Cys Gly Met
    290                 295                 300

Leu His Leu His Glu Leu Gly Ile Val Tyr Arg Asp Met Lys Pro Glu
305                 310                 315                 320

Asn Val Leu Leu Asp Asp Leu Gly Asn Cys Arg Leu Ser Asp Leu Gly
                325                 330                 335

Leu Ala Val Glu Met Lys Gly Gly Lys Pro Ile Thr Gln Arg Ala Gly
```

-continued

```
        340                 345                 350

Thr Asn Gly Tyr Met Ala Pro Glu Ile Leu Met Glu Lys Val Ser Tyr
    355                 360                 365

Ser Tyr Pro Val Asp Trp Phe Ala Met Gly Cys Ser Ile Tyr Glu Met
    370                 375                 380

Val Ala Gly Arg Thr Pro Phe Lys Asp Tyr Lys Glu Lys Val Ser Lys
385                 390                 395                 400

Glu Asp Leu Lys Gln Arg Thr Leu Gln Asp Glu Val Lys Phe Gln His
                405                 410                 415

Asp Asn Phe Thr Glu Glu Ala Lys Asp Ile Cys Arg Leu Phe Leu Ala
            420                 425                 430

Lys Lys Pro Glu Gln Arg Leu Gly Ser Arg Glu Lys Ser Asp Asp Pro
        435                 440                 445

Arg Lys His His Phe Phe Lys Thr Ile Asn Phe Pro Arg Leu Glu Ala
    450                 455                 460

Gly Leu Ile Glu Pro Pro Phe Val Pro Asp Pro Ser Val Val Tyr Ala
465                 470                 475                 480

Lys Asp Ile Ala Glu Ile Asp Asp Phe Ser Glu Val Arg Gly Val Glu
                485                 490                 495

Phe Asp Asp Lys Asp Lys Gln Phe Phe Lys Asn Phe Ala Thr Gly Ala
            500                 505                 510

Val Pro Ile Ala Trp Gln Glu Glu Ile Ile Glu Thr Gly Leu Phe Glu
        515                 520                 525

Glu Leu Asn Asp Pro Asn Arg Pro Thr Gly Cys Glu Glu Gly Asn Ser
    530                 535                 540

Ser Lys Ser Gly Val Cys Leu Leu Leu
545                 550


<210> SEQ ID NO 3
<211> LENGTH: 1659
<212> TYPE: DNA
<213> ORGANISM: Homo sapiens

<400> SEQUENCE: 3

atggtggaca tgggggccct ggacaacctg atcgccaaca ccgcctacct gcaggcccgg      60

aagccctcgg actgcgacag caaagagctg cagcggcggc ggcgtagcct ggccctgccc     120

gggctgcagg gctgcgcgga gctccgccag aagctgtccc tgaacttcca cagcctgtgt     180

gagcagcagc ccatcggtcg ccgcctcttc cgtgacttcc tagccacagt gcccacgttc     240

cgcaaggcgg caaccttcct agaggacgtg cagaactggg agctggccga ggagggaccc     300

accaaagaca gcgcgctgca ggggctggtg gccacttgtg cgagtgcccc tgccccgggg     360

aacccgcaac ccttcctcag ccaggccgtg gccaccaagt gccaagcagc caccactgag     420

gaagagcgag tggctgcagt gacgctgcgc aaggctgagg ccatggcttt cttgcaagag     480

cagcccttta aggatttcgt gaccagcgcc ttctacgaca agtttctgca gtggaaactc     540

ttcgagatgc aaccagtgtc agacaagtac ttcactgagt tcagagtgct ggggaaaggt     600

ggttttgggg aggtatgtgc cgtccaggtg aaaaacactg ggaagatgta tgcctgtaag     660

aaactggaca agaagcggct gaagaagaaa ggtggcgaga agatggctct cttggaaaag     720

gaaatcttgg agaaggtcag cagccctttc attgtctctc tggcctatgc ctttgagagc     780

aagacccatc tctgccttgt catgagcctg atgaatgggg gagacctcaa gttccacatc     840

tacaacgtgg gcacgcgtgg cctggacatg agccgggtga tcttttactc ggcccagata     900
```

-continued

```
gcctgtggga tgctgcacct ccatgaactc ggcatcgtct atcgggacat gaagcctgag    960

aatgtgcttc tggatgacct cggcaactgc aggttatctg acctggggct ggccgtggag   1020

atgaagggtg gcaagcccat cacccagagg gctggaacca atggttacat ggctcctgag   1080

atcctaatgg aaaaggtaag ttattcctat cctgtggact ggtttgccat gggatgcagc   1140

atttatgaaa tggttgctgg acgaacacca ttcaaagatt acaaggaaaa ggtcagtaaa   1200

gaggatctga agcaaagaac tctgcaagac gaggtcaaat tccagcatga taacttcaca   1260

gaggaagcaa aagatatttg caggctcttc ttggctaaga aaccagagca acgcttagga   1320

agcagagaaa agtctgatga tcccaggaaa catcatttct ttaaaacgat caactttcct   1380

cgcctggaag ctggcctaat tgaacccccca tttgtgccag acccttcagt ggtttatgcc  1440

aaagacatcg ctgaaattga tgatttctct gaggttcggg gggtggaatt tgatgacaaa   1500

gataagcagt tcttcaaaaa ctttgcgaca ggtgctgttc ctatagcatg gcaggaagaa   1560

attatagaaa cgggactgtt tgaggaactg aatgacccca acagacctac gggttgtgag   1620

gagggtaatt catccaagtc tggcgtgtgt ttgttattg                          1659
```

```
<210> SEQ ID NO 4
<211> LENGTH:
<212> TYPE:
<213> ORGANISM:

<400> SEQUENCE: 4

000


<210> SEQ ID NO 5
<211> LENGTH:
<212> TYPE:
<213> ORGANISM:

<400> SEQUENCE: 5

000


<210> SEQ ID NO 6
<211> LENGTH:
<212> TYPE:
<213> ORGANISM:

<400> SEQUENCE: 6

000


<210> SEQ ID NO 7
<211> LENGTH:
<212> TYPE:
<213> ORGANISM:

<400> SEQUENCE: 7

000


<210> SEQ ID NO 8
<211> LENGTH:
<212> TYPE:
<213> ORGANISM:

<400> SEQUENCE: 8

000


<210> SEQ ID NO 9
<211> LENGTH:
```

<212> TYPE:
<213> ORGANISM:

<400> SEQUENCE: 9

000

<210> SEQ ID NO 10
<211> LENGTH:
<212> TYPE:
<213> ORGANISM:

<400> SEQUENCE: 10

000

<210> SEQ ID NO 11
<211> LENGTH: 553
<212> TYPE: PRT
<213> ORGANISM: Homo sapiens

<400> SEQUENCE: 11

```
Met Val Asp Met Gly Ala Leu Asp Asn Leu Ile Ala Asn Thr Ala Tyr
1               5                   10                  15

Leu Gln Ala Arg Lys Pro Ser Asp Cys Asp Ser Lys Glu Leu Gln Arg
            20                  25                  30

Arg Arg Arg Ser Leu Ala Leu Pro Gly Leu Gln Gly Cys Ala Glu Leu
        35                  40                  45

Arg Gln Lys Leu Ser Leu Asn Phe His Ser Leu Cys Glu Gln Gln Pro
    50                  55                  60

Ile Gly Arg Arg Leu Phe Arg Asp Phe Leu Ala Thr Val Pro Thr Phe
65                  70                  75                  80

Arg Lys Ala Ala Thr Phe Leu Glu Asp Val Gln Asn Trp Glu Leu Ala
                85                  90                  95

Glu Glu Gly Pro Thr Lys Asp Ser Ala Leu Gln Gly Leu Val Ala Thr
            100                 105                 110

Cys Ala Ser Ala Pro Ala Pro Gly Asn Pro Gln Pro Phe Leu Ser Gln
        115                 120                 125

Ala Val Ala Thr Lys Cys Gln Ala Ala Thr Thr Glu Glu Glu Arg Val
    130                 135                 140

Ala Ala Val Thr Leu Ala Lys Ala Glu Ala Met Ala Phe Leu Gln Glu
145                 150                 155                 160

Gln Pro Phe Lys Asp Phe Val Thr Ser Ala Phe Tyr Asp Lys Phe Leu
                165                 170                 175

Gln Trp Lys Leu Phe Glu Met Gln Pro Val Ser Asp Lys Tyr Phe Thr
            180                 185                 190

Glu Phe Arg Val Leu Gly Lys Gly Gly Phe Gly Glu Val Cys Ala Val
        195                 200                 205

Gln Val Lys Asn Thr Gly Lys Met Tyr Ala Cys Lys Lys Leu Asp Lys
    210                 215                 220

Lys Arg Leu Lys Lys Lys Gly Gly Glu Lys Met Ala Leu Leu Glu Lys
225                 230                 235                 240

Glu Ile Leu Glu Lys Val Ser Ser Pro Phe Ile Val Ser Leu Ala Tyr
                245                 250                 255

Ala Phe Glu Ser Lys Thr His Leu Cys Leu Val Met Ser Leu Met Asn
            260                 265                 270

Gly Gly Asp Leu Lys Phe His Ile Tyr Asn Val Gly Thr Arg Gly Leu
        275                 280                 285
```

-continued

```
Asp Met Ser Arg Val Ile Phe Tyr Ser Ala Gln Ile Ala Cys Gly Met
    290                 295                 300

Leu His Leu His Glu Leu Gly Ile Val Tyr Arg Asp Met Lys Pro Glu
305                 310                 315                 320

Asn Gly Leu Leu Asp Asp Leu Gly Asn Cys Arg Leu Ser Asp Leu Gly
                325                 330                 335

Leu Ala Val Glu Met Lys Gly Gly Lys Pro Ile Thr Gln Arg Ala Gly
            340                 345                 350

Thr Asn Gly Tyr Met Ala Pro Glu Ile Leu Met Glu Lys Val Ser Tyr
        355                 360                 365

Ser Tyr Pro Val Asp Trp Phe Ala Met Gly Cys Ser Ile Tyr Glu Met
    370                 375                 380

Val Ala Gly Arg Thr Pro Phe Lys Asp Tyr Lys Glu Lys Val Ser Lys
385                 390                 395                 400

Glu Asp Leu Lys Gln Arg Thr Leu Gln Asp Glu Val Lys Phe Gln His
                405                 410                 415

Asp Asn Phe Thr Glu Glu Ala Lys Asp Ile Cys Arg Leu Phe Leu Ala
            420                 425                 430

Lys Lys Pro Glu Gln Arg Leu Arg Ser Arg Glu Lys Ser Asp Asp Pro
        435                 440                 445

Arg Lys His His Phe Phe Lys Thr Ile Asn Phe Pro Arg Leu Glu Ala
    450                 455                 460

Gly Leu Ile Glu Pro Pro Phe Val Pro Asp Pro Ser Val Val Tyr Ala
465                 470                 475                 480

Lys Asp Ile Ala Glu Ile Asp Asp Phe Ser Glu Val Arg Gly Val Glu
                485                 490                 495

Phe Asp Asp Lys Asp Lys Gln Phe Phe Lys Asn Phe Ala Thr Gly Ala
            500                 505                 510

Val Pro Ile Ala Trp Gln Glu Glu Ile Ile Glu Thr Gly Leu Phe Glu
        515                 520                 525

Glu Leu Asn Asp Pro Asn Arg Pro Thr Gly Cys Glu Glu Gly Asn Ser
    530                 535                 540

Ser Lys Ser Gly Val Cys Leu Leu Leu
545                 550


<210> SEQ ID NO 12
<211> LENGTH: 548
<212> TYPE: PRT
<213> ORGANISM: Spermophilus tridecemlineatus

<400> SEQUENCE: 12

Met Asp Met Gly Gly Leu Asp Asn Leu Ile Ala Asn Thr Ala Tyr Leu
1               5                   10                  15

Gln Ala Arg Lys Thr Asp Ser Asp Ser Arg Glu Leu Gln Arg Arg Arg
            20                  25                  30

Arg Ser Leu Ala Leu Pro Gly Pro Gln Gly Cys Ala Glu Leu Arg Gln
        35                  40                  45

Ser Leu Ser Pro His Phe His Ser Leu Cys Glu Gln Gln Pro Ile Gly
    50                  55                  60

Arg Arg Leu Phe Arg Asp Phe Leu Ala Thr Val Pro Lys Tyr Ser Gln
65                  70                  75                  80

Ala Val Ala Phe Leu Glu Asp Val Gln Asn Trp Glu Leu Ala Glu Glu
                85                  90                  95

Gly Pro Ala Lys Thr Ser Thr Leu Gln Gln Leu Ala Ala Thr Cys Ala
            100                 105                 110
```

```
Arg Asp Pro Gly Pro Gln Ser Phe Leu Ser Gln Asp Leu Ala Thr Lys
        115                 120                 125

Cys Arg Ala Ala Ser Thr Asp Glu Glu Arg Lys Thr Leu Val Glu Gln
    130                 135                 140

Ala Lys Ala Glu Thr Met Ser Phe Leu Gln Glu Gln Pro Phe Gln Asp
145                 150                 155                 160

Phe Leu Ala Ser Pro Phe Tyr Asp Arg Phe Leu Gln Trp Lys Leu Phe
                165                 170                 175

Glu Met Gln Pro Val Ser Asp Lys Tyr Phe Thr Glu Phe Arg Val Leu
            180                 185                 190

Gly Lys Gly Gly Phe Gly Glu Val Cys Ala Val Gln Val Arg Asn Thr
        195                 200                 205

Gly Lys Met Tyr Ala Cys Lys Lys Leu Asp Lys Lys Arg Leu Lys Lys
    210                 215                 220

Lys Gly Gly Glu Lys Met Ala Leu Leu Glu Lys Glu Ile Leu Glu Lys
225                 230                 235                 240

Val Asn Ser Pro Phe Ile Val Ser Leu Ala Tyr Ala Phe Glu Ser Lys
                245                 250                 255

Thr His Leu Cys Leu Val Met Ser Leu Met Asn Gly Gly Asp Leu Lys
            260                 265                 270

Phe His Ile Tyr Asn Val Gly Thr Arg Gly Leu Ala Met Ser Arg Val
        275                 280                 285

Ile Phe Tyr Thr Ala Gln Met Thr Cys Gly Val Leu His Leu His Gly
    290                 295                 300

Leu Gly Ile Val Tyr Arg Asp Leu Lys Pro Glu Asn Val Leu Leu Asp
305                 310                 315                 320

Asp Leu Gly Asn Cys Arg Leu Ser Asp Leu Gly Leu Ala Val Glu Val
                325                 330                 335

Gln Asp Asp Lys Pro Ile Thr Gln Arg Ala Gly Thr Asn Gly Tyr Met
            340                 345                 350

Ala Pro Glu Ile Leu Met Asp Lys Ala Ser Tyr Ser Tyr Pro Val Asp
        355                 360                 365

Trp Phe Ala Met Gly Cys Ser Ile Tyr Glu Met Val Ala Gly Arg Thr
    370                 375                 380

Pro Phe Lys Asp Phe Lys Glu Lys Val Ser Lys Glu Asp Leu Lys Glu
385                 390                 395                 400

Arg Thr Met Lys Asp Glu Val Ala Phe His His Glu Asn Phe Thr Glu
                405                 410                 415

Glu Thr Lys Asp Ile Cys Arg Leu Phe Leu Ala Lys Lys Pro Glu Gln
            420                 425                 430

Arg Leu Gly Ser Arg Glu Lys Ala Asp Asp Pro Arg Lys His Pro Phe
        435                 440                 445

Phe Gln Thr Val Asn Phe Pro Arg Leu Glu Ala Gly Leu Val Glu Pro
    450                 455                 460

Pro Phe Val Pro Asp Pro Ser Val Val Tyr Ala Lys Asp Val Asp Glu
465                 470                 475                 480

Ile Asp Asp Phe Ser Glu Val Arg Gly Val Glu Phe Asp Asp Lys Asp
                485                 490                 495

Lys Gln Phe Phe Gln Arg Phe Ser Thr Gly Ala Val Pro Val Ala Trp
            500                 505                 510

Gln Glu Glu Ile Ile Glu Thr Gly Leu Phe Glu Glu Leu Asn Asp Pro
        515                 520                 525
```

-continued

```
Asn Arg Pro Ser Gly Asp Gly Lys Gly Asp Ser Ser Lys Ser Gly Val
    530                 535                 540

Cys Leu Leu Leu
545


<210> SEQ ID NO 13
<211> LENGTH: 557
<212> TYPE: PRT
<213> ORGANISM: Oryzias latipes

<400> SEQUENCE: 13

Met Cys Asp Met Gly Gly Leu Asp Asn Leu Val Ala Asn Thr Ala Tyr
1               5                   10                  15

Leu Lys Ala Gln Gly Gly Asp Asp Lys Glu Met Lys Lys Arg Arg Arg
            20                  25                  30

Ser Leu Ser Leu Pro Lys Pro Glu Gln Cys Val Ala Leu Arg Glu Ser
        35                  40                  45

Ile Glu Lys Asp Phe Thr Leu Leu Cys Glu Arg Gln Pro Ile Gly Lys
    50                  55                  60

Arg Leu Phe Arg Asp Phe Leu Ala Asn Thr Pro Glu Phe Lys Leu Ala
65                  70                  75                  80

Ala Glu Phe Leu Asp Glu Leu Tyr Asp Trp Asp Leu Ala Glu Gly Ala
                85                  90                  95

Ala Lys Asp Lys Ala Arg Gln Asn Ile Ile Asn Lys Tyr Cys Lys Pro
            100                 105                 110

Asp Ser Lys Thr Phe Leu Thr Phe Leu Ser Gly Glu Pro Ala Glu Lys
        115                 120                 125

Cys Lys Ser Val Thr Asp Ala Thr Phe Glu Glu Val Met Lys Asn Lys
    130                 135                 140

Val Gln Asp Gly Val Arg Glu Phe Leu Lys Gly Lys Pro Phe Thr Glu
145                 150                 155                 160

Tyr Gln Gly Ser Gln Tyr Phe Asp Lys Phe Leu Gln Trp Lys Glu Tyr
                165                 170                 175

Glu Lys Gln Pro Ile Ser Asp Lys Tyr Phe Tyr Glu Phe Arg Thr Leu
            180                 185                 190

Gly Lys Gly Gly Phe Gly Glu Val Cys Ala Val Gln Val Lys Asn Thr
        195                 200                 205

Gly Gln Met Tyr Ala Cys Lys Lys Leu Cys Lys Lys Arg Leu Lys Lys
    210                 215                 220

Lys Gly Gly Glu Lys Met Ala Leu Leu Glu Lys Gln Ile Leu Glu Lys
225                 230                 235                 240

Val Asn Ser Leu Phe Leu Val Asn Leu Ala Tyr Ala Tyr Asp Thr Lys
                245                 250                 255

Thr His Leu Cys Leu Val Met Thr Leu Met Asn Gly Gly Asp Leu Lys
            260                 265                 270

Tyr His Ile Tyr Asn Ile Gly Tyr Asp Gly Lys Gly Val Asp Lys Gly
        275                 280                 285

Ile Glu Met Lys Arg Ile Ile His Tyr Thr Ala Gln Ile Thr Thr Gly
    290                 295                 300

Ile Leu His Leu His Asp Met Asp Ile Ile Tyr Arg Asp Met Lys Pro
305                 310                 315                 320

Glu Asn Val Leu Leu Asp Ser Gln Gly Gln Cys Arg Leu Ser Asp Leu
                325                 330                 335

Gly Leu Ala Ile Glu Ile Ala Pro Gly Lys Thr Val Thr Gln Met Ala
            340                 345                 350
```

-continued

```
Gly Thr Gly Ala Tyr Met Ala Pro Glu Ile Leu Ser Lys Thr Pro Tyr
        355                 360                 365

Arg Thr Ser Val Asp Trp Trp Ala Leu Gly Cys Ser Ile Tyr Glu Met
    370                 375                 380

Val Ala Gly Tyr Thr Pro Phe Lys Gly Pro Glu Ser Lys Lys Glu Lys
385                 390                 395                 400

Val Glu Lys Glu Glu Val Gln Arg Arg Ile Leu Asn Glu Glu Pro Lys
                405                 410                 415

Trp Glu His Lys Cys Phe Asp Ala Pro Thr Lys Asp Val Ile Gln Gln
            420                 425                 430

Phe Leu Lys Lys Lys Ile Asp Glu Arg Leu Gly Met Arg Asn Asn Met
        435                 440                 445

Glu Asp Pro Arg Lys His Glu Trp Phe Lys Ser Ile Asn Phe Pro Arg
    450                 455                 460

Leu Glu Ala Gly Leu Val Asp Pro Pro Trp Val Pro Lys Pro Asn Val
465                 470                 475                 480

Val Tyr Ala Lys Asp Thr Gly Asp Ile Ala Glu Phe Ser Glu Ile Lys
                485                 490                 495

Gly Ile Glu Phe Asp Ala Lys Asp Asp Lys Phe Phe Lys Glu Phe Ser
            500                 505                 510

Thr Gly Ala Val Pro Ile Gln Trp Gln Gln Glu Met Ile Glu Thr Gly
        515                 520                 525

Leu Phe Asp Glu Leu Asn Asp Pro Asn Arg Lys Glu Gly Ala Gly Gly
    530                 535                 540

Gly Asp Asp Glu Lys Lys Ser Gly Thr Cys Ala Leu Leu
545                 550                 555


<210> SEQ ID NO 14
<211> LENGTH: 549
<212> TYPE: PRT
<213> ORGANISM: Cyprinus carpio

<400> SEQUENCE: 14

Met Cys Asp Met Gly Gly Leu Asp Asn Leu Val Ala Asn Thr Ala Tyr
1               5                   10                  15

Leu Lys Ala Gln Gly Gly Asp Asp Lys Glu Met Lys Lys Arg Arg Arg
            20                  25                  30

Ser Leu Ser Leu Pro Lys Pro Glu Gln Cys Ala Ala Leu Arg Ser Thr
        35                  40                  45

Leu Asp Lys Asp Phe Glu Ser Leu Cys Glu Lys Gln Pro Ile Gly Lys
    50                  55                  60

Arg Phe Phe Arg Gln Tyr Leu Asp Gln Gly Gly Pro Glu Cys Asn Ala
65                  70                  75                  80

Ala Ala Glu Phe Leu Asp Asp Leu Asn Asp Trp Glu Leu Ser Glu Ala
                85                  90                  95

Ala Ala Lys Asp Lys Ala Arg Thr Asn Ile Ile Asn Lys Phe Cys Lys
            100                 105                 110

Asp Gly Ser Lys Ser Ser Leu Thr Phe Leu Thr Gly Asp Val Ala Thr
        115                 120                 125

Lys Cys Lys Ala Val Thr Asp Lys Asp Phe Glu Glu Val Met Gly Gln
    130                 135                 140

Val Lys Glu Ala Thr Lys Glu Phe Leu Lys Gly Lys Pro Phe Thr Asp
145                 150                 155                 160

Tyr Gln Thr Ser Glu Phe Phe Glu Lys Phe Leu Gln Trp Lys Glu Tyr
```

-continued

```
                165                 170                 175

Glu Lys Gln Pro Ile Thr Glu Lys Tyr Phe Tyr Glu Phe Arg Thr Leu
            180                 185                 190

Gly Lys Gly Gly Phe Gly Glu Val Cys Ala Val Gln Val Lys Asn Thr
        195                 200                 205

Gly Gln Met Tyr Ala Cys Lys Lys Leu Cys Lys Lys Arg Leu Lys Lys
    210                 215                 220

Lys His Gly Glu Lys Met Ala Leu Leu Glu Lys Lys Ile Leu Glu Lys
225                 230                 235                 240

Val Asn Ser Leu Phe Ile Val Ser Leu Ala Tyr Ala Tyr Asp Thr Lys
                245                 250                 255

Thr His Leu Cys Leu Val Met Ser Leu Met Asn Gly Gly Asp Leu Lys
            260                 265                 270

Tyr His Ile Tyr Asn Ile Gly Glu Lys Gly Ile Glu Met Glu Arg Ile
        275                 280                 285

Ile Tyr Tyr Thr Ala Gln Ile Thr Thr Gly Met Leu Gln Leu His Asn
    290                 295                 300

Met Asp Ile Val Tyr Arg Asp Met Lys Pro Glu Asn Val Leu Leu Asp
305                 310                 315                 320

Ser Gln Gly Gln Cys Arg Leu Ser Asp Leu Gly Leu Ala Val Glu Ile
                325                 330                 335

Pro Val Gly Lys Thr Thr Thr Gln Lys Ala Gly Thr Gly Ala Tyr Met
            340                 345                 350

Ala Pro Glu Ile Leu Thr Glu Thr Pro Tyr Arg Thr Ser Val Asp Trp
        355                 360                 365

Trp Ala Leu Gly Cys Ser Ile Tyr Glu Met Val Ala Gly Tyr Thr Pro
    370                 375                 380

Phe Lys Gly Pro Glu Ala Lys Lys Glu Lys Val Glu Lys Glu Glu Val
385                 390                 395                 400

Gln Arg Arg Ile Ile Asn Glu Glu Pro Lys Phe Glu His Lys Asn Phe
                405                 410                 415

Asn Ala Pro Thr Ile Asp Ile Ile Lys Gln Phe Leu Lys Lys Lys Ile
            420                 425                 430

Asp Glu Arg Leu Gly Cys Lys Gly Asp Asp Pro Arg Lys His Glu Trp
        435                 440                 445

Phe Lys Ser Ile Asn Phe Ala Arg Leu Glu Ala Gly Leu Ile Asp Pro
    450                 455                 460

Pro Trp Val Pro Lys Pro Asn Val Val Tyr Ala Lys Asp Thr Gly Asp
465                 470                 475                 480

Ile Ala Glu Phe Ser Glu Ile Lys Gly Ile Glu Phe Asp Ala Lys Asp
                485                 490                 495

Glu Lys Phe Phe Lys Glu Phe Ser Thr Gly Ala Val Ser Ile Ala Trp
            500                 505                 510

Gln Lys Glu Met Ile Asp Thr Gly Leu Phe Asp Glu Leu Asn Asp Pro
        515                 520                 525

Asn Arg Lys Glu Ser Ser Gly Gly Leu Asp Asp Asp Lys Lys Ser Gly
    530                 535                 540

Thr Cys Thr Leu Leu
545

<210> SEQ ID NO 15
<211> LENGTH:
<212> TYPE:
<213> ORGANISM:
```

<400> SEQUENCE: 15

000

<210> SEQ ID NO 16
<211> LENGTH:
<212> TYPE:
<213> ORGANISM:

<400> SEQUENCE: 16

000

<210> SEQ ID NO 17
<211> LENGTH:
<212> TYPE:
<213> ORGANISM:

<400> SEQUENCE: 17

000

<210> SEQ ID NO 18
<211> LENGTH:
<212> TYPE:
<213> ORGANISM:

<400> SEQUENCE: 18

000

<210> SEQ ID NO 19
<211> LENGTH:
<212> TYPE:
<213> ORGANISM:

<400> SEQUENCE: 19

000

<210> SEQ ID NO 20
<211> LENGTH:
<212> TYPE:
<213> ORGANISM:

<400> SEQUENCE: 20

000

<210> SEQ ID NO 21
<211> LENGTH: 3003
<212> TYPE: DNA
<213> ORGANISM: Homo sapiens

<400> SEQUENCE: 21
ggggcgaaga gagggctgaa cccgtccgct gcccgggcgg tggagccccc acggcgaggc 60
gctgcgccgg cggtggagac tcgcgttccc tccagcccct ggggcagaac tttctcgccc 120
cccctcctcc ctcccccgca gtcggactcc ctccccagcc ggccagtcct cccggaggag 180
aaggcgccgc ggagacagcc cgggcggggg cctaccttcc ccagggcagg catcatgtcg 240
gcggcgcagg tgtcctcgtc ccggagacaa tcttgctacc tgtgcgacct gccccgcatg 300
ccctgggcca tgatctggga cttctcggaa cccgtatgcc gcggttgcgt caactacgag 360
ggcgctgatc gcatcgaatt cgtgatcgag acagcgcgcc agctgaagcg ggcgcacggc 420
tgcttcccgg agggtcgctc cccacccggc gccgcggcct cggccgccgc caagccgccg 480

-continued

```
ccgctctccg ccaaggacat ccttttgcag cagcagcagc agcttggcca cggcggcccc    540
gaggcggccc cgcgcgcgcc gcaggccttg gagcgctacc cgttggcggc cgcggccgag    600
aggcccccgc gcctcggctc tgacttcggc agcagccgcc cggcagcgag cctggcccag    660
ccgccgacgc cgcagccgcc gcccgtgaac ggcatcctgg tgcccaacgg cttctccaag    720
ctagaggagc cgcccgagct gaatcgccag agcccgaacc cgcggcgcgg ccacgcggtg    780
ccgcccaccc tggtgccgct catgaacggc tcggccacgc cggcggccgc cagcctgggc    840
tccgcgcagc ccaccgatct gggcgcccac aagcggccgg catccgtgtc gagcagcgct    900
gccgtggagc acgagcagcg tgaggcggca gccaaggaga aacaaccgcc gccgcctgcg    960
caccggggcc cggccgacag cctgtccacc gcggccgggg ccgccgagct gagcgcggaa   1020
ggtgcgggca agagccgcgg gtctggagag caggactggg tcaacaggcc caagaccgtg   1080
cgcgacacgc tgctggcgct gcaccagcac ggccactcgg ggcccttcga gagcaagttt   1140
aagaaggagc cggccctgac tgcaggcagg ttgttgggtt tcgaggccaa cggggccaac   1200
gggtctaaag cagttgcaag aacagcaagg aaaaggaagc cctctccaga accagaaggt   1260
gaagtcgggc cccctaagat caacggagag gcccagccgt ggctgtccac atccacagag   1320
gggctcaaga tccccatgac tcctacatcc tcttttgtgt ctccgccacc acccactgcc   1380
tcacctcatt ccaaccggac cacaccgcct gaagcggccc agaatggcca gtcccccatg   1440
gcagccctga tcttagtagc agacaatgca gggggcagtc atgcctcaaa agatgccaac   1500
caggttcact ccactaccag gaggaatagc aacagtccgc cctctccgtc ctctatgaac   1560
caaagaaggc tgggccccag agaggtgggg ggccagggag caggcaacac aggaggactg   1620
gagccagtgc accctgccag cctcccggac tcctctctgg caaccagtgc cccgctgtgc   1680
tgcaccctct gccacgagcg gctggaggac acccattttg tgcagtgccc gtccgtccct   1740
tcgcacaagt tctgcttccc ttgctccaga caaagcatca aacagcaggg agctagtgga   1800
gaggtctatt gtcccagtgg ggaaaaatgc cctcttgtgg gctccaatgt cccctgggcc   1860
tttatgcaag ggaaattgc aaccatcctt gctggagatg tgaaagtgaa aaaagagaga   1920
gactcgtgac ttttccggtt tcagaaaaac ccaatgatta cccttaatta aaactgcttg   1980
aattgtatat atatctccat atatatatat atccaagaca agggaaatgt agacttcata   2040
aacatggctg tataattttg atttttttg aatacattgt gtttctatat tttttttgac   2100
gacaaaaggt atgtacttat aaagacattt ttttcttttg ttaacgttat tagcatatct   2160
ttgtgcttta ttatcctggt gacagttacc gttctatgta ggctgtgact tgcgctgctt   2220
ttttagagca cttggcaaat cagaaatgct tctagctgta tttgtatgca cttattttaa   2280
aaagaaaaaa aaagccaaat acattttctg aacttttgta agattgcctt actgtctgtc   2340
attccttatt gctggcccct ttctcaggcc ggaggccaag tggtggagaa ggaaaggaaa   2400
tgatcgaacg ggcatgttgt caagtgggca tgccactggg aaataccacc agtttaccct   2460
gaaacattgt cctcagagga gtaggaaagt ggattttgaa tctctatttt gctcaaaagt   2520
tcagttcctg agatactgat gactgagagt gctgctggga aattttcagg attgtgtggt   2580
cttttggggt tttttgtttt ttttttttta agacaaagtt gaccgctgtt cactgtccac   2640
gtgatcagtt gtaagattac aatgctgcat gctagttggt tacataagat acaattccag   2700
tgatggaagg cggttataat ggatggtggt gtgtacaaga tggcactgcc atctttgagc   2760
agagcccagc tctgcagcgc cacttcatct ttttaaacac cctagaggtc tgtttgttgt   2820
tgctgttgtc ctttattttg aaagagttgc aagagaagtt acagtccagg tgaacttgga   2880
```

-continued

```
gattgtggga ttggttttgt ttctgttttg ttttgtttat catttacctg tagtgctatt   2940

gctgttgata ctatcaccta taccctgttt ctagtgagtg ctgaatacag tatggtacaa   3000

tga                                                                 3003


<210> SEQ ID NO 22
<211> LENGTH: 564
<212> TYPE: PRT
<213> ORGANISM: Homo sapiens

<400> SEQUENCE: 22

Met Ser Ala Ala Gln Val Ser Ser Ser Arg Arg Gln Ser Cys Tyr Leu
1               5                   10                  15

Cys Asp Leu Pro Arg Met Pro Trp Ala Met Ile Trp Asp Phe Ser Glu
            20                  25                  30

Pro Val Cys Arg Gly Cys Val Asn Tyr Glu Gly Ala Asp Arg Ile Glu
        35                  40                  45

Phe Val Ile Glu Thr Ala Arg Gln Leu Lys Arg Ala His Gly Cys Phe
    50                  55                  60

Pro Glu Gly Arg Ser Pro Pro Gly Ala Ala Ala Ser Ala Ala Ala Lys
65                  70                  75                  80

Pro Pro Pro Leu Ser Ala Lys Asp Ile Leu Leu Gln Gln Gln Gln Gln
                85                  90                  95

Leu Gly His Gly Gly Pro Glu Ala Ala Pro Arg Ala Pro Gln Ala Leu
            100                 105                 110

Glu Arg Tyr Pro Leu Ala Ala Ala Ala Glu Arg Pro Pro Arg Leu Gly
        115                 120                 125

Ser Asp Phe Gly Ser Ser Arg Pro Ala Ala Ser Leu Ala Gln Pro Pro
    130                 135                 140

Thr Pro Gln Pro Pro Pro Val Asn Gly Ile Leu Val Pro Asn Gly Phe
145                 150                 155                 160

Ser Lys Leu Glu Glu Pro Pro Glu Leu Asn Arg Gln Ser Pro Asn Pro
                165                 170                 175

Arg Arg Gly His Ala Val Pro Pro Thr Leu Val Pro Leu Met Asn Gly
            180                 185                 190

Ser Ala Thr Pro Ala Ala Ala Ser Leu Gly Ser Ala Gln Pro Thr Asp
        195                 200                 205

Leu Gly Ala His Lys Arg Pro Ala Ser Val Ser Ser Ser Ala Ala Val
    210                 215                 220

Glu His Glu Gln Arg Glu Ala Ala Ala Lys Glu Lys Gln Pro Pro Pro
225                 230                 235                 240

Pro Ala His Arg Gly Pro Ala Asp Ser Leu Ser Thr Ala Ala Gly Ala
                245                 250                 255

Ala Glu Leu Ser Ala Glu Gly Ala Gly Lys Ser Arg Gly Ser Gly Glu
            260                 265                 270

Gln Asp Trp Val Asn Arg Pro Lys Thr Val Arg Asp Thr Leu Leu Ala
        275                 280                 285

Leu His Gln His Gly His Ser Gly Pro Phe Glu Ser Lys Phe Lys Lys
    290                 295                 300

Glu Pro Ala Leu Thr Ala Gly Arg Leu Leu Gly Phe Glu Ala Asn Gly
305                 310                 315                 320

Ala Asn Gly Ser Lys Ala Val Ala Arg Thr Ala Arg Lys Arg Lys Pro
                325                 330                 335

Ser Pro Glu Pro Glu Gly Glu Val Gly Pro Pro Lys Ile Asn Gly Glu
```

-continued

```
            340                 345                 350

Ala Gln Pro Trp Leu Ser Thr Ser Thr Glu Gly Leu Lys Ile Pro Met
        355                 360                 365

Thr Pro Thr Ser Ser Phe Val Ser Pro Pro Pro Thr Ala Ser Pro
    370                 375                 380

His Ser Asn Arg Thr Thr Pro Pro Glu Ala Ala Gln Asn Gly Gln Ser
385                 390                 395                 400

Pro Met Ala Ala Leu Ile Leu Val Ala Asp Asn Ala Gly Gly Ser His
                405                 410                 415

Ala Ser Lys Asp Ala Asn Gln Val His Ser Thr Thr Arg Arg Asn Ser
            420                 425                 430

Asn Ser Pro Pro Ser Pro Ser Ser Met Asn Gln Arg Arg Leu Gly Pro
        435                 440                 445

Arg Glu Val Gly Gly Gln Gly Ala Gly Asn Thr Gly Gly Leu Glu Pro
    450                 455                 460

Val His Pro Ala Ser Leu Pro Asp Ser Ser Leu Ala Thr Ser Ala Pro
465                 470                 475                 480

Leu Cys Cys Thr Leu Cys His Glu Arg Leu Glu Asp Thr His Phe Val
                485                 490                 495

Gln Cys Pro Ser Val Pro Ser His Lys Phe Cys Phe Pro Cys Ser Arg
            500                 505                 510

Gln Ser Ile Lys Gln Gln Gly Ala Ser Gly Glu Val Tyr Cys Pro Ser
        515                 520                 525

Gly Glu Lys Cys Pro Leu Val Gly Ser Asn Val Pro Trp Ala Phe Met
    530                 535                 540

Gln Gly Glu Ile Ala Thr Ile Leu Ala Gly Asp Val Lys Val Lys Lys
545                 550                 555                 560

Glu Arg Asp Ser

<210> SEQ ID NO 23
<211> LENGTH: 1692
<212> TYPE: DNA
<213> ORGANISM: Homo sapiens

<400> SEQUENCE: 23

atgtcggcgg cgcaggtgtc ctcgtcccgg agacaatctt gctacctgtg cgacctgccc     60

cgcatgccct gggccatgat ctgggacttc tcggaacccg tatgccgcgg ttgcgtcaac    120

tacgagggcg ctgatcgcat cgaattcgtg atcgagacag cgcgccagct gaagcgggcg    180

cacggctgct tcccggaggg tcgctcccca cccggcgccg cggcctcggc cgccgccaag    240

ccgccgccgc tctccgccaa ggacatcctt ttgcagcagc agcagcagct tggccacggc    300

ggccccgagg cggccccgcg cgcgccgcag gccttggagc gctacccgtt ggcggccgcg    360

gccgagaggc ccccgcgcct cggctctgac ttcggcagca gccgcccggc agcgagcctg    420

gcccagccgc cgacgccgca gccgccgccc gtgaacggca tcctggtgcc caacggcttc    480

tccaagctag aggagccgcc cgagctgaat cgccagagcc cgaacccgcg gcgcggccac    540

gcggtgccgc ccaccctggt gccgctcatg aacggctcgg ccacgccggc ggccgccagc    600

ctgggctccg cgcagcccac cgatctgggc gcccacaagc ggccggcatc cgtgtcgagc    660

agcgctgccg tggagcacga gcagcgtgag gcggcagcca aggagaaaca accgccgccg    720

cctgcgcacc ggggcccggc cgacagcctg tccaccgcgg ccggggccgc cgagctgagc    780

gcggaaggtg cgggcaagag ccgcgggtct ggagagcagg actgggtcaa caggcccaag    840
```

-continued

```
accgtgcgcg acacgctgct ggcgctgcac cagcacggcc actcggggcc cttcgagagc     900

aagtttaaga aggagccggc cctgactgca ggcaggttgt tgggtttcga ggccaacggg     960

gccaacgggt ctaaagcagt tgcaagaaca gcaaggaaaa ggaagccctc tccagaacca    1020

gaaggtgaag tcgggccccc taagatcaac ggagaggccc agccgtggct gtccacatcc    1080

acagaggggc tcaagatccc catgactcct acatcctctt ttgtgtctcc gccaccaccc    1140

actgcctcac ctcattccaa ccggaccaca ccgcctgaag cggcccagaa tggccagtcc    1200

cccatggcag ccctgatctt agtagcagac aatgcagggg gcagtcatgc ctcaaaagat    1260

gccaaccagg ttcactccac taccaggagg aatagcaaca gtccgccctc tccgtcctct    1320

atgaaccaaa gaaggctggg ccccagagag gtgggggggcc agggagcagg caacacagga    1380

ggactggagc cagtgcaccc tgccagcctc ccggactcct ctctggcaac cagtgccccg    1440

ctgtgctgca ccctctgcca cgagcggctg gaggacaccc attttgtgca gtgcccgtcc    1500

gtcccttcgc acaagttctg cttcccttgc tccagacaaa gcatcaaaca gcagggagct    1560

agtggagagg tctattgtcc cagtggggaa aaatgccctc ttgtgggctc caatgtcccc    1620

tgggccttta tgcaagggga aattgcaacc atccttgctg gagatgtgaa agtgaaaaaa    1680

gagagagact cg                                                        1692
```

<210> SEQ ID NO 24
<211> LENGTH:
<212> TYPE:
<213> ORGANISM:

<400> SEQUENCE: 24

000

<210> SEQ ID NO 25
<211> LENGTH:
<212> TYPE:
<213> ORGANISM:

<400> SEQUENCE: 25

000

<210> SEQ ID NO 26
<211> LENGTH:
<212> TYPE:
<213> ORGANISM:

<400> SEQUENCE: 26

000

<210> SEQ ID NO 27
<211> LENGTH:
<212> TYPE:
<213> ORGANISM:

<400> SEQUENCE: 27

000

<210> SEQ ID NO 28
<211> LENGTH:
<212> TYPE:
<213> ORGANISM:

<400> SEQUENCE: 28

000

<210> SEQ ID NO 29
<211> LENGTH:
<212> TYPE:
<213> ORGANISM:

<400> SEQUENCE: 29

000

<210> SEQ ID NO 30
<211> LENGTH:
<212> TYPE:
<213> ORGANISM:

<400> SEQUENCE: 30

000

<210> SEQ ID NO 31
<211> LENGTH: 796
<212> TYPE: PRT
<213> ORGANISM: Homo sapiens

<400> SEQUENCE: 31

```
Met Ser Ala Ala Gln Val Ser Ser Ser Arg Arg Gln Ser Cys Tyr Leu
1               5                   10                  15

Cys Asp Leu Pro Arg Met Pro Trp Ala Met Ile Trp Asp Phe Ser Glu
            20                  25                  30

Pro Val Cys Arg Gly Cys Val Asn Tyr Glu Gly Ala Asp Arg Ile Glu
        35                  40                  45

Phe Val Ile Glu Thr Ala Arg Gln Leu Lys Arg Ala His Gly Cys Phe
    50                  55                  60

Gln Asp Gly Arg Ser Pro Gly Pro Pro Pro Pro Val Gly Val Lys Thr
65                  70                  75                  80

Val Ala Leu Ser Ala Lys Glu Ala Ala Ala Ala Ala Ala Ala Ala Ala
                85                  90                  95

Ala Ala Ala Ala Ala Ala Gln Gln Gln Gln Gln Gln Gln Gln Gln Gln
            100                 105                 110

Gln Gln Gln Gln Gln Gln Gln Gln Gln Gln Gln Gln Gln Gln Gln Leu
        115                 120                 125

Asn His Val Asp Gly Ser Ser Lys Pro Ala Val Leu Ala Ala Pro Ser
    130                 135                 140

Gly Leu Glu Arg Tyr Gly Leu Ser Ala Ala Ala Ala Ala Ala Ala Ala
145                 150                 155                 160

Ala Ala Ala Ala Val Glu Gln Arg Ser Arg Phe Glu Tyr Pro Pro Pro
                165                 170                 175

Pro Val Ser Leu Gly Ser Ser Ser His Thr Ala Arg Leu Pro Asn Gly
            180                 185                 190

Leu Gly Gly Pro Asn Gly Phe Pro Lys Pro Thr Pro Glu Glu Gly Pro
        195                 200                 205

Pro Glu Leu Asn Arg Gln Ser Pro Asn Ser Ser Ser Ala Ala Ala Ser
    210                 215                 220

Val Ala Ser Arg Arg Gly Thr His Gly Gly Leu Val Thr Gly Leu Pro
225                 230                 235                 240

Asn Pro Gly Gly Gly Gly Gly Pro Gln Leu Thr Val Pro Pro Asn Leu
                245                 250                 255

Leu Pro Gln Thr Leu Leu Asn Gly Pro Ala Ser Ala Ala Val Leu Pro
            260                 265                 270
```

```
Pro Pro Pro Pro His Ala Leu Gly Ser Arg Gly Pro Pro Thr Pro Ala
        275                 280                 285

Pro Pro Gly Ala Pro Gly Gly Pro Ala Cys Leu Gly Gly Thr Pro Gly
    290                 295                 300

Val Ser Ala Thr Ser Ser Ser Ala Ser Ser Ser Thr Ser Ser Ser Val
305                 310                 315                 320

Ala Glu Val Gly Val Gly Ala Gly Gly Lys Arg Pro Gly Ser Val Ser
                325                 330                 335

Ser Thr Asp Gln Glu Arg Glu Leu Lys Glu Lys Gln Arg Asn Ala Glu
            340                 345                 350

Ala Leu Ala Glu Leu Ser Glu Ser Leu Arg Asn Arg Ala Glu Glu Trp
        355                 360                 365

Ala Ser Lys Pro Lys Met Val Arg Asp Thr Leu Leu Thr Leu Ala Gly
    370                 375                 380

Cys Thr Pro Tyr Glu Val Arg Phe Lys Lys Asp His Ser Leu Leu Gly
385                 390                 395                 400

Arg Val Phe Ala Phe Asp Ala Val Ser Lys Pro Gly Met Asp Tyr Glu
                405                 410                 415

Leu Lys Leu Phe Ile Glu Tyr Pro Thr Gly Ser Gly Asn Val Tyr Ser
            420                 425                 430

Ser Ala Ser Gly Val Ala Lys Gln Met Tyr Gln Asp Cys Met Lys Asp
        435                 440                 445

Phe Gly Arg Gly Leu Ser Ser Gly Phe Lys Tyr Leu Glu Tyr Glu Lys
    450                 455                 460

Lys His Gly Ser Gly Asp Trp Arg Leu Leu Gly Asp Leu Leu Pro Glu
465                 470                 475                 480

Ala Val Arg Phe Phe Lys Glu Gly Val Pro Gly Ala Asp Met Leu Pro
                485                 490                 495

Gln Pro Tyr Leu Asp Ala Ser Cys Pro Met Leu Pro Thr Ala Leu Val
            500                 505                 510

Ser Leu Ser Arg Ala Pro Ser Ala Pro Pro Gly Thr Gly Ala Leu Pro
        515                 520                 525

Pro Ala Ala Pro Ser Gly Arg Gly Ala Ala Ala Ser Leu Arg Lys Arg
    530                 535                 540

Lys Ala Ser Pro Glu Pro Pro Asp Ser Ala Glu Gly Ala Leu Lys Leu
545                 550                 555                 560

Gly Glu Glu Gln Gln Arg Gln Gln Trp Met Ala Asn Gln Ser Glu Ala
                565                 570                 575

Leu Lys Leu Thr Met Ser Ala Gly Gly Phe Ala Ala Pro Gly His Ala
            580                 585                 590

Ala Gly Gly Pro Pro Pro Pro Pro Pro Pro Leu Gly Pro His Ser Asn
        595                 600                 605

Arg Thr Thr Pro Pro Glu Ser Ala Pro Gln Asn Gly Pro Ser Pro Met
    610                 615                 620

Ala Ala Leu Met Ser Val Ala Asp Thr Leu Gly Thr Ala His Ser Pro
625                 630                 635                 640

Lys Asp Gly Ser Ser Val His Ser Thr Thr Ala Ser Ala Arg Arg Asn
                645                 650                 655

Ser Ser Ser Pro Val Ser Pro Ala Ser Val Pro Gly Gln Arg Arg Leu
            660                 665                 670

Ala Ser Arg Asn Gly Asp Leu Asn Leu Gln Val Ala Pro Pro Pro Pro
        675                 680                 685
```

```
Ser Ala His Pro Gly Met Asp Gln Val His Pro Gln Asn Ile Pro Asp
    690                 695                 700

Ser Pro Met Ala Asn Ser Gly Pro Leu Cys Cys Thr Ile Cys His Glu
705                 710                 715                 720

Arg Leu Glu Asp Thr His Phe Val Gln Cys Pro Ser Val Pro Ser His
                725                 730                 735

Lys Phe Cys Phe Pro Cys Ser Arg Glu Ser Ile Lys Ala Gln Gly Ala
            740                 745                 750

Thr Gly Glu Val Tyr Cys Pro Ser Gly Glu Lys Cys Pro Leu Val Gly
        755                 760                 765

Ser Asn Val Pro Trp Ala Phe Met Gln Gly Glu Ile Ala Thr Ile Leu
    770                 775                 780

Ala Gly Asp Val Lys Val Lys Lys Glu Arg Asp Pro
785                 790                 795


<210> SEQ ID NO 32
<211> LENGTH: 723
<212> TYPE: PRT
<213> ORGANISM: Homo sapiens

<400> SEQUENCE: 32

Ser His Arg Ile Arg Asp Arg Asp Ser Ala Pro Ala Glu Ala Gly Ala
1               5                   10                  15

Arg Leu Leu Pro Gly Arg Pro Leu Pro Arg Ala Ala Ala Ala Ala Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Leu Asn His Val Asp Gly Ser Ser Lys Pro
    50                  55                  60

Ala Val Leu Ala Ala Pro Ser Gly Leu Glu Arg Tyr Gly Leu Ser Ala
65                  70                  75                  80

Ala Ala Ala Ala Ala Ala Ala Ala Ala Ala Ala Val Glu Gln Arg Ser
                85                  90                  95

Arg Phe Glu Tyr Pro Pro Pro Pro Val Ser Leu Gly Ser Ser Ser His
            100                 105                 110

Thr Ala Arg Leu Pro Asn Gly Leu Gly Gly Pro Asn Gly Phe Pro Lys
        115                 120                 125

Pro Thr Pro Glu Glu Gly Pro Pro Glu Leu Asn Arg Gln Ser Pro Asn
    130                 135                 140

Ser Ser Ser Ala Ala Ala Ser Val Ala Ser Arg Arg Gly Thr His Gly
145                 150                 155                 160

Gly Leu Val Thr Gly Leu Pro Asn Pro Gly Gly Gly Gly Gly Pro Gln
                165                 170                 175

Leu Thr Val Pro Pro Asn Leu Leu Pro Gln Thr Leu Leu Asn Gly Pro
            180                 185                 190

Ala Ser Ala Ala Val Leu Pro Pro Pro Pro Pro His Ala Leu Gly Ser
        195                 200                 205

Arg Gly Pro Pro Thr Pro Ala Pro Pro Gly Ala Pro Gly Gly Pro Ala
    210                 215                 220

Cys Leu Gly Gly Thr Pro Gly Val Ser Ala Thr Ser Ser Ser Ala Ser
225                 230                 235                 240

Ser Ser Thr Ser Ser Ser Val Ala Glu Val Gly Val Gly Ala Gly Gly
                245                 250                 255

Lys Arg Pro Gly Ser Val Ser Ser Thr Asp Gln Glu Arg Glu Leu Lys
            260                 265                 270
```

-continued

```
Glu Lys Gln Arg Asn Ala Glu Ala Leu Ala Glu Leu Ser Glu Ser Leu
        275                 280                 285

Arg Asn Arg Ala Glu Glu Trp Ala Ser Lys Pro Lys Met Val Arg Asp
    290                 295                 300

Thr Leu Leu Thr Leu Ala Gly Cys Thr Pro Tyr Glu Val Arg Phe Lys
305                 310                 315                 320

Lys Asp His Ser Leu Leu Gly Arg Val Phe Ala Phe Asp Ala Val Ser
                325                 330                 335

Lys Pro Gly Met Asp Tyr Glu Leu Lys Leu Phe Ile Glu Tyr Pro Thr
            340                 345                 350

Gly Ser Gly Asn Val Tyr Ser Ser Ala Ser Gly Val Ala Lys Gln Met
        355                 360                 365

Tyr Gln Asp Cys Met Lys Asp Phe Gly Arg Gly Leu Ser Ser Gly Phe
    370                 375                 380

Lys Tyr Leu Glu Tyr Glu Lys Lys His Gly Ser Gly Asp Trp Arg Leu
385                 390                 395                 400

Leu Gly Asp Leu Leu Pro Glu Ala Val Arg Phe Phe Lys Glu Gly Val
                405                 410                 415

Pro Gly Ala Asp Met Leu Pro Gln Pro Tyr Leu Asp Ala Ser Cys Pro
            420                 425                 430

Met Leu Pro Thr Ala Leu Val Ser Leu Ser Arg Ala Pro Ser Ala Pro
        435                 440                 445

Pro Gly Thr Gly Ala Leu Pro Pro Ala Ala Pro Ser Gly Arg Gly Ala
    450                 455                 460

Ala Ala Ser Leu Arg Lys Arg Lys Ala Ser Pro Glu Pro Pro Asp Ser
465                 470                 475                 480

Ala Glu Gly Ala Leu Lys Leu Gly Glu Glu Gln Gln Arg Gln Gln Trp
                485                 490                 495

Met Ala Asn Gln Ser Glu Ala Leu Lys Leu Thr Met Ser Ala Gly Gly
            500                 505                 510

Phe Ala Ala Pro Gly His Ala Ala Gly Gly Pro Pro Pro Pro Pro Pro
        515                 520                 525

Pro Leu Gly Pro His Ser Asn Arg Thr Thr Pro Pro Glu Ser Ala Pro
    530                 535                 540

Gln Asn Gly Pro Ser Pro Met Ala Ala Leu Met Ser Val Ala Asp Thr
545                 550                 555                 560

Leu Gly Thr Ala His Ser Pro Lys Asp Gly Ser Ser Val His Ser Thr
                565                 570                 575

Thr Ala Ser Ala Arg Arg Asn Ser Ser Ser Pro Val Ser Pro Ala Ser
            580                 585                 590

Val Pro Gly Gln Arg Arg Leu Ala Ser Arg Asn Gly Asp Leu Asn Leu
        595                 600                 605

Gln Val Ala Pro Pro Pro Pro Ser Ala His Pro Gly Met Asp Gln Val
    610                 615                 620

His Pro Gln Asn Ile Pro Asp Ser Pro Met Ala Asn Ser Gly Pro Leu
625                 630                 635                 640

Cys Cys Thr Ile Cys His Glu Arg Leu Glu Asp Thr His Phe Val Gln
                645                 650                 655

Cys Pro Ser Val Pro Ser His Lys Phe Cys Phe Pro Cys Ser Arg Glu
            660                 665                 670

Ser Ile Lys Ala Gln Gly Ala Thr Gly Glu Val Tyr Cys Pro Ser Gly
        675                 680                 685
```

-continued

```
Glu Lys Cys Pro Leu Val Gly Ser Asn Val Pro Trp Ala Phe Met Gln
    690                 695                 700

Gly Glu Ile Ala Thr Ile Leu Ala Gly Asp Val Lys Val Lys Lys Glu
705                 710                 715                 720

Arg Asp Pro


<210> SEQ ID NO 33
<211> LENGTH: 172
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Unknown
<220> FEATURE:
<221> NAME/KEY: MISC_FEATURE
<222> LOCATION: (38)..(38)
<223> OTHER INFORMATION: Unknown

<400> SEQUENCE: 33

Val Ala Arg Thr Ala Arg Lys Arg Lys Pro Ser Pro Glu Pro Glu Gly
1               5                   10                  15

Glu Val Gly Pro Pro Lys Ile Asn Gly Glu Ala Gln Pro Trp Xaa Ser
            20                  25                  30

Thr Ser Thr Glu Gly Xaa Lys Ile Pro Met Thr Pro Thr Ser Ser Phe
        35                  40                  45

Val Ser Pro Pro Pro Pro Thr Ala Ser Pro His Ser Asn Arg Thr Thr
    50                  55                  60

Pro Pro Glu Ala Ala Gln Asn Gly Gln Ser Pro Met Ala Ala Leu Ile
65                  70                  75                  80

Leu Val Ala Asp Asn Ala Gly Gly Ser His Ala Ser Lys Asp Ala Asn
                85                  90                  95

Gln Val His Ser Thr Thr Arg Arg Asn Ser Asn Ser Pro Pro Ser Pro
            100                 105                 110

Ser Ser Met Asn Gln Arg Arg Leu Gly Pro Arg Glu Val Gly Gly Gln
        115                 120                 125

Gly Ala Gly Asn Thr Gly Gly Leu Glu Pro Val His Pro Ala Ser Leu
    130                 135                 140

Pro Asp Phe Ser Leu Ala Thr Ser Ala Pro Leu Cys Cys Thr Leu Cys
145                 150                 155                 160

His Glu Arg Leu Glu Asp Asn His Phe Val Gln Cys
                165                 170


<210> SEQ ID NO 34
<211> LENGTH: 197
<212> TYPE: PRT
<213> ORGANISM: Homo sapiens

<400> SEQUENCE: 34

Met Thr Pro Thr Ser Ser Phe Val Ser Pro Pro Pro Pro Thr Ala Ser
1               5                   10                  15

Pro His Ser Asn Arg Thr Thr Pro Pro Glu Ala Ala Gln Asn Gly Gln
            20                  25                  30

Ser Pro Met Ala Ala Leu Ile Leu Val Ala Asp Asn Ala Gly Gly Ser
        35                  40                  45

His Ala Ser Lys Asp Ala Asn Gln Val His Ser Thr Thr Arg Arg Asn
    50                  55                  60

Ser Asn Ser Pro Pro Ser Pro Ser Ser Met Asn Gln Arg Arg Leu Gly
65                  70                  75                  80
```

```
Pro Arg Glu Val Gly Gly Gln Gly Ala Gly Asn Thr Gly Gly Leu Glu
                85                  90                  95

Pro Val His Pro Ala Ser Leu Pro Asp Ser Ser Leu Ala Thr Ser Ala
            100                 105                 110

Pro Leu Cys Cys Thr Leu Cys His Glu Arg Leu Glu Asp Thr His Phe
        115                 120                 125

Val Gln Cys Pro Ser Val Pro Ser His Lys Phe Cys Phe Pro Cys Ser
    130                 135                 140

Arg Gln Ser Ile Lys Gln Gln Gly Ala Ser Gly Glu Val Tyr Cys Pro
145                 150                 155                 160

Ser Gly Glu Lys Cys Pro Leu Val Gly Ser Asn Val Pro Trp Ala Phe
                165                 170                 175

Met Gln Gly Glu Ile Ala Thr Ile Leu Ala Gly Asp Val Lys Val Lys
            180                 185                 190

Lys Glu Arg Asp Ser
        195


<210> SEQ ID NO 35
<211> LENGTH: 197
<212> TYPE: PRT
<213> ORGANISM: Homo sapiens

<400> SEQUENCE: 35

Met Thr Pro Thr Ser Ser Phe Val Ser Pro Pro Pro Pro Thr Ala Ser
1               5                   10                  15

Pro His Ser Asn Arg Thr Thr Pro Pro Glu Ala Ala Gln Asn Gly Gln
            20                  25                  30

Ser Pro Met Ala Ala Leu Ile Leu Val Ala Asp Asn Ala Gly Gly Ser
        35                  40                  45

His Ala Ser Lys Asp Ala Asn Gln Val His Ser Thr Thr Arg Arg Asn
    50                  55                  60

Ser Asn Ser Pro Pro Ser Pro Ser Ser Met Asn Gln Arg Arg Leu Gly
65                  70                  75                  80

Pro Arg Glu Val Gly Gly Gln Gly Ala Gly Asn Thr Gly Gly Leu Glu
                85                  90                  95

Pro Val His Pro Ala Ser Leu Pro Asp Ser Ser Leu Ala Thr Ser Ala
            100                 105                 110

Pro Leu Cys Cys Thr Leu Cys His Glu Arg Leu Glu Asp Thr His Phe
        115                 120                 125

Val Gln Cys Pro Ser Val Pro Ser His Lys Phe Cys Phe Pro Cys Ser
    130                 135                 140

Arg Gln Ser Ile Lys Gln Gln Gly Ala Ser Gly Glu Val Tyr Cys Pro
145                 150                 155                 160

Ser Gly Glu Lys Cys Pro Leu Val Gly Ser Asn Val Pro Trp Ala Phe
                165                 170                 175

Met Gln Gly Glu Ile Ala Thr Ile Leu Ala Gly Asp Val Lys Val Lys
            180                 185                 190

Lys Glu Arg Asp Ser
        195


<210> SEQ ID NO 36
<211> LENGTH: 216
<212> TYPE: PRT
<213> ORGANISM: Homo sapiens

<400> SEQUENCE: 36
```

-continued

```
Met Ser Ala Gly Gly Phe Ala Ala Pro Gly His Ala Ala Gly Gly Pro
1               5                   10                  15

Pro Pro Pro Pro Pro Pro Leu Gly Pro His Ser Asn Arg Thr Thr Pro
            20                  25                  30

Pro Glu Ser Ala Pro Gln Asn Gly Pro Ser Pro Met Ala Ala Leu Met
        35                  40                  45

Ser Val Ala Asp Thr Leu Gly Thr Ala His Ser Pro Lys Asp Gly Ser
    50                  55                  60

Ser Val His Ser Thr Thr Ala Ser Ala Arg Arg Asn Ser Ser Ser Pro
65                  70                  75                  80

Val Ser Pro Ala Ser Val Pro Gly Gln Arg Arg Leu Ala Ser Arg Asn
                85                  90                  95

Gly Asp Leu Asn Leu Gln Val Ala Pro Pro Pro Pro Ser Ala His Pro
            100                 105                 110

Gly Met Asp Gln Val His Pro Gln Asn Ile Pro Asp Ser Pro Met Ala
        115                 120                 125

Asn Ser Gly Pro Leu Cys Cys Thr Ile Cys His Glu Arg Leu Glu Asp
    130                 135                 140

Thr His Phe Val Gln Cys Pro Ser Val Pro Ser His Lys Phe Cys Phe
145                 150                 155                 160

Pro Cys Ser Arg Glu Ser Ile Lys Ala Gln Gly Ala Thr Gly Glu Val
                165                 170                 175

Tyr Cys Pro Ser Gly Glu Lys Cys Pro Leu Val Gly Ser Asn Val Pro
            180                 185                 190

Trp Ala Phe Met Gln Gly Glu Ile Ala Thr Ile Leu Ala Gly Asp Val
        195                 200                 205

Lys Val Lys Lys Glu Arg Asp Pro
    210                 215
```

<210> SEQ ID NO 37
<211> LENGTH:
<212> TYPE:
<213> ORGANISM:

<400> SEQUENCE: 37

000

<210> SEQ ID NO 38
<211> LENGTH:
<212> TYPE:
<213> ORGANISM:

<400> SEQUENCE: 38

000

<210> SEQ ID NO 39
<211> LENGTH:
<212> TYPE:
<213> ORGANISM:

<400> SEQUENCE: 39

000

<210> SEQ ID NO 40
<211> LENGTH:
<212> TYPE:
<213> ORGANISM:

<400> SEQUENCE: 40

000

<210> SEQ ID NO 41
<211> LENGTH: 923
<212> TYPE: DNA
<213> ORGANISM: Homo sapiens

<400> SEQUENCE: 41

```
gtcgaccacg cgtccgggag acagaaagag ggtggtggcc gatagctggt cctctttctc      60
caacacctag cctgagactt ggcggcgcgg ctgctatcct gaactagctt ggtaagtgtt     120
gtgtcccgaa ccagcgtaga gagacctcgg accagccgcc ttgatgacag catccgcgtc     180
ctccttttca tcatctcagg gtgtccagca gccctccatc tacagcttct cccaaataac     240
cagaagcttg tttctcagca atggtgtggc cgccaacgac aaactccttc tgtccagcaa     300
tcgcatcacc gccattgtca atgcctcggt ggaagtggtc aacgtattct tcgagggcat     360
tcagtacata aaggtgcctg ttaccgatgc tcgtgactcg cgtctctacg actttttga      420
ccccattgct gatcttatcc acaccatcga tatgaggcag ggccgtacgc tgctgcactg     480
catggctgga gtgagccgtt ccgcctcact gtgccttgcg tacctcatga aataccactc     540
catgtcgctg ctggacgccc atacatggac caagtcgcgc cgccccatca tccggcccaa     600
caacggcttt tgggaacagc tcatcaatta cgaattcaag ctgtttaata acaacaccgt     660
gcgcatgatc aactcgccgg taggtaacat ccctgacatc tatgagaagg acctacgtac     720
gatgatatca atgtaagcca tcccggccag cccctgacat ctgccatcga tcttgcacca     780
agactgaact tgaacactga cattttgtta gtaaagaaaa ccggatggtg ccttgttaaa     840
gggcaagaaa aaagggaggg ggttggagtt ttgaacgtag taagccttac cttaatagaa     900
ttaaattcat gaaacataaa aca                                             923
```

<210> SEQ ID NO 42
<211> LENGTH: 190
<212> TYPE: PRT
<213> ORGANISM: Homo sapiens

<400> SEQUENCE: 42

```
Met Thr Ala Ser Ala Ser Ser Phe Ser Ser Ser Gln Gly Val Gln Gln
1               5                   10                  15

Pro Ser Ile Tyr Ser Phe Ser Gln Ile Thr Arg Ser Leu Phe Leu Ser
            20                  25                  30

Asn Gly Val Ala Ala Asn Asp Lys Leu Leu Leu Ser Ser Asn Arg Ile
        35                  40                  45

Thr Ala Ile Val Asn Ala Ser Val Glu Val Val Asn Val Phe Phe Glu
    50                  55                  60

Gly Ile Gln Tyr Ile Lys Val Pro Val Thr Asp Ala Arg Asp Ser Arg
65                  70                  75                  80

Leu Tyr Asp Phe Phe Asp Pro Ile Ala Asp Leu Ile His Thr Ile Asp
                85                  90                  95

Met Arg Gln Gly Arg Thr Leu Leu His Cys Met Ala Gly Val Ser Arg
            100                 105                 110

Ser Ala Ser Leu Cys Leu Ala Tyr Leu Met Lys Tyr His Ser Met Ser
        115                 120                 125

Leu Leu Asp Ala His Thr Trp Thr Lys Ser Arg Arg Pro Ile Ile Arg
    130                 135                 140
```

-continued

```
Pro Asn Asn Gly Phe Trp Glu Gln Leu Ile Asn Tyr Glu Phe Lys Leu
145                 150                 155                 160

Phe Asn Asn Asn Thr Val Arg Met Ile Asn Ser Pro Val Gly Asn Ile
                165                 170                 175

Pro Asp Ile Tyr Glu Lys Asp Leu Arg Thr Met Ile Ser Met
            180                 185                 190


<210> SEQ ID NO 43
<211> LENGTH: 570
<212> TYPE: DNA
<213> ORGANISM: Homo sapiens

<400> SEQUENCE: 43

atgacagcat ccgcgtcctc cttttcatca tctcagggtg tccagcagcc ctccatctac      60

agcttctccc aaataaccag aagcttgttt ctcagcaatg gtgtggccgc caacgacaaa     120

ctccttctgt ccagcaatcg catcaccgcc attgtcaatg cctcggtgga agtggtcaac     180

gtattcttcg agggcattca gtacataaag gtgcctgtta ccgatgctcg tgactcgcgt     240

ctctacgact tttttgaccc cattgctgat cttatccaca ccatcgatat gaggcagggc     300

cgtacgctgc tgcactgcat ggctggagtg agccgttccg cctcactgtg ccttgcgtac     360

ctcatgaaat accactccat gtcgctgctg gacgcccata catggaccaa gtcgcgccgc     420

cccatcatcc ggcccaacaa cggcttttgg gaacagctca tcaattacga attcaagctg     480

tttaataaca acaccgtgcg catgatcaac tcgccggtag gtaacatccc tgacatctat     540

gagaaggacc tacgtacgat gatatcaatg                                       570


<210> SEQ ID NO 44
<211> LENGTH: 190
<212> TYPE: PRT
<213> ORGANISM: Homo sapiens

<400> SEQUENCE: 44

Met Thr Ala Ser Ala Ser Ser Phe Ser Ser Ser Gln Gly Val Gln Gln
1               5                   10                  15

Pro Ser Ile Tyr Ser Phe Ser Gln Ile Thr Arg Ser Leu Phe Leu Ser
            20                  25                  30

Asn Gly Val Ala Ala Asn Asp Lys Leu Leu Leu Ser Ser Asn Arg Ile
        35                  40                  45

Thr Ala Ile Val Asn Ala Ser Val Glu Val Val Asn Val Phe Phe Glu
    50                  55                  60

Gly Ile Gln Tyr Ile Lys Val Pro Val Thr Asp Ala Arg Asp Ser Arg
65                  70                  75                  80

Leu Tyr Asp Phe Phe Asp Pro Ile Ala Asp Leu Ile His Thr Ile Asp
                85                  90                  95

Met Arg Gln Gly Arg Thr Leu Leu His Cys Met Ala Gly Val Ser Arg
            100                 105                 110

Ser Ala Ser Leu Cys Leu Ala Tyr Leu Met Lys Tyr His Ser Met Ser
        115                 120                 125

Leu Leu Asp Ala His Thr Trp Thr Lys Ser Arg Arg Pro Ile Ile Arg
    130                 135                 140

Pro Asn Asn Gly Phe Trp Glu Gln Leu Ile Asn Tyr Glu Phe Lys Leu
145                 150                 155                 160
```

-continued

```
Phe Asn Asn Asn Thr Val Arg Met Ile Asn Ser Pro Val Gly Asn Ile
            165                 170                 175

Pro Asp Ile Tyr Glu Lys Asp Leu Arg Met Met Ile Ser Met
        180                 185                 190
```